United States Patent
Lei et al.

(10) Patent No.: US 11,319,330 B2
(45) Date of Patent: May 3, 2022

(54) TRICYCLIC FURAN-SUBSTITUTED PIPERIDINEDIONE COMPOUND

(71) Applicant: MEDSHINE DISCOVERY INC., Jiangsu (CN)

(72) Inventors: Maoyi Lei, Shanghai (CN); Yunfu Luo, Shanghai (CN); Yu Xu, Shanghai (CN); Guoli Zhang, Shanghai (CN); Jinghong Dong, Shanghai (CN); Jian Li, Shanghai (CN); Shuhui Chen, Shanghai (CN)

(73) Assignee: MEDSHINE DISCOVERY INC., Nanjing (CN)

( * ) Notice: Subject to any disclaimer, the term of this patent is extended or adjusted under 35 U.S.C. 154(b) by 0 days.

(21) Appl. No.: 17/274,236

(22) PCT Filed: Sep. 9, 2019

(86) PCT No.: PCT/CN2019/104992
§ 371 (c)(1),
(2) Date: Mar. 8, 2021

(87) PCT Pub. No.: WO2020/048547
PCT Pub. Date: Mar. 12, 2020

(65) Prior Publication Data
US 2021/0317138 A1    Oct. 14, 2021

(30) Foreign Application Priority Data

Sep. 7, 2018 (CN) .......................... 201811048512.X
Nov. 14, 2018 (CN) .......................... 201811356415.7
Mar. 22, 2019 (CN) .......................... 201910225326.7

(51) Int. Cl.
| | | |
|---|---|---|
| C07D 405/04 | (2006.01) | |
| C07D 405/12 | (2006.01) | |
| C07D 513/04 | (2006.01) | |
| C07D 491/048 | (2006.01) | |
| C07D 498/04 | (2006.01) | |
| A61P 35/00 | (2006.01) | |

(52) U.S. Cl.
CPC ............ *C07D 513/04* (2013.01); *A61P 35/00* (2018.01); *C07D 405/04* (2013.01); *C07D 405/12* (2013.01); *C07D 491/048* (2013.01); *C07D 498/04* (2013.01)

(58) Field of Classification Search
CPC .. C07D 513/04; C07D 405/04; C07D 405/12; C07D 491/048; C07D 498/04; A61P 35/00
See application file for complete search history.

(56) References Cited

U.S. PATENT DOCUMENTS

2015/0224104 A1    8/2015   Gandhi et al.

FOREIGN PATENT DOCUMENTS

| CN | 104797256 A | 7/2015 |
|---|---|---|
| EP | 1690538 A1 | 8/2006 |
| WO | WO-2004063190 A1 | 7/2004 |
| WO | WO-2012125459 A1 | 9/2012 |
| WO | WO-2014025960 A1 | 2/2014 |

OTHER PUBLICATIONS

Oct. 8, 2019 International Search Report issued in International Patent Application No. PCT/CN2019/104992.
Oct. 8, 2019 Written Opinion of the International Searching Authority issued in International Patent Application No. PCT/CN2019/104992.
Chinese Office Action regarding Application No. 201980058617.X, dated Feb. 8, 2022.

*Primary Examiner* — Rebecca L Anderson

(57) ABSTRACT

Disclosed are a series of tricyclic furan-substituted piperidinedione compounds and an application thereof in preparing a drug for treating a disease related to CRBN protein. In particular, disclosed is a derivative compound represented by formula (I) or a pharmaceutically acceptable salt thereof.

(I)

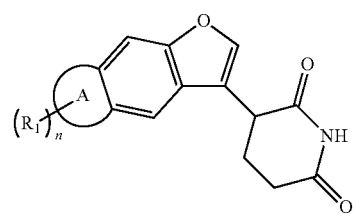

15 Claims, 1 Drawing Sheet

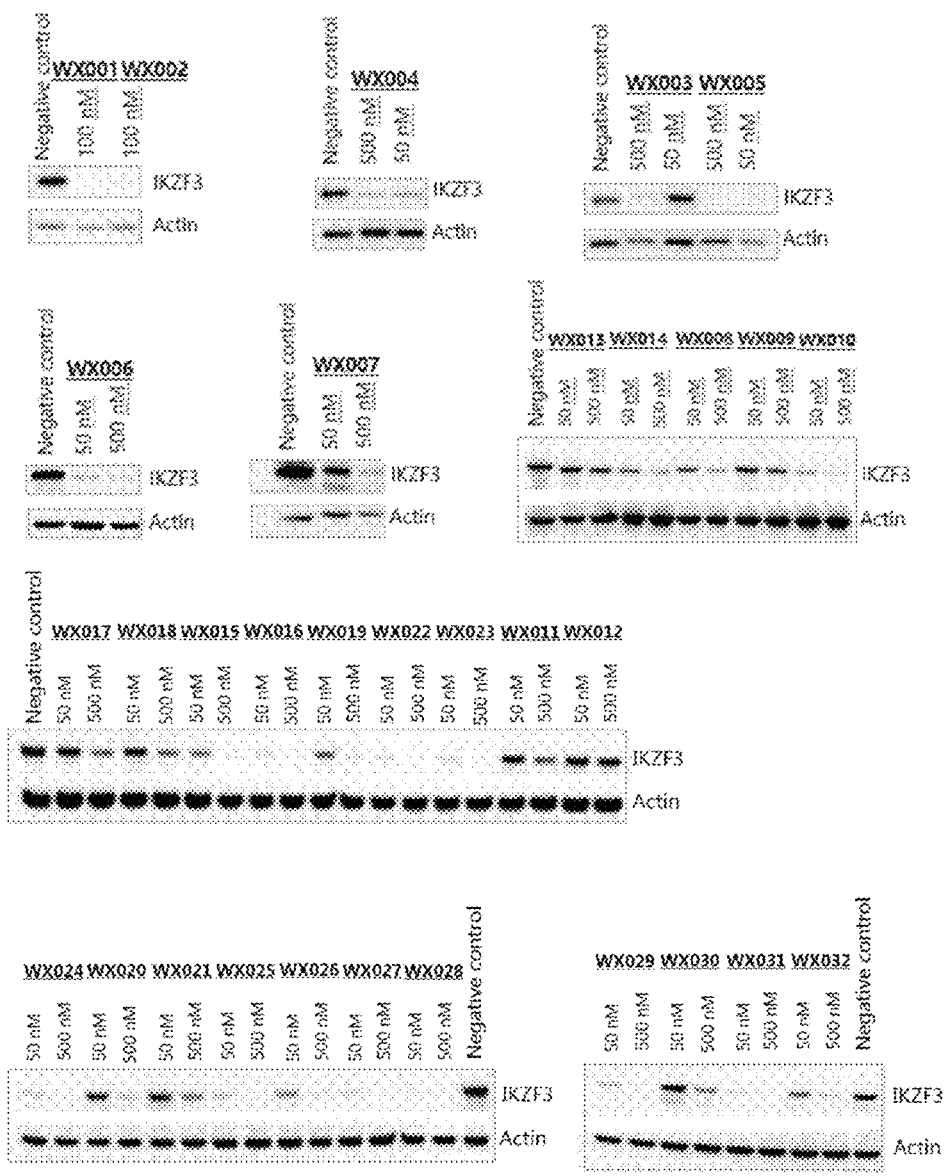

TRICYCLIC FURAN-SUBSTITUTED PIPERIDINEDIONE COMPOUND

CROSS-REFERENCE TO RELATED APPLICATIONS

This application is a U.S. National Phase Application under 35 U.S.C. 371 of International Application No. PCT/CN2019/104992, filed Sep. 9, 2019, which claims the benefit of Chinese Patent Application No. CN 201811048512.X, filed Sep. 7, 2018, Chinese Patent Application No. CN 201811356415.7, filed Nov. 14, 2018, and Chinese Patent Application No. CN 201910225326.7, filed Mar. 22, 2019.

TECHNICAL FIELD

The present disclosure relates to a series of tricyclic furan-substituted piperidinedione compounds and an application thereof in preparing a drug for treating a disease related to CRBN protein, and specifically to a derivative compound represented by formula (I) or a pharmaceutically acceptable salt thereof.

BACKGROUND

Thalidomide, with the trade name Thalomid, was first synthesized by the German company Grünenthal. From the second half of the 1950s to the early 1960s, it was sold as a sedative in more than 40 countries and widely used as an antiemetic drug for pregnant women. It eventually led to the tragedy of tens of thousands of infants with phocomelia (disorders of morphogenesis) and withdraw from the market.

Since the "thalomid" incident, the teratogenic mechanism of thalidomide has aroused great interest among scientific researchers. It has been confirmed that the protein Cereblon (CRBN) is a target protein for the teratogenic effects of thalidomide. Thalidomide combines with CRBN, DDB1 (Damaged DNA Binding Protein 1), CUL4A (Cullin-4A) and Cullins 1 regulator (ROC1) to form an E3 ubiquitin ligase complex, which ubiquitinates a variety of substrate proteins to form a ubiquitinated chain, so that the substrate proteins are recognized and hydrolyzed by the proteasome. Domide drugs are called immunomodulatory drugs (IMiDs), which activate the ubiquitination of transcription factors IKZF1 and IKZF3 by the E3 ubiquitin ligase complex formed by domide drugs with CRBN, and then the ubiquitinated transcription factors are recognized and degraded by a proteasome. Therefore, domide drugs have a toxic effect on multiple myeloma. The loss of these two transcription factors will stop the growth of myeloma. Now the domide drugs such as lenalidomide and pomalidomide are the first-line drugs for the treatment of multiple myeloma.

CRBN is a protein consisting of 442 amino acids conserved from plants to human and located on the p26.3 short arm of human chromosome 3 and has a molecular weight of 51 kDa. In human, the CRBN gene has been identified as a candidate gene for autosomal recessive inheritance non-syndromic mild mental retardation (ARNSMR). CRBN is widely expressed in testis, spleen, prostate, liver, pancreas, placenta, kidney, lung, skeletal muscle, ovary, small intestine, peripheral blood leukocytes, colon, brain and retina, and the expression in brain tissue (including retina) and testis is significantly higher than other tissues.

CRBN, as an important target for anti-tumor and immunomodulator drugs, has been demonstrated to have clear efficacy in hematological malignancies such as multiple myeloma and chronic lymphocytic leukemia, skin diseases such as leprosy erythema nodosum, and autoimmune disease such as systemic lupus erythematosus. Domide drugs have relatively more side effects, especially peripheral neuropathy. There is an urgent need to develop CRBN modulator drugs with no teratogenic effects, less peripheral neuropathy, stronger immunomodulatory effects, and higher anti-tumor activities to improve clinical efficacy, reduce clinical side effects, and facilitate long-term use by patients.

CONTENT OF THE PRESENT INVENTION

The present disclosure provides a compound represented by formula (I) or a pharmaceutically acceptable salt thereof,

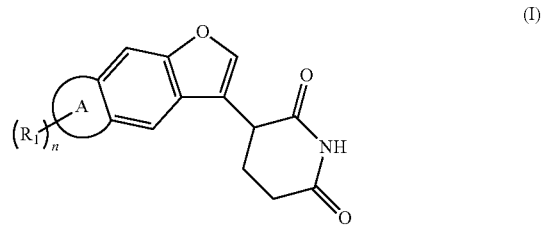

wherein n is selected from 0, 1, 2 and 3;

$R_1$ is selected from independently selected from H, F, Cl, Br, I, OH, $NH_2$, $C_{1-6}$alkyl, $C_{1-6}$alkoxy and

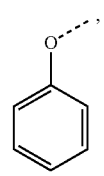

wherein the $C_{1-6}$alkyl, $C_{1-6}$alkoxy and

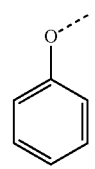

are optionally substituted with 1, 2 or 3 $R_a$;

$R_a$ is independently selected from H, F, Cl, Br, I, OH, $NH_2$, $C_{1-10}$alkyl, $C_{1-10}$alkoxy, $C_{1-10}$alkylamino, —NHC(=O)—$C_{1-10}$alkyl, 5- to 10-membered heterocycloalkyl, 5- to 10-membered heterocycloalkylamino and $C_{5-10}$cycloalkylamino, wherein the $C_{1-10}$alkyl, $C_{1-10}$alkoxy, $C_{1-10}$alkylamino, —NHC(=O)—$C_{1-10}$alkyl, 5- to 10-membered heterocycloalkyl, 5- to 10-membered heterocycloalkylamino and $C_{5-10}$cycloalkylamino are optionally substituted with 1, 2 or 3 R;

R is independently selected from F, Cl, Br, I, OH, $NH_2$, CN, Me and

ring A is selected from 5- to 6-membered heteroaryl, phenyl, $C_{4-6}$cycloalkyl, 4- to 7-membered heterocycloalkyl and 4- to 7-membered heterocycloalkenyl;

the 5- to 6-membered heteroaryl, 4- to 7-membered heterocycloalkyl, 5- to 10-membered heterocycloalkyl and 5- to 10-membered heterocycloalkylamino comprise 1, 2, 3 or 4 heteroatoms or heteroatom groups independently selected from —NH—, —O—, —S— and N respectively.

In some embodiments of the present disclosure, the above-mentioned compound represented by formula (I) or a pharmaceutically acceptable salt thereof is selected from

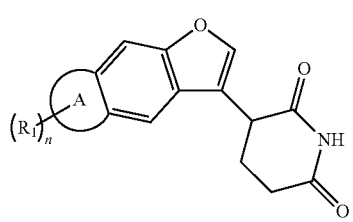

wherein n is selected from 0, 1, 2 and 3;

$R_1$ is selected from H, halogen, OH, $NH_2$ and $C_{1-6}$ alkyl, wherein the $C_{1-6}$ alkyl is optionally substituted with 1, 2 or 3 $R_a$;

$R_a$ is selected from F, Cl, Br, I, OH, $NH_2$ and CN;

ring A is selected from 5- to 6-membered heteroaryl, phenyl, $C_{4-6}$cycloalkyl and 4- to 7-membered heterocycloalkyl;

The 5 to 6-membered heteroaryl and 4 to 7-membered heterocycloalkyl comprise 1, 2, 3 or 4 heteroatoms or heteroatom groups independently selected from —NH—, —O—, —S— and N, respectively.

In some embodiments of the present disclosure, ring A is selected from phenyl, 1,3-dioxolane, morpholinyl, tetrahydrofuryl, furyl and oxazolyl.

In some embodiments of the present disclosure, the above-mentioned compound represented by formula (I) or a pharmaceutically acceptable salt thereof is selected from

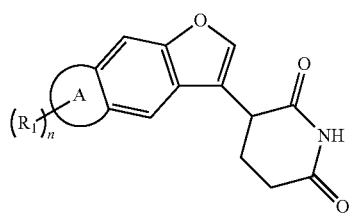

wherein n is selected from 0, 1, 2 and 3;

$R_1$ is selected from H, halogen, OH, $NH_2$ and $C_{1-6}$ alkyl, wherein the $C_{1-6}$ alkyl is optionally substituted with 1, 2 or 3 $R_a$;

$R_a$ is selected from F, Cl, Br, I, OH, $NH_2$ and CN;

ring A is selected from 5- to 6-membered heteroaryl, phenyl, $C_{4-6}$cycloalkyl and 4- to 7-membered heterocycloalkyl;

The 5 to 6-membered heteroaryl and 4 to 7-membered heterocycloalkyl comprise 1, 2, 3 or 4 heteroatoms or heteroatom groups independently selected from —NH—, —O—, —S— and N, respectively.

In some embodiments of the present disclosure, the above-mentioned $R_a$ is independently selected from H, F, Cl, Br, I, OH, $NH_2$, $C_{1-6}$alkyl, $C_{1-6}$alkoxy, $C_{1-6}$alkylamino, —NHC(=O)—$C_{1-6}$alkyl, 5- to 8-membered heterocycloalkyl, 5- to 8-membered heterocycloalkylamino and $C_{5-8}$cycloalkylamino, wherein the $C_{1-6}$alkyl, $C_{1-6}$alkoxy, $C_{1-6}$alkylamino, —NHC(=O)—$C_{1-6}$alkyl, 5- to 8-membered heterocycloalkyl, 5- to 8-membered heterocycloalkylamino and $C_{5-8}$cycloalkylamino are optionally substituted with 1, 2 or 3 R.

In some embodiments of the present disclosure, the above-mentioned $R_a$ is independently selected from H, F, Cl, Br, I, OH, $NH_2$, $C_{1-3}$alkyl, $C_{1-3}$alkoxy, $C_{1-3}$alkylamino, —NHC(=O)—$C_{1-3}$alkyl, piperidinyl, piperazinyl, morpholinyl, pyranyl, pyrrolidinyl, cyclohexylamino, tetrahydropyranylamino, piperidinylamino, piperazinylamino and 3-azabicyclo[3,1,0]hexyl, wherein the $C_{1-3}$alkyl, $C_{1-6}$alkoxy, $C_{1-6}$alkylamino, —NHC(=O)—$C_{1-3}$alkyl, piperidinyl, piperazinyl, morpholinyl, pyranyl, pyrrolidinyl, cyclohexylamino, tetrahydropyranylamino, piperidinylamino, piperazinylamino and 3-azabicyclo[3,1,0]hexyl are optionally substituted with 1, 2 or 3 R.

In some embodiments of the present disclosure, the above-mentioned $R_a$ is independently selected from H, F, Cl, Br, I, OH, $NH_2$, Me, Et,

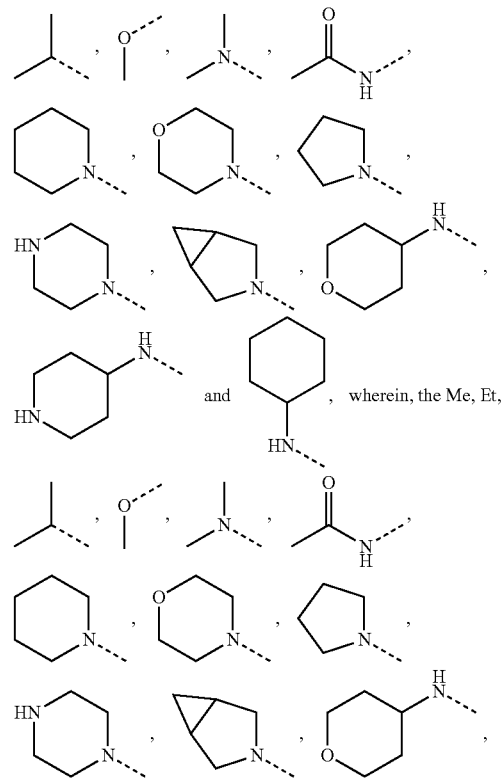

, wherein, the Me, Et,

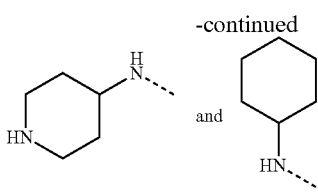

are optionally substituted with 1, 2 or 3 R, and other variables are as defined in the present disclosure.

In some embodiments of the present disclosure, the above-mentioned $R_a$ is independently selected from H, F, Cl, Br, I, OH, $NH_2$,

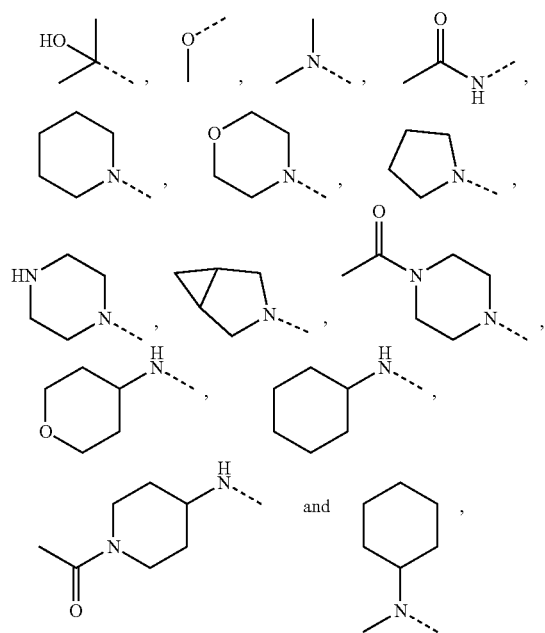

and other variables are as defined in the present disclosure.

In some embodiments of the present disclosure, the above-mentioned $R_1$ is independently selected from H, F, Cl, Br, I, OH, $NH_2$, Me, $C_{1-6}$alkoxy and

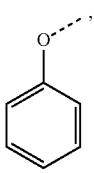

wherein the Me, $C_{1-6}$alkoxy and

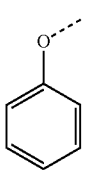

are optionally substituted with 1, 2 or 3 $R_a$, and other variables are as defined in the present disclosure.

In some embodiments of the present disclosure, the above-mentioned $R_1$ is selected from H, F, Cl, Br, I, OH, $NH_2$ and $C_{1-3}$alkyl, wherein the $C_{1-3}$alkyl is optionally substituted with 1, 2 or 3 $R_a$, and other variables are as defined in the present disclosure.

In some embodiments of the present disclosure, the above-mentioned $R_1$ is selected from H, F, Cl, Br, I, OH, $NH_2$ and Me, wherein the Me is optionally substituted with 1, 2 or 3 $R_a$, and other variables are as defined in the present disclosure.

In some embodiments of the present disclosure, the above-mentioned $R_1$ is selected from H and Me, and other variables are as defined in the present disclosure.

In some embodiments of the present disclosure, the above-mentioned $R_1$ is selected from F, Cl, Br, I, OH, $NH_2$ and $C_{1-3}$alkyl, wherein the $C_{1-3}$alkyl is optionally substituted with 1, 2 or 3 $R_a$, and other variables are as defined in the present disclosure.

In some embodiments of the present disclosure, the above-mentioned $R_1$ is selected from F, Cl, Br, I, OH, $NH_2$ and Me, wherein the Me is optionally substituted with 1, 2 or 3 $R_a$, and other variables are as defined in the present disclosure.

In some embodiments of the present disclosure, the above-mentioned $R_1$ is selected from H, Me,

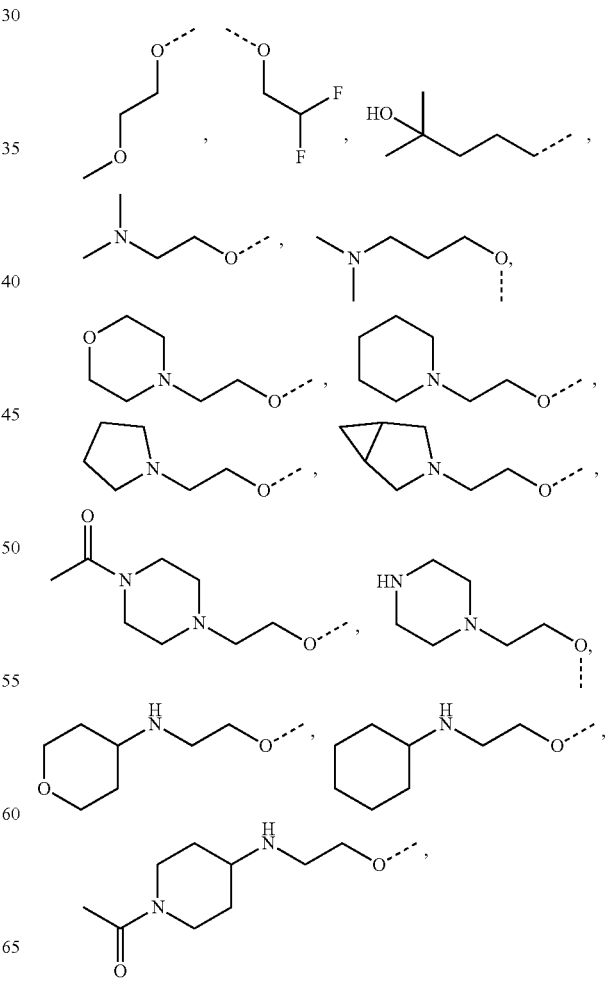

-continued

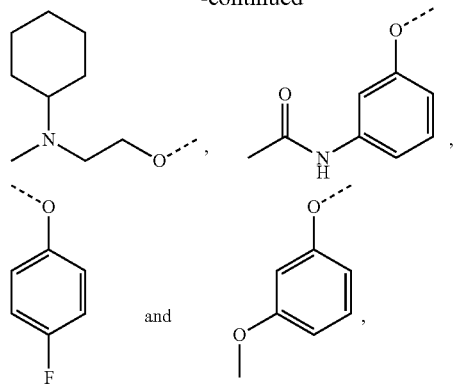

and other variables are as defined in the present disclosure.

In some embodiments of the present disclosure, the above-mentioned $R_1$ is selected from Me, and other variables are as defined in the present disclosure.

Heteroatoms or heteroatom groups are independently selected from —NH—, —O—, —S— and N.

In some embodiments of the present disclosure, the above-mentioned ring A is selected from phenyl, 1,3-dioxolane, morpholinyl, tetrahydrofuryl, 2,3-dihydrofuryl, furyl, pyrazolyl, thiazolyl, 4,5-dihydrothiazolyl, oxazolyl, 2,3-dihydrooxazolyl, pyridinyl and 2,3-dihydropyridinyl, and other variables are as defined in the present disclosure.

In some embodiments of the present disclosure, the above-mentioned ring A is selected from phenyl, 1,3-dioxolane, morpholinyl, oxazolyl, cyclobutyl, oxepanyl and 1,4-oxazepinyl, and other variables are as defined in the present disclosure.

In some embodiments of the present disclosure, the above-mentioned ring A is selected from phenyl, 1,3-dioxolane, morpholinyl and oxazolyl, and other variables are as defined in the present disclosure, and other variables are as defined in the present disclosure.

In some embodiments of the present disclosure, the above-mentioned ring A is selected from phenyl, 1,3-dioxolane, morpholinyl, tetrahydrofuryl, furyl and oxazolyl, and other variables are as defined in the present disclosure.

In some embodiments of the present disclosure, the above-mentioned ring A is selected from phenyl, 1,3-dioxolane, morpholinyl, oxazolyl, cyclobutyl, oxepanyl, thienyl, tetrahydrothienyl, furyl, tetrahydrofuryl and 1,4-oxazepinyl, and other variables are as defined in the present disclosure.

In some embodiments of the present disclosure, the above-mentioned ring A is selected from phenyl, 1,3-dioxolane, morpholinyl, tetrahydrofuryl and oxazolyl, and other variables are as defined in the present disclosure.

In some embodiments of the present disclosure, the structural unit

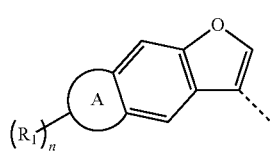

is selected from

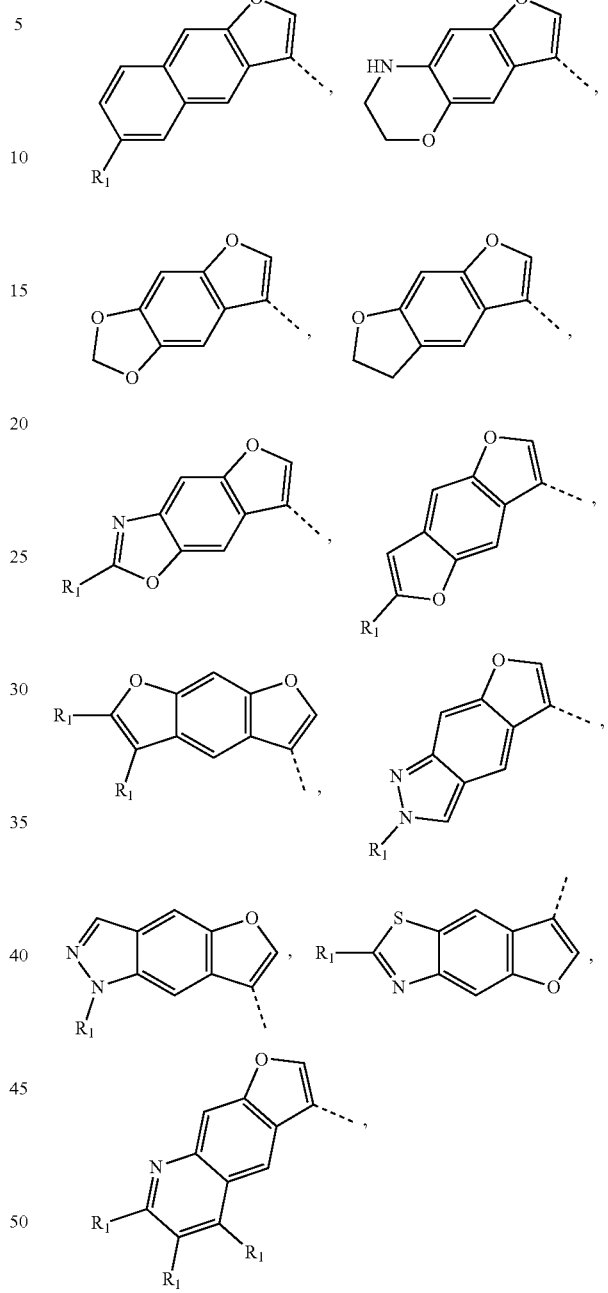

and other variables are as defined in the present disclosure.

In some embodiments of the present disclosure, the structural unit

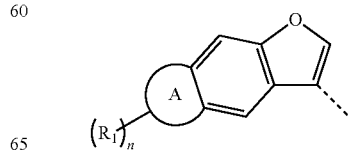

is selected from

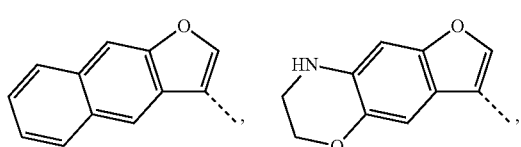

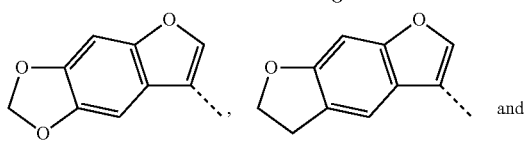

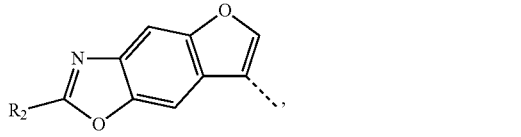

and other variables are as defined in the present disclosure.

In some embodiments of the present disclosure, the structural unit

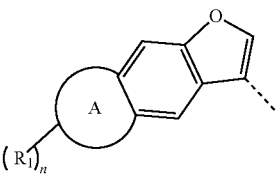

is selected from

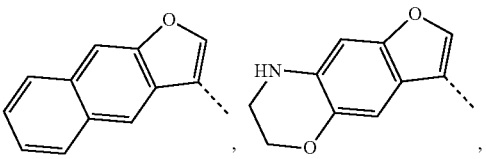

and

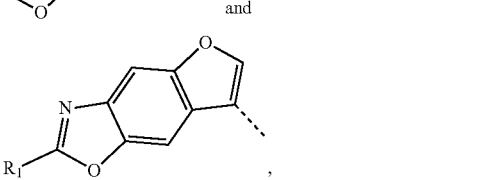

and other variables are as defined in the present disclosure.

In some embodiments of the present disclosure, the structural unit

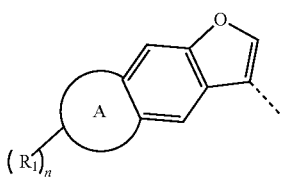

is selected from

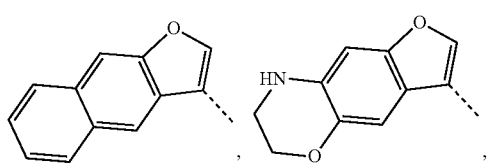

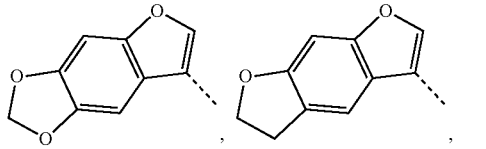

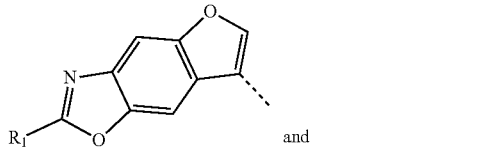

and

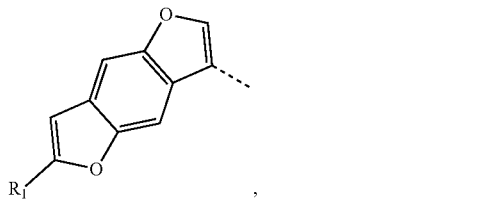

and other variables are as defined in the present disclosure.

In some embodiments of the present disclosure, the structural unit

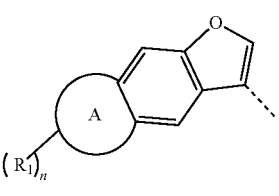

is selected from

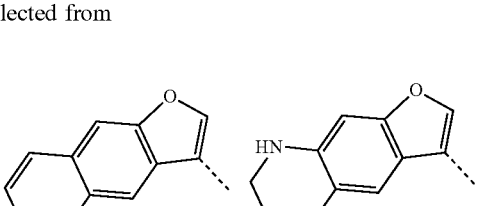

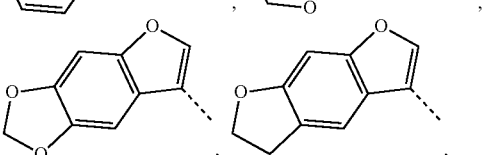

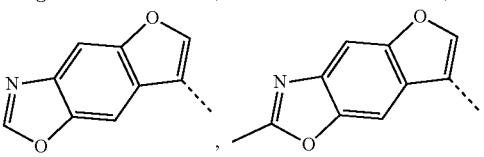

and

-continued

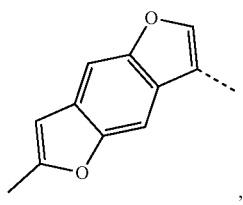

,

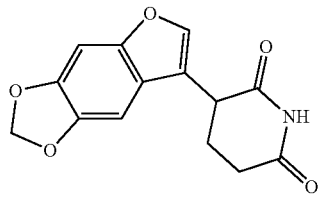

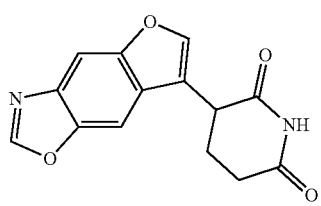

and other variables are as defined in the present disclosure.

Other solutions of the present disclosure can be generated by any combination of the above variables. In some embodiments of the present disclosure, the above-mentioned compound or a pharmaceutically acceptable salt thereof is selected from

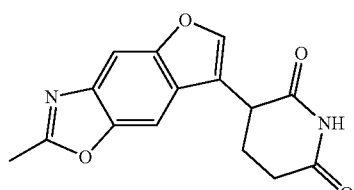

(I-1)

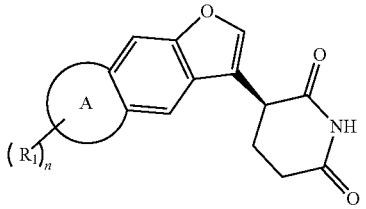

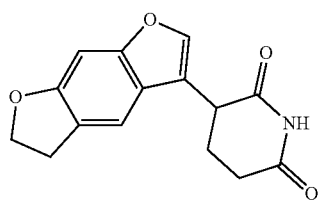

(I-2)

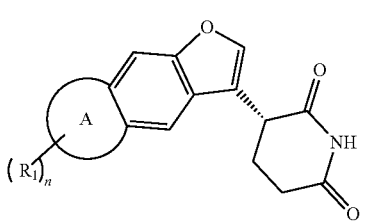

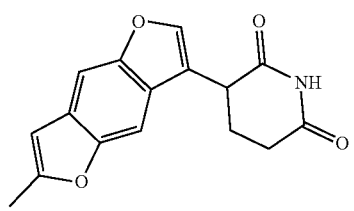

wherein, n, $R_1$ and ring A are as defined in the present disclosure.

Other solutions of the present disclosure are generated by any combination of the above variables.

The present disclosure also provides a compound or a pharmaceutically acceptable salt thereof, selected from

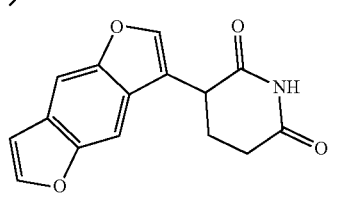

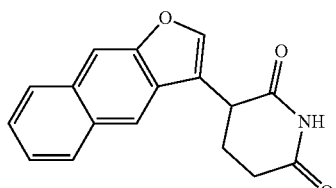

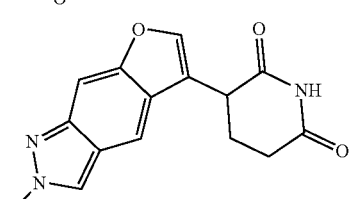

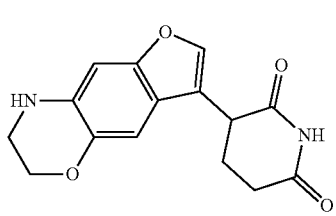 [SMILES: O=C1CCC(c2coc3cc4ccccc4cc23)C(=O)N1]

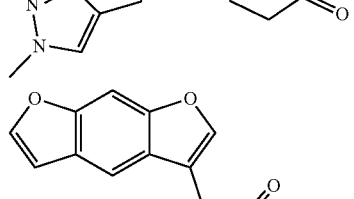

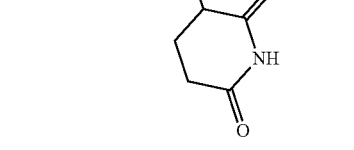

13
-continued
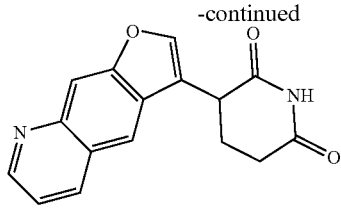
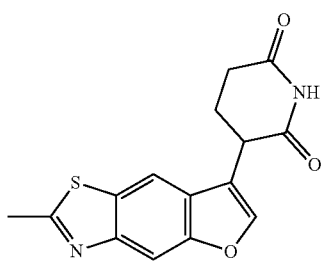 [SMILES: Cc1nc2cc3occ(C4CCC(=O)NC4=O)c3cc2s1]
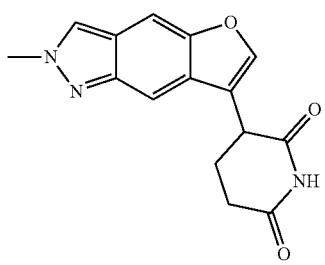 [SMILES: Cn1cc2cc3occ(C4CCC(=O)NC4=O)c3cc2n1]
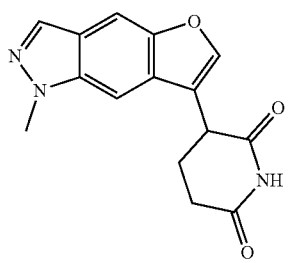 [SMILES: Cn1ncc2cc3occ(C4CCC(=O)NC4=O)c3cc21]
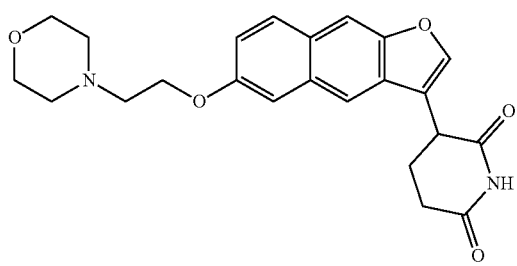
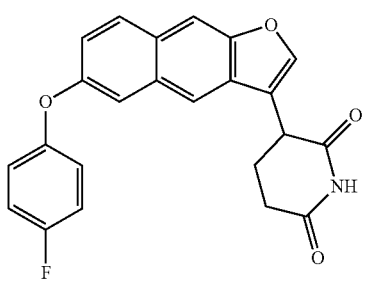
14
-continued
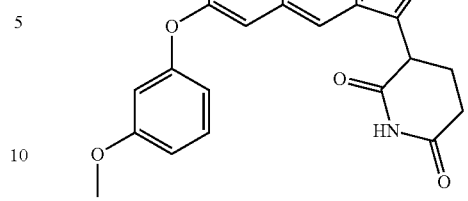
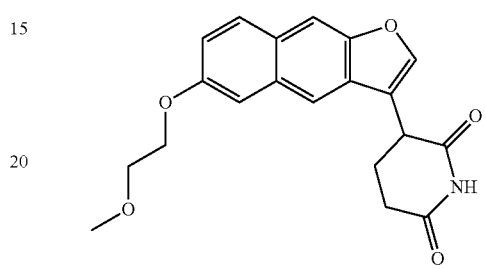
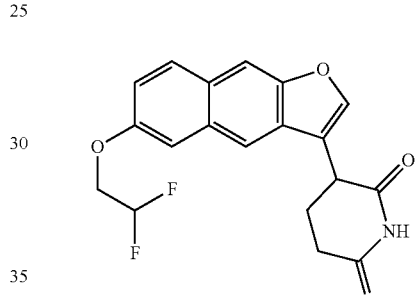
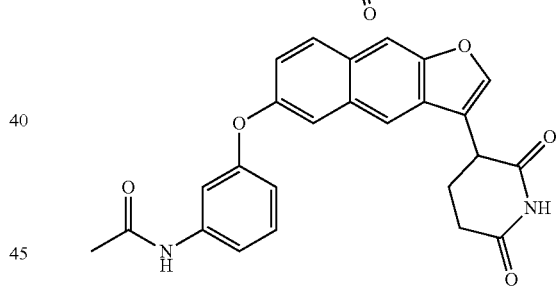
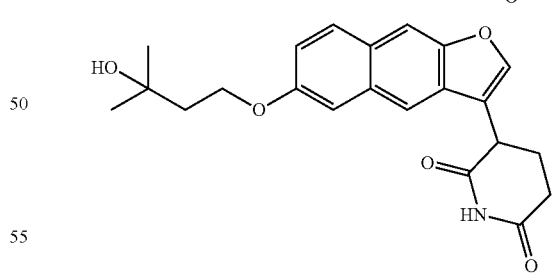
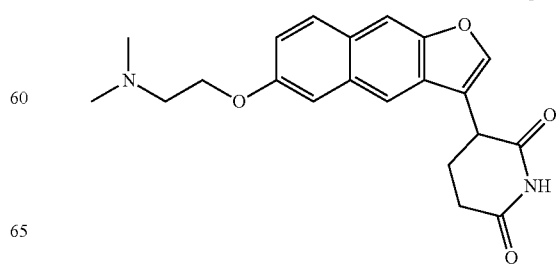

15
-continued
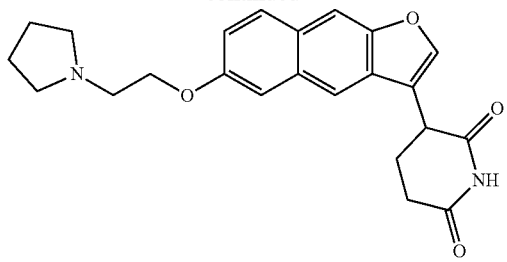
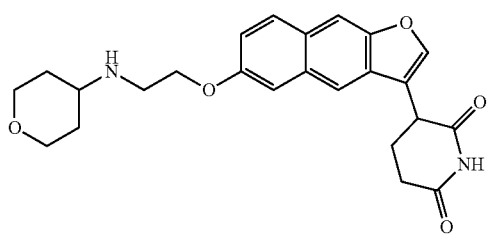
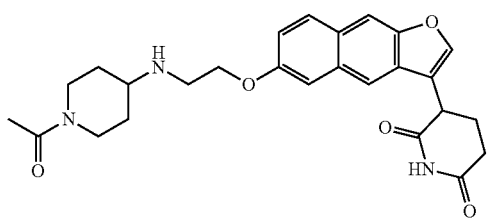
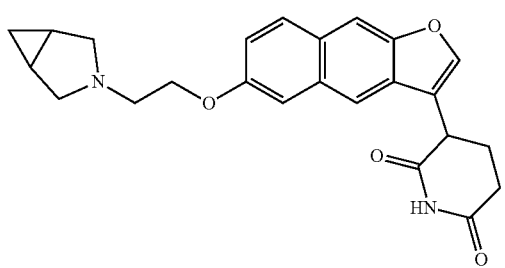
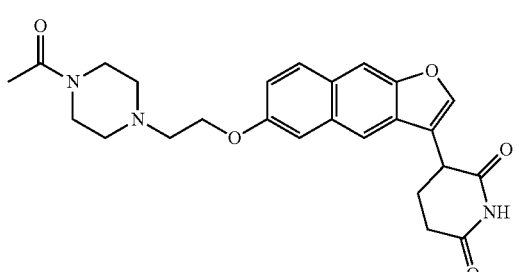
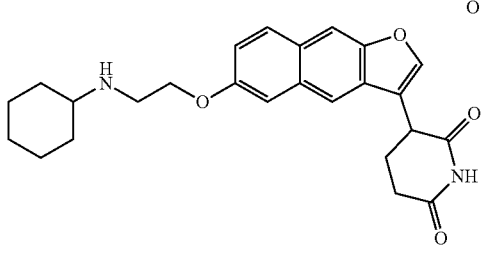
16
-continued
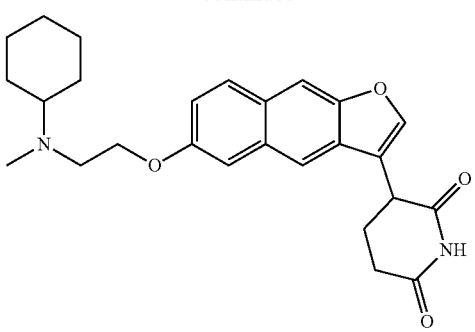
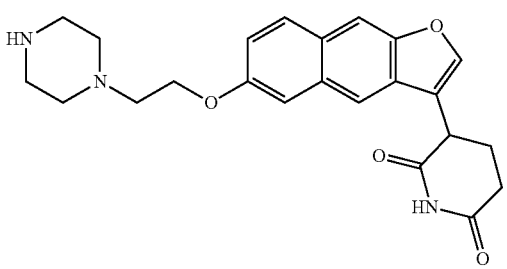
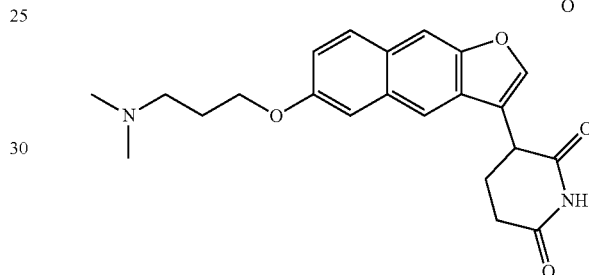
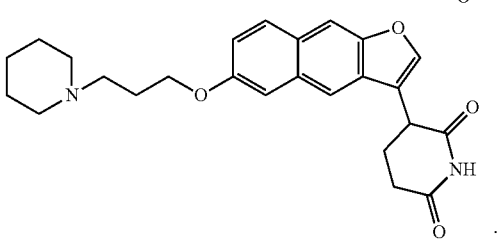
In some embodiments of the present disclosure, the above-mentioned compound or a pharmaceutically acceptable salt thereof is selected from
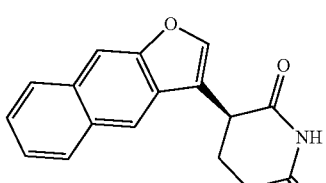
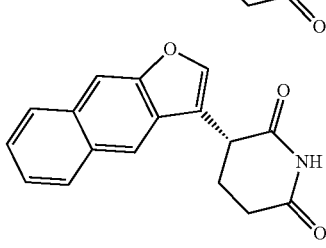

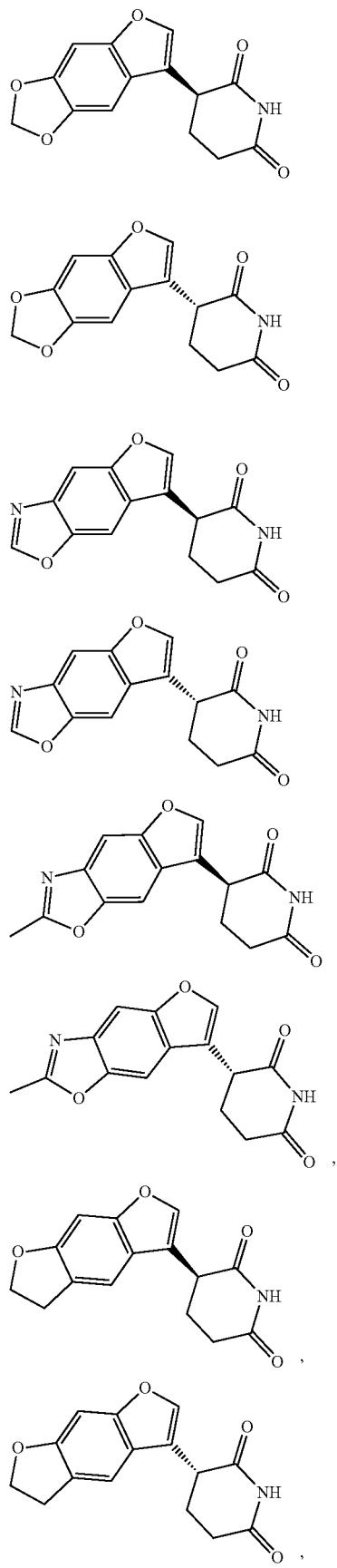
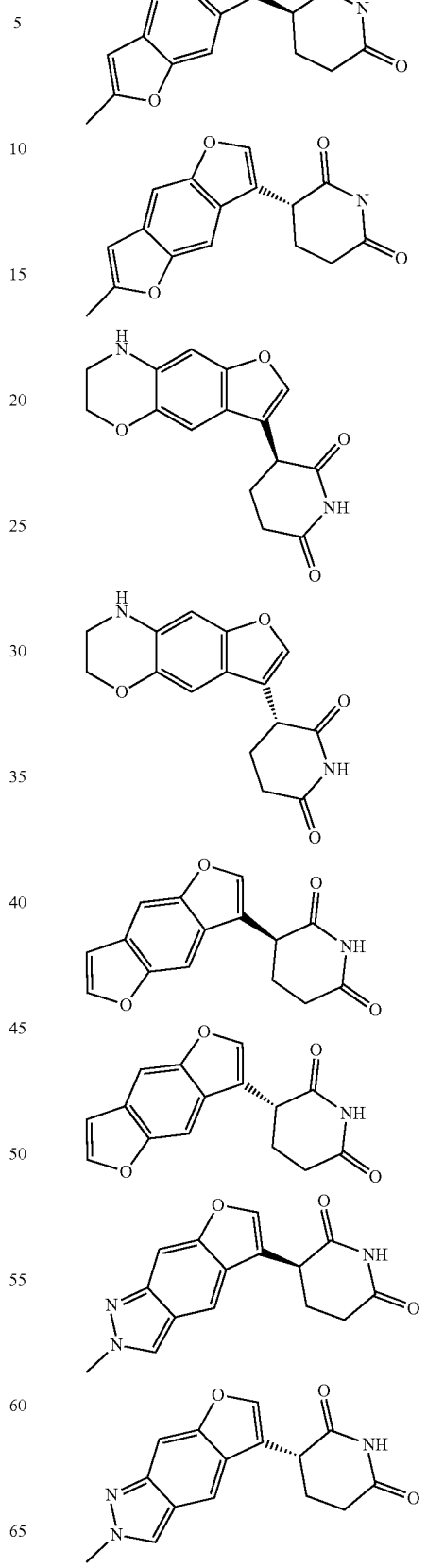

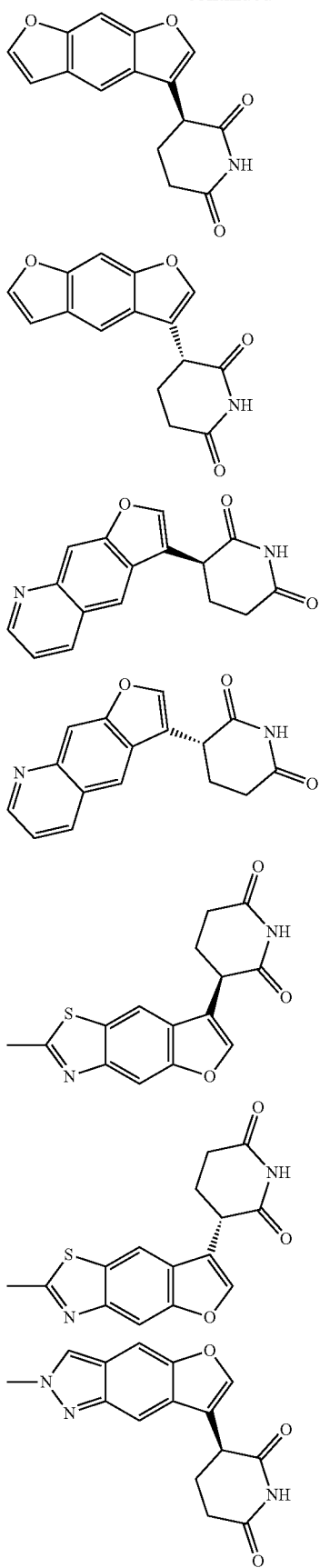
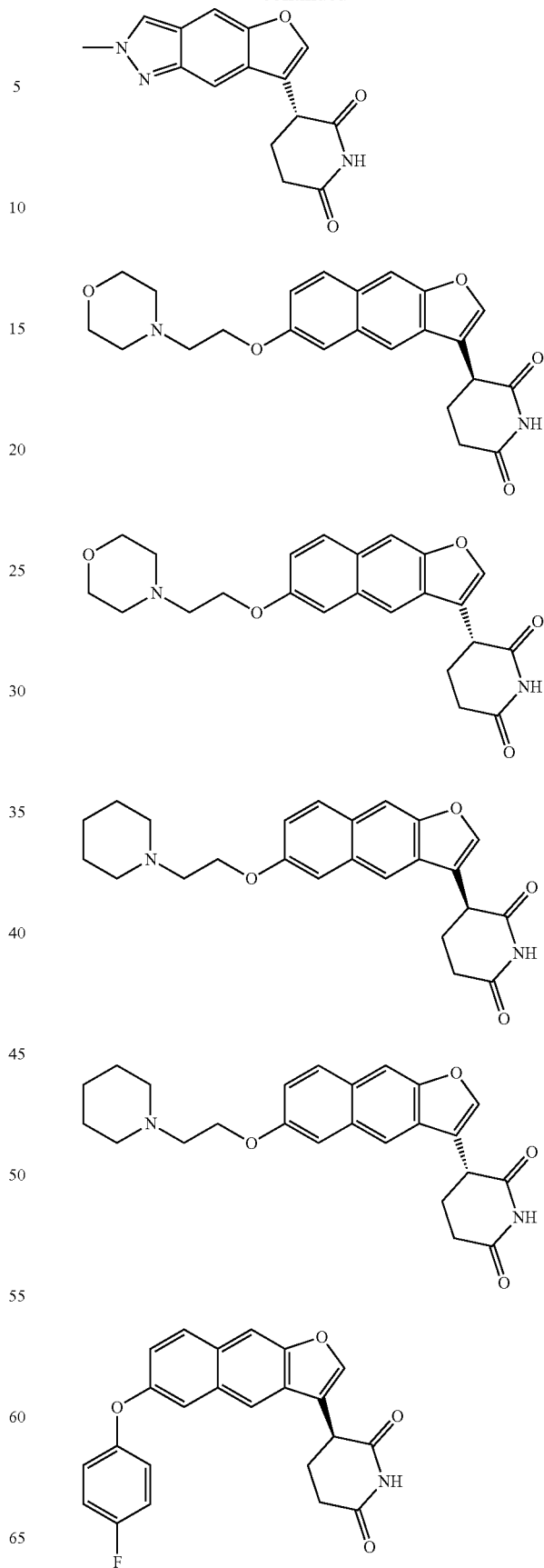

21
-continued
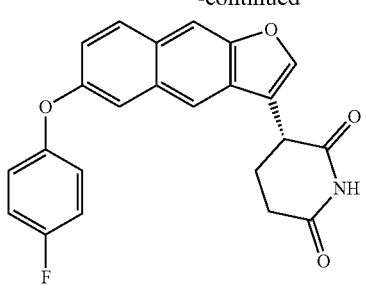
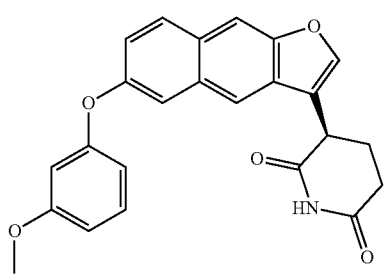
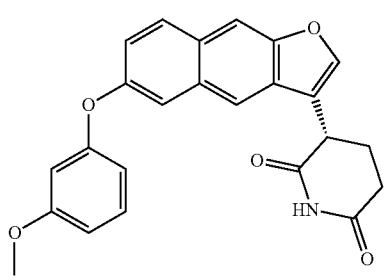
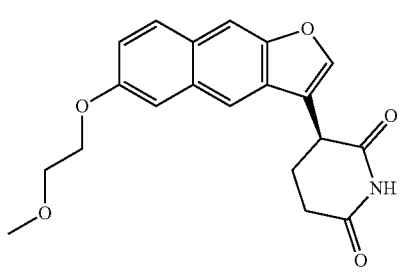
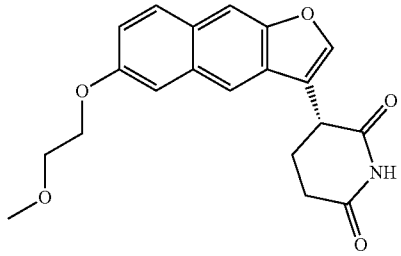
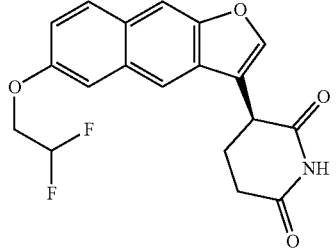
22
-continued
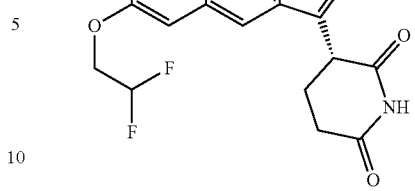
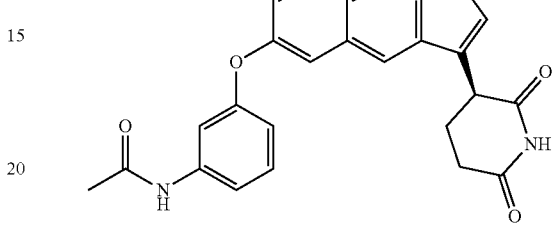
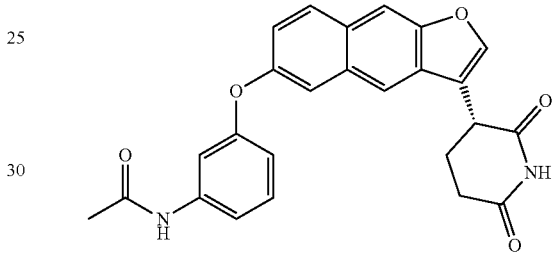
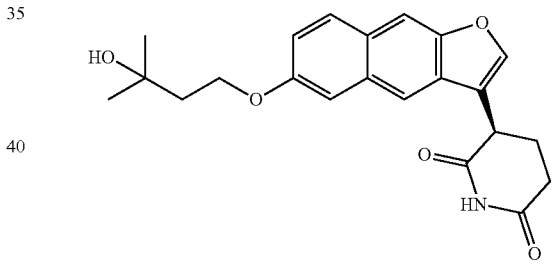
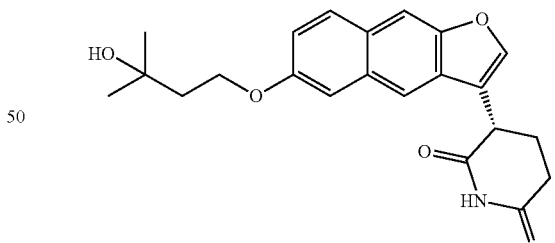
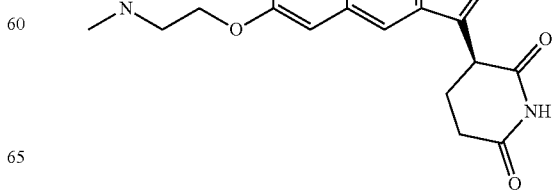

23
-continued
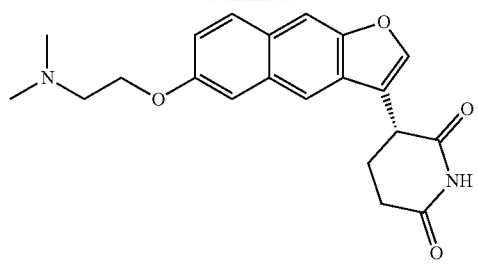
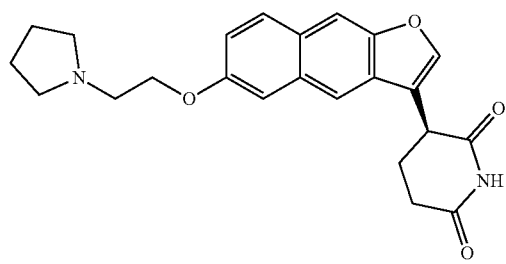
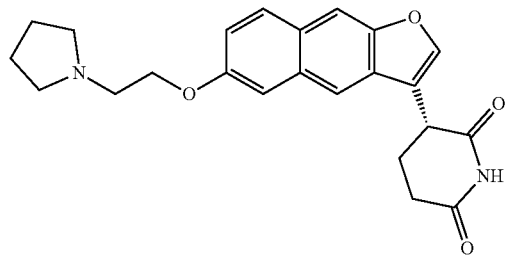
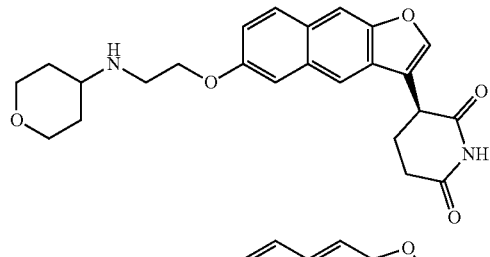
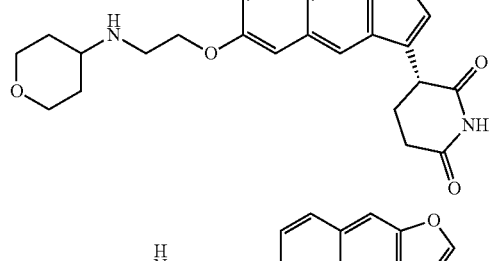
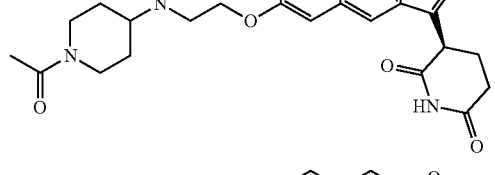
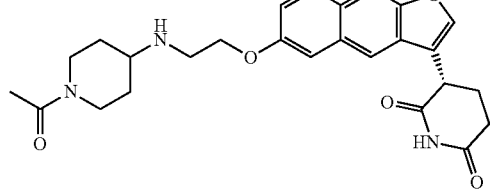
24
-continued
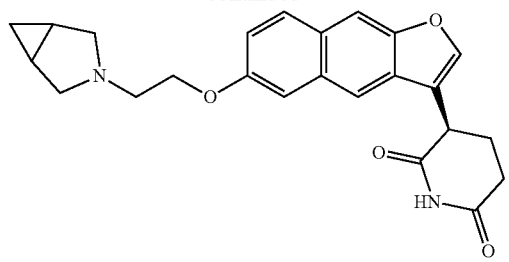
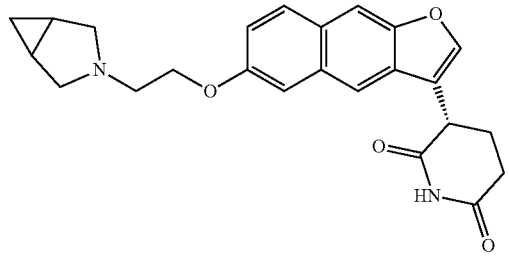
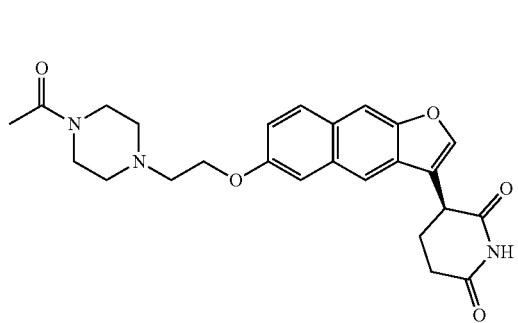
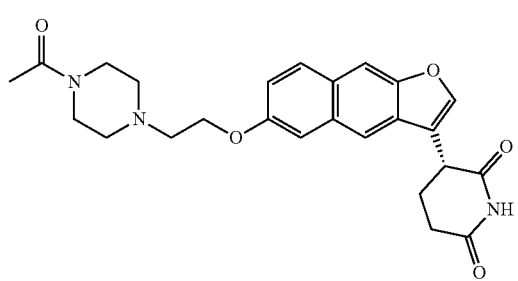
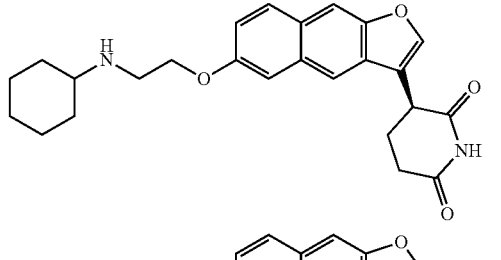
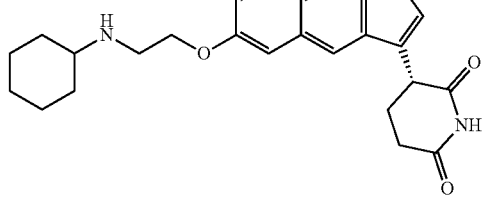

-continued

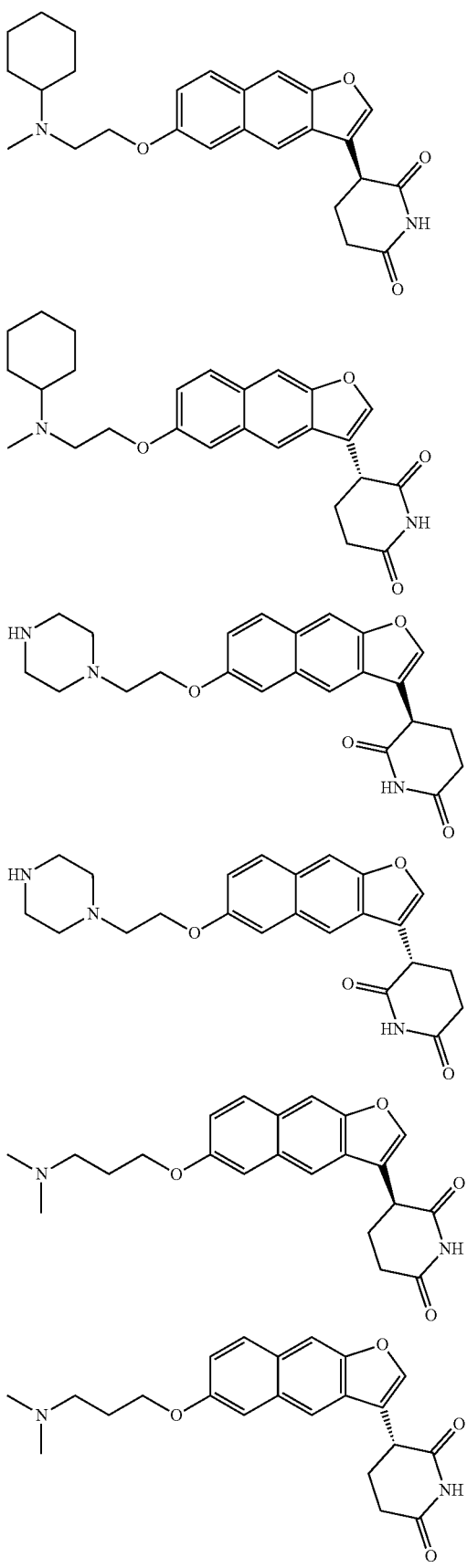

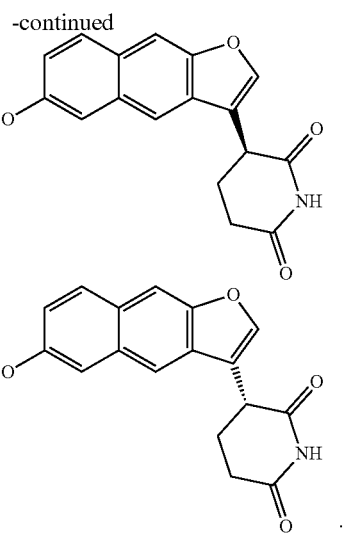

The present disclosure also provides a pharmaceutical composition, comprising a therapeutically effective amount of the above-mentioned compound or a pharmaceutically acceptable salt thereof as an active ingredient and a pharmaceutically acceptable carrier.

The present disclosure also provides the use of the above-mentioned compound or a pharmaceutically acceptable salt thereof in the preparation of a drug for treating a disease related to CRBN protein.

The present disclosure also provides the use of the above-mentioned composition in the preparation of a drug for treating a disease related to CRBN protein.

DEFINITION AND DESCRIPTION

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof.

The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present disclosure, which is prepared from the compound having specific substituents found in the present disclosure with relatively non-toxic acids or bases. When compounds of the present disclosure contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present disclosure contain relatively basic functional groups, acid addition salts can be obtained by contacting the neutral form of such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and also include salts of amino acids (such as arginine), and salts of organic acids such as glucuronic acid. Certain specific compounds of the present disclosure contain basic and acidic functional groups and thus can be converted to any base or acid addition salt.

The pharmaceutically acceptable salts of the present disclosure can be synthesized from a parent compound containing acid radicals or base radicals by conventional chemical methods. In general, the method for preparing such salts comprises: in water or an organic solvent or a mixture of both, reacting these compounds in free acid or base forms with a stoichiometric amount of a suitable base or acid to prepare the salts.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present disclosure. Additional asymmetric carbon atoms may be present in a substituent such as an alkyl group. All these isomers and mixtures thereof are included in the scope of the present disclosure.

Unless otherwise stated, the term "enantiomer" or "optical isomers" refers to stereoisomers that are mirror images of each other.

Unless otherwise stated, the term "diastereomers" refers to stereoisomers in which molecules have two or more chiral centers and are not mirror images of each other.

Unless otherwise stated, "(+)" represents right-handed, "(−)" represents left-handed, and "(±)" means racemic.

Unless otherwise stated, the wedge-shaped solid bond ($\nearrow$) and the wedge-shaped dotted bond ($\cdots$) represent the absolute configuration of a stereoscopic center; the straight solid bond ($\nearrow$) and straight dotted bond ($\cdots$) represent the relative configuration of a stereoscopic center; the wavy line ($\sim$) represents the wedge-shaped solid bond ($\nearrow$) or the wedge-shaped dotted bond ($\cdots$) or the wavy line ($\sim$) represents the straight solid bond ($\nearrow$) and the straight dotted bond ($\cdots$).

The compounds of the present disclosure may exist in specific. Unless otherwise stated, the term "tautomer" or "tautomeric form" means that at room temperature, isomers with different functional groups are in dynamic equilibrium and can be quickly converted to each other. Where tautomerization is possible (such as in solution), a chemical equilibrium of tautomers can be achieved. For example, proton tautomers (also known as prototropic tautomers) include interconversion via migration of a proton, such as keto-enol isomerization and imine-enamine isomerization. Valence tautomers include some interconversions by recombination of some of bond-forming electrons. A specific example of keto-enol tautomerization is the interconversion between two tautomers, pentane-2,4-dione and 4-hydroxypent-3-en-2-one.

Unless otherwise stated, the terms "rich in one isomer", "isomer enriched", "rich in one enantiomer" or "enantiomerically enriched" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomers and D and L isomers can be prepared using chiral synthesis or chiral reagents or other conventional techniques. If a particular enantiomer of a compound of the present disclosure is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines).

The compounds of the present disclosure may contain unnatural proportions of atomic isotopes at one or more of the atoms constituting the compound. For example, the compounds may be radiolabeled with radioactive isotopes, such as tritium ($^3$H), iodine-125 ($^{125}$I) or C-14 ($^{14}$C). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present disclosure, whether radioactive or not, are intended to be encompassed within the scope of the present disclosure. "Optional" or "optionally" means that the subsequently described event or circumstance may, but not necessarily occur, and that the description includes instances where said event or circumstance occurs and instances where said event or circumstance does not occur.

The term "substituted" means that any one or more hydrogen atoms on the designated atom is substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups. The term "optionally substituted" means that it may or may not be substituted. Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2 R, the group can optionally be substituted with up to two R, and R in each case has independent options. In addition, combinations of substituents and/or variants thereof are permissible only if such combinations result in stable compounds.

When the number of a linking group is 0, such as —(CRR)$_0$—, it means that the linking group is a single bond.

When a substituent is vacant, it means that the substituent does not exist. For example, when X is vacant in A-X, it means that the structure is actually A. When the substituents listed do not indicate through which atom they are connected to the substituted group, such substituents can be bonded through any of the atoms thereof, for example, pyridyl as a substituent can be attached to the substituted group via any carbon atom on the pyridine ring.

Unless otherwise specified, the number of atoms in a ring is usually defined as the member number of the ring. For example, "5- to 7-membered ring" means a "ring" with 5-7 atoms arranging in a circle.

Unless otherwise specified, the term "$C_{1-10}$alkyl" is used to mean a linear or branched saturated hydrocarbon group consisting of 1 to 10 carbon atoms. The $C_{1-10}$alkyl includes $C_{1-6}$, $C_{1-5}$, $C_{1-4}$, $C_{1-3}$, $C_{1-2}$, $C_{2-6}$, $C_{2-4}$, $C_8$, $C_7$, $C_6$ and $C_5$alkyl, etc.; It can be monovalent (such as methyl), divalent (such as methyl) or multivalent (such as methine). Examples of $C_{1-10}$alkyl include, but are not limited to methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, heptyl, octyl, etc.

Unless otherwise specified, the term "$C_{1-6}$ alkyl" is used to represent a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl; It can be monovalent (such as methyl), divalent (such as methyl) or multivalent (such as methine). Examples of $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl) and hexyl.

Unless otherwise specified, the term "$C_{1-3}$ alkyl" is used to represent a linear or branched saturated hydrocarbon group consisting of 1 to 3 carbon atoms. The $C_{1-3}$ alkyl includes $C_{1-2}$ and $C_{2-3}$ alkyl; It can be monovalent (such as methyl), divalent (such as methyl) or multivalent (such as methine). Examples of $C_{1-3}$ alkyl include, but are not limited to, methyl (Me), ethyl (Et) and propyl (including n-propyl and isopropyl).

Unless otherwise specified, the term "$C_{1-10}$ alkoxy" means those alkyl groups containing 1 to 10 carbon atoms that are connected to the rest of the molecule through one oxygen atom. The $C_{1-10}$ alkoxy group includes $C_{1-9}$, $C_{1-8}$, $C_{1-7}$, $C_{1-6}$, $C_{1-5}$, $C_{1-4}$, $C_{1-3}$, $C_{1-2}$, $C_{2-6}$, $C_{2-4}$, $C_6$, $C_5$, $C_4$, $C_3$ alkoxy, etc. Examples of $C_{1-10}$ alkoxy include but are not limited to methoxy, ethoxy, propoxy (including n-propoxy and isopropoxy), butoxy (including n-butoxy, isobutoxy, s-butoxy and t-butoxy), pentyloxy (including n-pentyloxy, isopentyloxy and neopentyloxy), hexyloxy, etc.

Unless otherwise specified, the term "$C_{1-6}$ alkoxy" means those alkyl groups containing 1 to 6 carbon atoms that are connected to the rest of the molecule through one oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$, $C_3$ alkoxy, etc. Examples of $C_{1-6}$ alkoxy include but are not limited to methoxy, ethoxy, propoxy (including n-propoxy and isopropoxy), butoxy (including n-butoxy, isobutoxy, s-butoxy and t-butoxy), pentyloxy (including n-pentyloxy, isopentyloxy and neopentyloxy), hexyloxy, etc.

Unless otherwise specified, the term "$C_{1-3}$ alkoxy" means those alkyl groups containing 1 to 3 carbon atoms that are connected to the rest of the molecule through one oxygen atom. The $C_{1-3}$ alkoxy group includes $C_{1-2}$, $C_{2-3}$, $C_3$, $C_2$ alkoxy, etc. Examples of $C_{1-3}$ alkoxy include but are not limited to methoxy, ethoxy, propoxy (including n-propoxy and isopropoxy), etc.

Unless otherwise specified, the term "$C_{1-10}$ alkylamino" means those alkyl groups containing 1 to 6 carbon atoms that are connected to the rest of the molecule through an amino group. The $C_{1-6}$ alkylamino includes $C_{1-10}$ alkoxy including $C_{1-9}$, $C_{1-8}$, $C_{1-7}$, $C_{1-6}$, $C_{1-5}$, $C_{1-4}$, $C_{1-3}$, $C_{1-2}$, $C_{2-6}$, $C_{2-4}$, $C_6$, $C_5$, $C_4$, $C_2$ alkylamino, etc. Examples of $C_{1-6}$ alkylamino include, but are not limited to —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, etc.

Unless otherwise specified, the term "$C_{1-6}$ alkylamino" means those alkyl groups containing 1 to 6 carbon atoms that are connected to the rest of the molecule through an amino group. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$, $C_2$ alkylamino, etc. Examples of $C_{1-6}$ alkylamino include, but are not limited to —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, etc.

Unless otherwise specified, the term "halo" or "halogen" by itself or as part of another substituent means a fluorine, chlorine, bromine or iodine atom.

Unless otherwise specified, "$C_{4-6}$ cycloalkyl" means a saturated cyclic hydrocarbon group consisting of 4 to 6 carbon atoms, which comprises a monocyclic and bicyclic ring system, wherein the bicyclic ring system includes a spiro ring, a fused ring and a bridged ring and the $C_{4-6}$ cycloalkyl includes $C_{4-5}$, $C_{5-6}$ cycloalkyl, etc.; It can be monovalent, bivalent or multivalent. Examples of $C_{3-6}$ cycloalkyl include, but are not limited to, cyclopropyl, cyclobutyl, cyclopentyl and cyclohexyl.

Unless otherwise specified, the term "5- to 10-membered heterocycloalkyl" by itself or in combination with other terms respectively represents a saturated cyclic group consisting of 5 to 10 ring atoms, of which 1, 2, 3 or 4 ring atoms are heteroatoms independently selected from O, S and N, and the rest of which are carbon atoms, wherein the nitrogen atom is optionally quaternized, and the nitrogen and sulfur heteroatoms can be optionally oxidized (i.e., NO and S(O)$_p$, wherein p is 1 or 2). It comprises a monocyclic, bicyclic and tricyclic ring system, wherein the bicyclic and tricyclic system include a spiro ring, a fused ring, and a bridged ring. In addition, in terms of the "5- to 10-membered heterocycloalkyl", the heteroatom may occupy the connection position of the heterocycloalkyl to the remainder of the molecule. The 5- to 10-membered heterocycloalkyl includes 5- to 8-membered, 5- to 6-membered, 5- to 7-membered, 5- to 9-membered, 4-membered, 5-membered and 6-membered heterocycloalkyl, etc. Examples of 5- to 10-membered heterocycloalkyl include, but are not limited to pyrrolidinyl, pyrazolidinyl, imidazolidinyl, tetrahydrothienyl (including tetrahydrothiophene-2-yl and tetrahydrothiophene-3-yl), tetrahydrofuryl (including tetrahydrofuran-2-yl), tetrahydropyranyl, piperidinyl (including 1-piperidinyl, 2-piperidinyl and 3-piperidinyl), piperazinyl (including 1-piperazinyl and 2-piperazinyl), morpholinyl (including 3-morpholinyl and 4-morpholinyl), dioxanyl, dithianyl, isoxazolidine, isothiazolidine, 1,2-oxazinyl, 1,2-thiazinyl, hexahydropyridazinyl, homopiperazinyl, homopiperidinyl or dioxepanyl.

Unless otherwise specified, the term "5- to 8-membered heterocycloalkyl" by itself or in combination with other terms respectively represents a saturated cyclic group consisting of 5 to 8 ring atoms, of which 1, 2, 3 or 4 ring atoms are heteroatoms independently selected from O, S and N, and the rest of which are carbon atoms, wherein the nitrogen atom is optionally quaternized, and the nitrogen and sulfur heteroatoms can be optionally oxidized (i.e., NO and $S(O)_p$, wherein p is 1 or 2). It comprises a monocyclic and bicyclic ring system, wherein the bicyclic system includes a spiro ring, a fused ring, and a bridged ring. In addition, in terms of the "5- to 8-membered heterocycloalkyl", the heteroatom may occupy the connection position of the heterocycloalkyl to the remainder of the molecule. The 5- to 8-membered heterocycloalkyl include 5- to 6-membered, 5- to 6-membered, 5- to 7-membered, 8-membered, 5-membered and 6-membered heterocycloalkyl, etc. Examples of 3- to 8-membered heterocycloalkyl include, but are not limited to pyrrolidinyl, pyrazolidinyl, imidazolidinyl, tetrahydrothienyl (including tetrahydrothiophene-2-yl and tetrahydrothiophene-3-yl), tetrahydrofuryl (including tetrahydrofuran-2-yl), tetrahydropyranyl, piperidinyl (including 1-piperidinyl, 2-piperidinyl and 3-piperidinyl), piperazinyl (including 1-piperazinyl and 2-piperazinyl), morpholinyl (including 3-morpholinyl and 4-morpholinyl), dioxanyl, dithianyl, isoxazolidine, isothiazolidine, 1,2-oxazinyl, 1,2-thiazinyl, hexahydropyridazinyl, homopiperazinyl, homopiperidinyl or dioxepanyl.

Unless otherwise specified, "$C_{4-6}$ cycloalkyl" means a saturated cyclic hydrocarbon group consisting of 4 to 6 carbon atoms, which comprises a monocyclic and bicyclic ring system, and the $C_{4-6}$ cycloalkyl includes $C_{4-5}$ and $C_{5-6}$ cycloalkyl, etc.; It can be monovalent, bivalent or multivalent. Examples of $C_{3-6}$ cycloalkyl include, but are not limited to, cyclobutyl, cyclopentyl and cyclohexyl, etc.

Unless otherwise specified, the term "4- to 7-membered heterocycloalkyl" by itself or in combination with other terms respectively represents a saturated cyclic group consisting of 4 to 7 ring atoms, of which 1, 2, 3 or 4 ring atoms are heteroatoms independently selected from O, S and N, and the rest of which are carbon atoms, wherein the nitrogen atom is optionally quaternized, and the nitrogen and sulfur heteroatoms can be optionally oxidized (i.e., NO and $S(O)_p$, wherein p is 1 or 2). It comprises a monocyclic and bicyclic ring system, wherein the bicyclic system includes a spiro ring, a fused ring, and a bridged ring. In addition, in terms of the "4- to 7-membered heterocycloalkyl", the heteroatom may occupy the connection position of the heterocycloalkyl to the remainder of the molecule. The 4- to 7-membered heterocycloalkyl includes 4- to 5-membered, 4- to 6-membered, 5- to 6-membered, 5- to 7-membered, 4-membered, 5-membered and 6-membered heterocycloalkyl group, etc. Examples of 4- to 7-membered heterocycloalkyl include, but are not limited to, azetidinyl, oxetanyl, thiatanyl, pyrrolidinyl, pyrazolidinyl, imidazolidinyl, tetrahydrothienyl (including tetrahydrothiophene-2-yl and tetrahydrothiophen-3-yl), tetrahydrofuranyl (including tetrahydrofuran-2-yl), tetrahydropyranyl, piperidinyl (including 1-piperidinyl, 2-piperidinyl and 3-piperidinyl), piperazinyl (including 1-piperazinyl and 2-piperazinyl), morpholinyl (including 3-morpholinyl and 4-morpholinyl), dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

Unless otherwise specified, the term "4- to 7-membered heterocycloalkenyl" by itself or in combination with other terms respectively represents a partially unsaturated cyclic group containing at least one carbon-carbon double bond and consisting of 4 to 7 ring atoms, of which 1, 2, 3 or 4 ring atoms are heteroatoms independently selected from O, S and N, and the rest of which are carbon atoms, wherein the nitrogen atom is optionally quaternized, and the nitrogen and sulfur heteroatoms can be optionally oxidized (i.e., NO and $S(O)_p$, wherein p is 1 or 2). It comprises a monocyclic ring system, a bicyclic ring system and a tricyclic ring system, wherein the bicyclic ring system and the tricyclic ring system include a spiro ring, a fused ring, and a bridged ring, and any ring in the systems is non-aromatic. In addition, in terms of the "4- to 7-membered heterocycloalkenyl", the heteroatom may occupy the connection position of the heterocycloalkenyl to the remainder of the molecule. The 4- to 7-membered heterocycloalkenyl includes 5- to 6-membered, 4- to 5-membered, 4-membered, 5-membered and 6-membered heterocycloalkenyl, etc. Examples of 4- to 7-membered heterocycloalkenyl include, but are not limited to

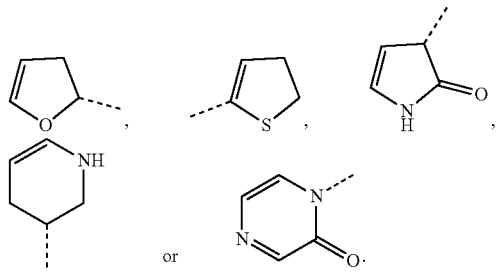

Unless otherwise specified, the terms "5- to 6-membered heteroaryl ring" and "5- to 6-membered heteroaryl" of the present disclosure can be used interchangeably, and the term "5- to 6-membered heteroaryl" represents a monocyclic group having a conjugated π-electron system and consisting of 5 to 6 ring atoms, of which 1, 2, 3, or 4 ring atoms are heteroatoms independently selected from O, S, and N, and the rest of which are carbon atoms, wherein nitrogen atoms are optionally quaternized, and nitrogen and sulfur heteroatoms can be optionally oxidized (i.e., NO and $S(O)_p$, wherein p is 1 or 2). The 5- to 6-membered heteroaryl can be connected to the remainder of the molecule via a heteroatom or a carbon atom. The 5- to 6-membered heteroaryl includes 5-membered and 6-membered heteroaryl. Examples of the 5- to 6-membered heteroaryl include, but are not limited to, pyrrolyl (including N-pyrrolyl, 2-pyrrolyl and 3-pyrrolyl), pyrazolyl (including 2-pyrazolyl and 3-pyrazolyl), imidazolyl (including N-imidazolyl, 2-imidazolyl, 4-imidazolyl and 5-imidazolyl), oxazolyl (including 2-oxazolyl, 4-oxazolyl and 5-oxazolyl), triazolyl (1H-1,2,3-triazolyl, 2H-1,2,3-triazolyl, 1H-1,2,4-triazolyl and 4H-1,2,4-triazolyl), tetrazolyl, isoxazolyl (3-isoxazolyl, 4-isoxazolyl and 5-isoxazolyl), thiazolyl (including 2-thiazolyl, 4-thiazolyl and 5-thiazolyl), furyl (including 2-furanyl and 3-furanyl), thienyl (including 2-thienyl and 3-thienyl), pyridyl (including 2-pyridyl, 3-pyridyl and 4-pyridyl), pyrazinyl or pyrimidinyl (including 2-pyrimidyl and 4-pyrimidyl).

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, and also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$; Similarly, n-membered to n+m-membered means that the number of atoms in the ring is n to n+m, for example, a 3- to 12-membered ring includes a 3-membered ring, a 4-membered ring, a 5-membered ring, a 6-membered ring, a 7-membered ring, a 8-membered ring, a 9-membered ring, a 10-membered ring, a 11-membered ring, and a 12-membered ring, and also includes any range from n to n+m, for example, a 3- to 12-membered ring includes a 3- to 6-membered ring, a 3- to 9-membered ring, a 5- to 6-membered ring, a 5- to 7-membered ring, a 6- to 7-membered ring, a 6- to 8-membered ring, and a 6- to 10-membered ring.

The term "leaving group" refers to a functional group or atom that can be substituted by another functional group or atom through a substitution reaction (e.g., an affinity substitution reaction). For example, representative leaving groups include trifluoromethanesulfonate; chlorine, bromine and iodine; sulfonates, such as methanesulfonate, tosylate, p-bromobenzenesulfonate, and p-toluenesulfonate; and acyloxy, such as acetoxy and trifluoroacetoxy.

The term "protecting group" includes, but is not limited to, "amino protecting group", "hydroxy protecting group" or "mercapto protecting group". The term "amino protecting group" refers to a protecting group suitable for preventing side reactions occur at the nitrogen atom of an amino group. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl)methyl; silyl, such as trimethylsilyl (TMS) and tert-butyldimethylsilyl (TBS). The term "hydroxyl protecting group" refers to a protecting group suitable for preventing side reactions of a hydroxyl group. Representative hydroxyl protecting groups include, but are not limited to: alkyl, such as methyl, ethyl and tert-butyl; acyl, such as alkanoyl (e.g., acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TB S).

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The solvents used in the present disclosure are commercially available. The present disclosure uses the following abbreviations: aq represents water; HATU represents O-(7-azabenzotriazol-1-yl)-N,N,N',N'-tetramethylurea hex afluoropho sphate; EDC represents N-(3-dimethylaminopropyl)-N'-ethylcarbodiimide hydrochloride; m-CPBA represents 3-chloroperoxybenzoic acid; eq represents equivalent; CDI represents carbonyldiimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amine protecting group; BOC represents tert-butoxycarbonyl, which is an amine protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; NFSI represents N-fluoro-N-(benzenesulfonyl)benzenesulfonamide; NCS represents 1-chloropyrroli dine-2,5-dione; n-$Bu_4NF$ represents tetrabutylammonium fluoride; iPrOH represents 2-propanol; mp represents melting point; LDA represents lithium diisopropylamide; M represents mol/L.

Compounds are named according to conventional naming principles in the field or using ChemDraw® software, and commercially available compounds are named using supplier catalog names.

TECHNICAL EFFECTS

After multiple myeloma cells MM.1S are treated with the compounds of the present disclosure at concentrations of 100 nM, or 500 nM and 50 nM, WB detection shows that the level of IKZF3 protein in the cells is significantly decreased; and the compound exhibits an excellent inhibitory effect on cell proliferation in lymphoma cell lines such as OCI-LY10, DOHH2 and Mino. The oral plasma system exposure of the compound of the present disclosure is relatively high. In rodent mice, the pharmacokinetic properties of the compound of the present disclosure are very good. The compound of the present disclosure exhibits a significant tumor-shrinking effect in a human in vivo pharmacodynamic model of lymphoma OCI-LY10.

BRIEF DESCRIPTION OF THE DRAWINGS

FIG. 1 shows changes of IKZF3 protein levels detected by WB in multiple myeloma cells MM.1S treated with the compound of the present disclosure at a concentration of 100 nM, 500 nM, or 50 nM.

DETAILED DESCRIPTION OF THE PREFERRED EMBODIMENT

The present disclosure will be described in detail with the following examples, but not imply any adverse limitation to the present disclosure. The present disclosure has been described in detail herein, and the specific embodiments thereof are also disclosed therein. For a person skilled in the art, without departing from the spirit and scope of the present disclosure, all the variations and improvements made to the specific embodiments of the present disclosure would have been obvious.

Example 1

WX001

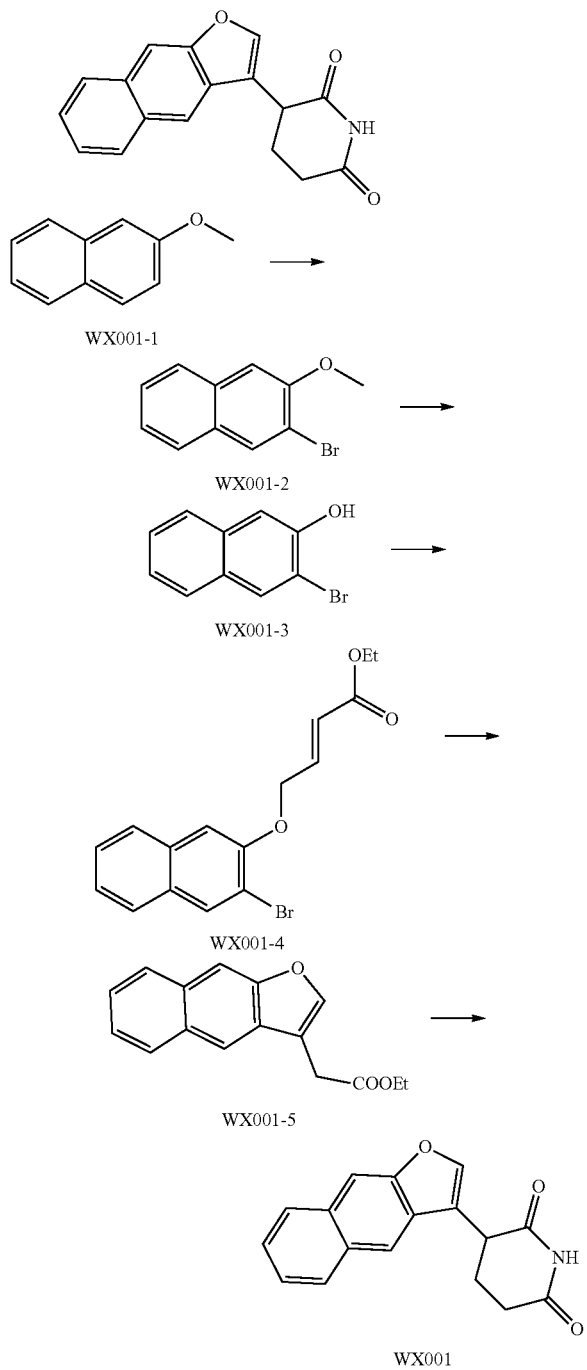

Step 1: Synthesis of Intermediate WX001-2

At −78° C. and under nitrogen atmosphere, n-butyllithium (2.5 M, 27.23 mL, 2.5 M dissolved in n-hexane) was added dropwise to a solution of WX001-1 (10.16 g, 64.22 mmol) in tetrahydrofuran (100 mL); and the reaction mixture was stirred at 20° C. for 1 hour, and then cooled to −78° C. 1,2-Dichloroethane (13.27 g, 70.65 mmol, 28.01 mL) was added, and the reaction mixture was stirred and reacted at 20° C. for 14 hours. After completion of the reaction, the reaction mixture was quenched with a saturated ammonium chloride solution (100 mL) and extracted with ethyl acetate (100 mL×3). The organic phase was combined, washed with brine (200 mL×2), dried over anhydrous sodium sulfate and filtered; and the solvent was removed from the filtrate under reduced pressure. The resulting residue was purified by column chromatography (eluent: petroleum ether/ethyl acetate=1/0-100/1, volume ratio) to obtain intermediate WX001-2. $^1$H NMR (400 MHz, CDCl$_3$) δ: 8.08 (s, 1H), 7.75-7.69 (m, 2H), 7.50-7.46 (m, 1H), 7.40-7.36 (m, 1H), 7.17-7.15 (m, 1H), 4.02 (s, 3H).

Step 2: Synthesis of Intermediate WX001-3

At −78° C. and under nitrogen atmosphere, boron tribromide (63.43 g, 253.19 mmol, 24.40 mL) was added dropwise to a solution of intermediate WX001-2 (20.01 g, 84.40 mmol) in dichloromethane (120 mL); and the reaction mixture was slowly warmed to 20° C., and stirred and reacted at 20° C. for 2 hours. After completion of the reaction, the reaction mixture was slowly added dropwise to ice water (400 mL), and extraction with dichloromethane (300 mL×3) was performed. The organic phase was combined, washed with brine (300 mL×2), dried over anhydrous sodium sulfate and filtered; and the solvent was removed from the filtrate under reduced pressure. The resulting residue was purified by column chromatography (eluent: petroleum ether/ethyl acetate=100/1-50/1, volume ratio) to obtain intermediate WX001-3. $^1$H NMR (400 MHz, CDCl$_3$) δ: 8.04 (s, 1H), 7.70 (d, J=8.8 Hz, 2H), 7.46 (td, J=1.0, 7.4 Hz, 1H), 7.40 (s, 1H), 7.36 (td, J=1.2, 7.6 Hz, 1H), 5.68 (s, 1H).

Step 3: Synthesis of Intermediate WX001-4

At 20° C. and under nitrogen atmosphere, intermediate WX001-3 (20.67 g, 92.66 mmol) was dissolved in acetonitrile (250 mL), and then potassium carbonate (25.61 g, 185.33 mmol) and ethyl 4-bromocrotonate (35.78 g, 185.33 mmol, 25.55 mL) were added; and the reaction mixture was stirred and reacted at 20° C. for 16 hours. After completion of the reaction, water (300 mL) was added and extraction with ethyl acetate (200 mL×3) was performed. The organic phase was combined, washed with saturated brine (300 mL×2), dried over anhydrous sodium sulfate and filtered; and the solvent was removed from the filtrate under reduced pressure. The resulting residue was purified by column chromatography (eluent: petroleum ether/ethyl acetate=100/1-50/1, volume ratio) to obtain intermediate WX001-4. MS-ESI m/z: 334.8 [M+H]$^+$, 336.8 [M+H+2]$^+$.

Step 4: Synthesis of Intermediate WX001-5

At room temperature and under nitrogen atmosphere, intermediate WX001-4 (44.87 g, 116.60 mmol, purity: 87.10%) was dissolved in N,N-dimethylformamide (300 mL), and then sodium carbonate (30.89 g, 291.49 mmol), sodium formate (7.93 g, 116.60 mmol, 6.29 mL), palladium acetate (1.31 g, 5.83 mmol) and tetrabutylammonium chloride (35.64 g, 128.25 mmol, 35.86 mL) were added successively; and the reaction mixture was heated to 80° C. and stirred and reacted for 14 hours. After completion of the reaction, the reaction mixture was cooled to room temperature, added water (500 mL) and extracted with ethyl acetate (300 mL×3). The organic phase was combined, washed with saturated brine (600 mL×2), dried over anhydrous sodium sulfate and filtered; and the solvent was removed from the filtrate under reduced pressure. The resulting residue was purified by column chromatography (eluent: petroleum ether/ethyl acetate=100/1-50/1, volume ratio) to obtain intermediate WX001-5. $^1$H NMR (400 MHz, CDCl$_3$) δ: 8.04

(s, 1H), 7.99-7.92 (m, 2H), 7.90 (s, 1H), 7.76 (s, 1H), 7.47-7.44 (m, 2H), 4.23 (q, J=7.2 Hz, 2H), 3.80 (d, J=1.2 Hz, 2H), 1.30 (t, J=7.2 Hz, 3H).

Step 5: Synthesis of Compound WX001

At 0° C. and under nitrogen atmosphere, intermediate WX001-5 (5.24 g, 20.61 mmol) was dissolved in N,N-dimethylformamide (40 mL), and then potassium tert-butoxide (2.31 g, 20.61 mmol) was added; at 0° C., the mixture was stirred for 0.5 hours and then acrylamide (1.46 g, 20.61 mmol) was added; at 0° C. and under nitrogen atmosphere, the reaction mixture was stirred and reacted for additional 1 hour. After completion of the reaction, water (50 mL) was added and extraction with ethyl acetate (50 mL×3) was performed. The organic phase was combined, washed with saturated brine (100 mL×2), dried over anhydrous sodium sulfate and filtered; and the solvent was removed from the filtrate under reduced pressure. The resulting residue was slurried with methanol (20 mL), stirred at 20° C. for 2 hours and then filtered; the filter cake was rinsed with methanol (5 mL) and collected to obtain target compound WX001. MS-ESI m/z: 280.0 [M+H]+. 1H NMR (400 MHz, DMSO_d6) δ: 10.97 (s, 1H), 8.15 (s, 1H), 8.08 (s, 1H), 8.05 (s, 1H), 8.03-7.99 (m, 2H), 7.50-7.42 (m, 2H), 4.25 (dd, 12.0 Hz, 1H), 2.84-2.76 (m, 1H), 2.67-2.59 (m, 1H), 2.48-2.41 (m, 1H), 2.21-2.13 (m, 1H).

Example 1a

WX001

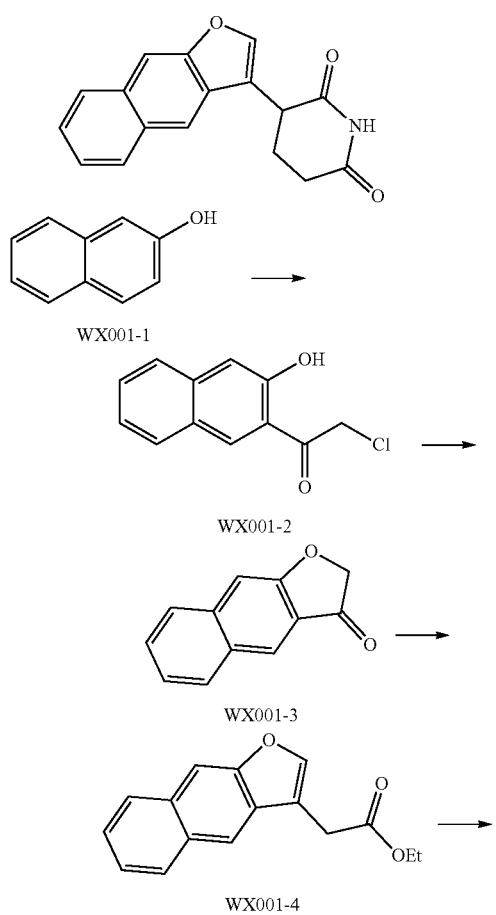

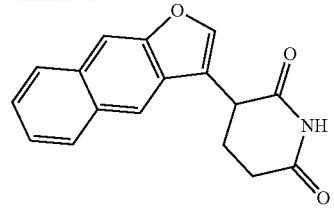

Step 1: Synthesis of Intermediate WX001-2

At 0° C., to a solution of boron trichloride in dichloromethane (1 M, 16.56 mL), a solution of WX001-1 (1.99 g, 13.80 mmol) in dichloromethane (20 mL) was slowly added dropwise; under nitrogen atmosphere, the reaction mixture was stirred and reacted at 0° C. for 0.5 hour, and then chloroacetonitrile (1.25 g, 16.56 mmol, 1.05 mL) was slowly added dropwise; and the reaction mixture was stirred and reacted at 0° C. for additional 0.5 hours. Finally, aluminum trichloride (920.26 mg, 6.90 mmol) was added; and the reaction mixture was warmed to room temperature and stirred and reacted for additional 3 hours. After completion of the reaction, the reaction mixture was poured into ice water (50 mL) and extracted with dichloromethane (30 mL×3). The organic phase was combined, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=50/1-20/1, volume ratio) to obtain target intermediate WX001-2. 1H NMR (400 MHz, CDCl3) δ: 8.69 (d, J=8.4 Hz, 1H), 8.01 (d, J=8.8 Hz, 1H), 7.77 (d, J=8.0 Hz, 1H), 7.60 (td, J=0.8, 8.0 Hz, 1H), 7.42 (td, J=1.2, 8.0 Hz, 1H), 7.20 (d, J=9.6 Hz, 1H), 4.69 (s, 2H).

Step 2: Synthesis of Intermediate WX001-3

At 0° C., intermediate WX001-2 (0.485 g, 2.20 mmol) was dissolved in a dichloromethane solution (10 mL), and triethylamine (667.26 mg, 6.59 mmol, 917.82 µL) was added; under nitrogen atmosphere, the reaction mixture was warmed to room temperature and stirred and reacted for 2 hours. After completion of the reaction, water (50 mL) was added, and extraction with dichloromethane (30 mL×3) was performed. The organic phase was combined, washed with water (30 mL×3), dried over anhydrous sodium sulfate and filtered; and the solvent was removed from the filtrate under reduced pressure. The resulting residue was purified by column chromatography (eluent: petroleum ether/ethyl acetate=100/1-10/1, volume ratio) to obtain target intermediate WX001-3. MS-ESI m/z: 185.0 [M+H]+. 1H NMR (400 MHz, CDCl3) δ: 8.70 (d, J=8.0 Hz, 1H), 8.01 (d, J=8.8 Hz, 1H), 7.78 (d, J=8.4 Hz, 1H), 7.61 (td, J=1.2, 8.4 Hz, 1H), 7.42 (td, J=1.0, 8.0 Hz, 1H), 7.21 (d, J=8.8 Hz, 1H), 4.70 (s, 2H).

Step 3: Synthesis of Intermediate WX001-4

At room temperature, intermediate WX001-3 (0.332 g, 1.80 mmol) was dissolved in toluene (20 mL), and then ethyl (triphenylphosphine) acetate (753.53 mg, 2.16 mmol) was added; under nitrogen atmosphere, the reaction mixture was heated to 130° C. and stirred and reacted for 35 hours. After completion of the reaction, the reaction mixture was cooled to room temperature, and the solvent was removed under reduced pressure; the resulting residue was purified by column chromatography (eluent: petroleum ether/ethyl acetate=100/1-20/1, volume ratio) to obtain target intermediate WX001-4. MS-ESI m/z: 255.0 [M+H]+. 1H NMR (400

MHz, CDCl$_3$) δ: 8.16 (d, J=8.4 Hz, 1H), 7.89 (d, J=8.4 Hz, 1H), 7.69 (s, 1H), 7.66 (d, J=8.8 Hz, 1H), 7.57 (d, J=8.8 Hz, 1H), 7.51 (td, J=1.2, 8.0 Hz, 1H), 7.41 (td, J=0.8, 8.0 Hz, 1H), 4.15 (q, J=6.8 Hz, 2H), 4.00 (s, 2H), 1.19 (t, J=7.2 Hz, 3H).

Step 4: Synthesis of Compound WX001

At 0° C., intermediate WX001-4 (0.185 g, 727.54 μmol) was dissolved in N, N-dimethylformamide (10 mL), and then potassium tert-butoxide (81.64 mg, 727.54 μmol) and acrylamide (103.42 mg, 1.46 mmol) were respectively added; under nitrogen atmosphere, the reaction mixture was stirred and reacted at 0° C. for 1.5 hours. After completion of the reaction, water (50 mL) was added for dilution, and extraction with ethyl acetate (50 mL×3) was performed. The organic phase was combined, washed with saturated brine (30 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain compound WX001. MS-ESI m/z: 279.9 [M+H]$^+$. $^1$H NMR (400 MHz, DMSO_d$_6$) δ: 10.96 (s, 1H), 8.19 (d, J=8.0 Hz, 1H), 8.06 (d, J=7.6 Hz, 1H), 8.02 (s, 1H), 7.87 (d, J=9.2 Hz, 1H), 7.80 (d, J=9.2 Hz, 1H), 7.60 (t, J=7.4 Hz, 1H), 7.52 (d, J=7.6 Hz, 1H), 4.69 (dd, J=4.0, 12.0 Hz, 1H), 2.96-2.83 (m, 1H), 2.70-2.57 (m, 1H), 2.48-2.36 (m, 1H), 2.34-2.22 (m, 1H).

Example 2

WX002

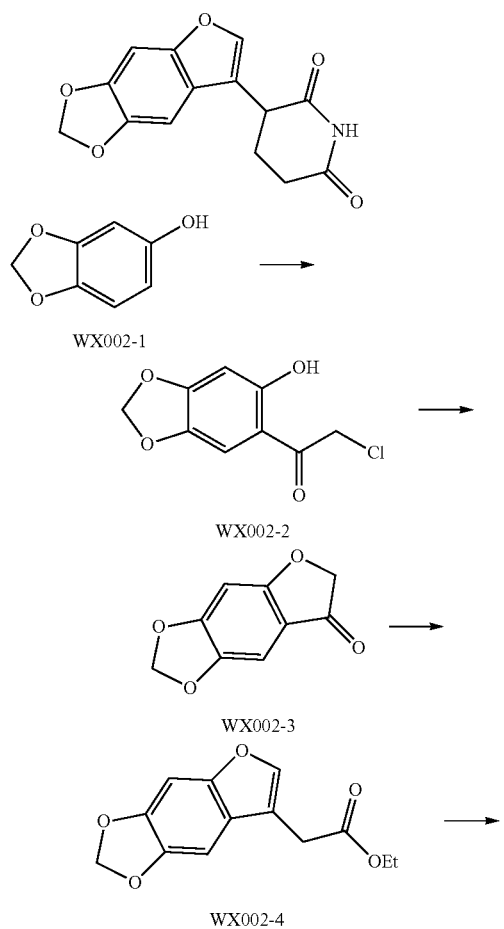

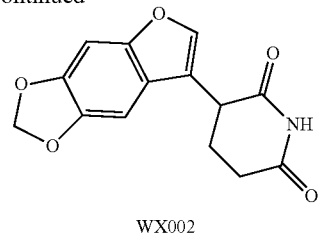

WX002

Step 1: Synthesis of Intermediate WX002-2

At 0° C., to a solution of boron trichloride in dichloromethane (1 M, 8.71 mL), a solution of WX002-1 (1.00 g, 7.25 mmol) in dichloromethane (40 mL) was slowly added dropwise. Under nitrogen atmosphere, the reaction mixture was stirred and reacted at 0° C. for 0.5 hours, and then chloroacetonitrile (657.23 mg, 8.71 mmol, 552.30 μL) was slowly added dropwise. Under nitrogen atmosphere, the reaction mixture was stirred and reacted at 0° C. for additional 0.5 hour. Finally, aluminum trichloride (483.66 mg, 3.63 mmol) was added in two batches, and the reaction mixture was warmed to room temperature and stirred and reacted for additional 3 hours. After completion of the reaction, the reaction mixture was poured into ice water (100 mL) and extraction with dichloromethane (50 mL×3) was performed; the organic phase was combined, washed with saturated brine (50 mL×2), dried over anhydrous sodium sulfate and filtered; and the solvent was removed from the filtrate under reduced pressure. The resulting residue was purified by column chromatography (eluent: petroleum ether/ethyl acetate=10/1-4/1, volume ratio) to obtain target intermediate WX002-2. $^1$H NMR (400 MHz, CDCl$_3$) δ: 12.43 (s, 1H), 6.94 (s, 1H), 6.42 (s, 1H), 5.95 (s, 2H), 4.47 (s, 2H).

Step 2: Synthesis of Intermediate WX002-3

At 0° C., intermediate WX002-2 (0.460 g, 2.14 mmol) was dissolved in dichloromethane solution (10 mL), and then triethylamine (650.70 mg, 6.43 mmol, 895.05 μL) was added; under nitrogen atmosphere, the reaction mixture was warmed to room temperature and stirred and reacted for 2 hours. After completion of the reaction, water (20 mL) was added, and extraction with dichloromethane (10 mL×3) was performed. The organic phase was combined, washed with saturated brine (30 mL×2), dried over anhydrous sodium sulfate and filtered; and the solvent was removed from the filtrate under reduced pressure. The resulting residue was purified by column chromatography (eluent: petroleum ether/ethyl acetate=10/1-3/1, volume ratio) to obtain target intermediate WX002-3. MS-ESI m/z: 179.0 [M+H]$^+$. $^1$H NMR (400 MHz, CDCl$_3$) δ: 6.89 (s, 1H), 6.50 (s, 1H), 6.00 (s, 2H), 4.57 (s, 2H).

Step 3: Synthesis of Intermediate WX002-4

At room temperature, intermediate WX002-3 (0.245 g, 1.38 mmol) was dissolved in toluene (10 mL), and then ethyl (triphenylphosphine) acetate (574.95 mg, 1.65 mmol) was added; under nitrogen atmosphere, the reaction mixture was heated to 130° C. and stirred and reacted for 35 hours. After completion of the reaction, the reaction mixture was cooled to room temperature, and the solvent was removed under reduced pressure; the resulting residue was purified by column chromatography (eluent: petroleum ether/ethyl acetate=100/1-10/1, volume ratio) to obtain target intermediate WX002-4. MS-ESI m/z: 249.0 [M+H]$^+$. $^1$H NMR (400 MHz, CDCl$_3$) δ: 7.55 (s, 1H), 6.97 (d, J=11.2 Hz, 2H), 6.01 (s, 2H), 4.21 (q, J=7.0 Hz, 2H), 3.64 (d, J=1.2 Hz, 2H), 1.30 (t, J=7.2 Hz, 3H).

Step 4: Synthesis of Compound WX002

At 0° C., intermediate WX003-2 (0.135 g, 543.85 μmol) was dissolved in N, N-dimethylformamide (10 mL), and then potassium tert-butoxide (61.03 mg, 543.85 μmol) and acrylamide (77.31 mg, 1.09 mmol) were added; under nitrogen atmosphere, the reaction mixture was stirred and reacted at 0° C. for 1.5 hours. After completion of the reaction, water (50 mL) was added for dilution, and extraction with ethyl acetate (50 mL×3) was performed. The organic phase was combined, washed with saturated brine (30 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain compound WX002. MS-ESI m/z: 274.1 [M+H]$^+$. $^1$H NMR (400 MHz, DMSO_$d_6$) δ: 10.88 (s, 1H), 7.77 (s, 1H), 7.24 (s, 1H), 7.08 (s, 1H), 6.04 (s, 2H), 4.05 (dd, J=4.6, 12.2 Hz, 1H), 2.78-2.65 (m, 1H), 2.60-2.52 (m, 1H), 2.30 (qd, J=4.4, 12.4 Hz, 1H), 2.13-2.00 (m, 1H).

Example 3

WX003

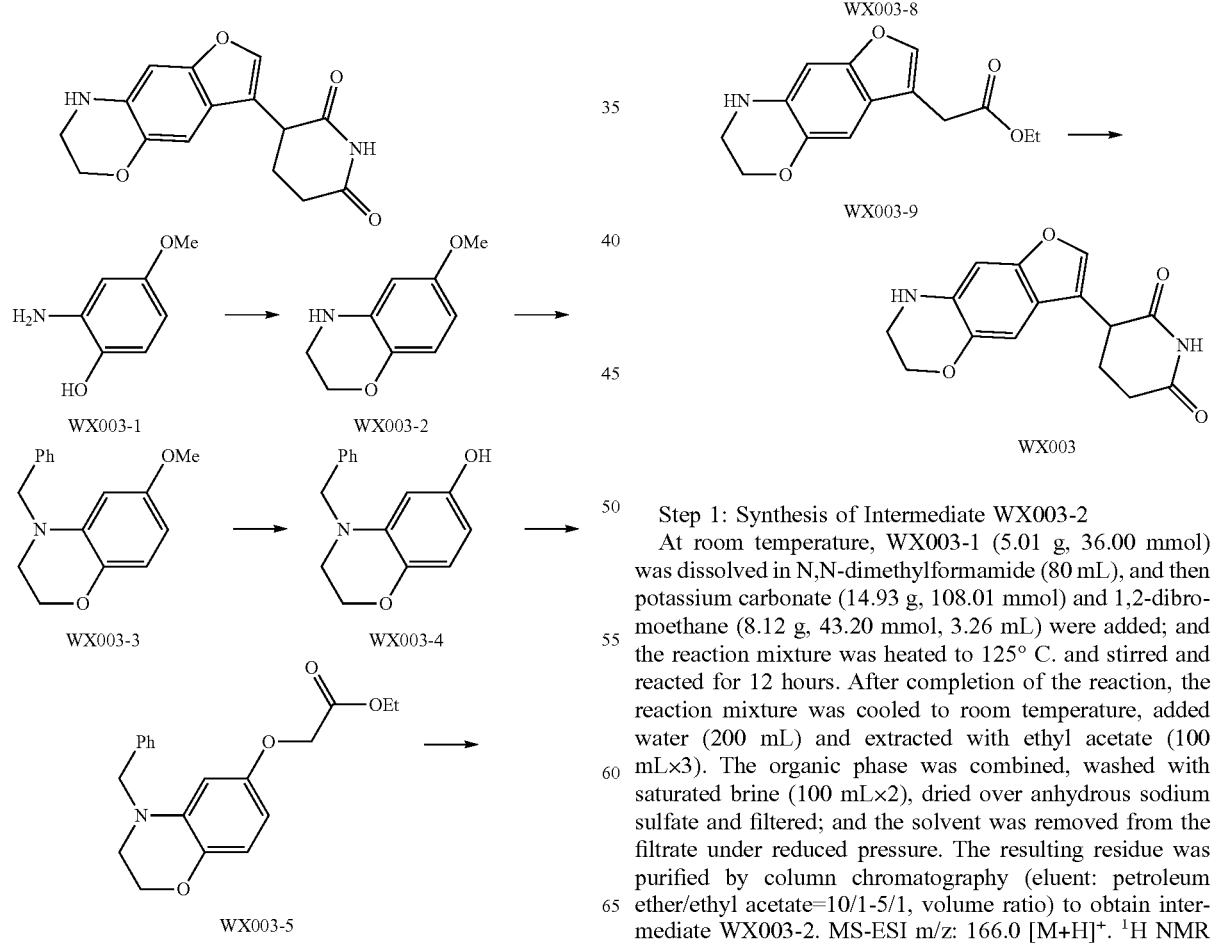

Step 1: Synthesis of Intermediate WX003-2

At room temperature, WX003-1 (5.01 g, 36.00 mmol) was dissolved in N,N-dimethylformamide (80 mL), and then potassium carbonate (14.93 g, 108.01 mmol) and 1,2-dibromoethane (8.12 g, 43.20 mmol, 3.26 mL) were added; and the reaction mixture was heated to 125° C. and stirred and reacted for 12 hours. After completion of the reaction, the reaction mixture was cooled to room temperature, added water (200 mL) and extracted with ethyl acetate (100 mL×3). The organic phase was combined, washed with saturated brine (100 mL×2), dried over anhydrous sodium sulfate and filtered; and the solvent was removed from the filtrate under reduced pressure. The resulting residue was purified by column chromatography (eluent: petroleum ether/ethyl acetate=10/1-5/1, volume ratio) to obtain intermediate WX003-2. MS-ESI m/z: 166.0 [M+H]$^+$. $^1$H NMR (400 MHz, DMSO_$d_6$) δ: 6.52 (d, J=8.8 Hz, 1H), 6.13 (d, J=3.2 Hz, 1H), 6.02 (dd, J=2.8, 8.8 Hz, 1H), 5.77 (s, 1H), 4.03 (t, J=4.4 Hz, 2H), 3.60 (s, 3H), 3.27-3.20 (m, 2H).

Step 2: Synthesis of Intermediate WX003-3

At 0° C. and under nitrogen atmosphere, intermediate WX003-2 (1.89 g, 11.44 mmol) was dissolved in acetonitrile (40 mL), and then potassium carbonate (4.74 g, 34.32 mmol) and benzyl bromide (2.15 g, 12.59 mmol, 1.49 mL) were added; and the reaction mixture was heated to 50° C. and stirred and reacted for 12 hours. After completion of the reaction, the reaction mixture was cooled to room temperature, added water (200 mL) and extracted with ethyl acetate (100 mL×3). The organic phase was combined, washed with saturated brine (100 mL×2), dried over anhydrous sodium sulfate and filtered; and the solvent was removed from the filtrate under reduced pressure. The resulting residue was purified by column chromatography (eluent: petroleum ether/ethyl acetate=100/1-20/1, volume ratio) to obtain intermediate WX003-3. MS-ESI m/z: 256.2 [M+H]+. 1H NMR (400 MHz, CDCl3) δ: 7.43-7.28 (m, 5H), 6.75 (d, J=8.8 Hz, 1H), 6.28 (d, J=2.8 Hz, 1H), 6.19 (dd, J=2.6, 8.6 Hz, 1H), 4.46 (s, 2H), 4.24 (t, J=4.4 Hz, 2H), 3.70 (s, 3H), 3.39 (t, J=4.4 Hz, 2H).

Step 3: Synthesis of Intermediate WX003-4

At −78° C. and under nitrogen atmosphere, intermediates WX003-3 (1.90 g, 6.58 mmol, purity: 88.42%) and WX003-3 (2.22 g, 8.11 mmol, purity: 93.25%) were dissolved in dichloromethane (30 mL), and then a solution of boron tribromide (12.19 g, 48.65 mmol, 4.69 mL) in dichloromethane (20 mL) was slowly added dropwise; and the reaction mixture was warmed to room temperature and stirred and reacted for 3 hours. After completion of the reaction, water (200 mL) was added, and extraction with dichloromethane (100 mL×3) was performed. The organic phase was combined, washed with saturated brine (100 mL×2), dried over anhydrous sodium sulfate and filtered; and the solvent was removed from the filtrate under reduced pressure. The resulting residue was purified by column chromatography (eluent: petroleum ether/ethyl acetate=100/1-20/1, volume ratio) to obtain intermediate WX003-4. MS-ESI m/z: 242.1 [M+H]+. 1H NMR (400 MHz, CDCl3) δ: 7.30-7.19 (m, 5H), 6.59 (d, J=8.4 Hz, 1H), 6.10 (d, J=2.8 Hz, 1H), 6.00 (dd, J=2.6, 8.6 Hz, 1H), 4.38 (s, 1H), 4.35 (s, 2H), 4.14 (t, J=4.4 Hz, 2H), 3.30 (t, J=4.4 Hz, 2H).

Step 4: Synthesis of Intermediate WX003-5

At 0° C. and under nitrogen atmosphere, intermediate WX003-4 (1.11 g, 4.18 mmol, purity: 90.76%) was dissolved in N,N-dimethylformamide (10 mL), and then potassium carbonate (1.15 g, 8.35 mmol) was added; the mixture was stirred and reacted at 0° C. for 0.5 hours, and then ethyl bromoacetate (697.28 mg, 4.18 mmol, 461.77 μL) was added; and the reaction mixture was warmed to room temperature and stirred and reacted for additional 12 hours. After completion of the reaction, water (50 mL) was added and extraction with ethyl acetate (30 mL×3) was performed. The organic phase was combined, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=10/1-5/1, volume ratio) to obtain intermediate WX003-5. MS-ESI m/z: 328.2 [M+H]+. 1H NMR (400 MHz, CDCl3) δ: 7.38-7.28 (m, 5H), 6.72 (d, J=8.4 Hz, 1H), 6.36 (d, J=2.8 Hz, 1H), 6.14 (dd, J=2.8, 8.4 Hz, 1H), 4.49 (s, 2H), 4.45 (s, 2H), 4.28-4.24 (m, 2H), 4.24-4.20 (m, 2H), 3.38 (t, J=4.6 Hz, 2H), 1.29 (t, J=7.2 Hz, 3H).

Step 5: Synthesis of Intermediate WX003-6

At room temperature and under nitrogen atmosphere, intermediate WX003-5 (1.35 g, 4.01 mmol, purity: 97.23%) was dissolved in tetrahydrofuran (8 mL), ethanol (4 mL) and water (2 mL), and then sodium hydroxide (160.38 mg, 4.01 mmol) was added; and the reaction mixture was stirred and reacted at room temperature for 12 hours. After completion of the reaction, tetrahydrofuran and ethanol were removed under reduced pressure. The resulting residue was added water (50 mL) and adjusted to pH 2-3 with 2 M hydrochloric acid aqueous; extraction with ethyl acetate (30 mL×3) was performed. The organic phase was combined, washed with saturated brine (20 mL×2), dried over anhydrous sodium sulfate and filtered; and the solvent was removed from the filtrate under reduced pressure to obtain intermediate WX003-6. MS-ESI m/z: 300.1 [M+H]+. 1H NMR (400 MHz, DMSO_d6) δ: 7.40-7.19 (m, 5H), 6.58 (d, J=8.8 Hz, 1H), 6.22 (d, J=2.4 Hz, 1H), 6.03 (dd, J=2.8, 8.8 Hz, 1H), 4.46 (s, 2H), 4.45 (s, 2H), 4.14 (t, J=4.2 Hz, 2H), 3.38 (t, J=4.4 Hz, 2H).

Step 6: Synthesis of Intermediate WX003-7

In a first reaction flask, at 10° C. and under nitrogen atmosphere, ethyl potassium malonate (1.27 g, 7.48 mmol) was dissolved in acetonitrile (20 mL), and then triethylamine (1.22 g, 12.04 mmol, 1.68 mL) and magnesium chloride (836.47 mg, 8.79 mmol) were added; and the reaction mixture was warmed to room temperature and stirred and reacted for 2 hours. In a second reaction flask, at 0° C. and under nitrogen atmosphere, intermediate WX003-6 (1.01 g, 3.25 mmol, purity: 96.43%) was dissolved in acetonitrile (10 mL), N,N'-carbonyldiimidazole (527.61 mg, 3.25 mmol) and triethylamine (329.26 mg, 3.25 mmol, 452.90 μL) were added; and the reaction mixture was warmed to room temperature and stirred and reacted for 2 hours. At 0° C. and under nitrogen atmosphere, the reaction mixture in the second reaction flask was added dropwise to the first reaction flask; and the reaction mixture was warmed to room temperature and stirred and reacted for additional 10 hours. After completion of the reaction, ice water (60 mL) was added and extraction with ethyl acetate (30 mL×3) was performed. The organic phase was combined, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=10/1-3/1, volume ratio) to obtain target intermediate WX003-7. MS-ESI m/z: 370.2 [M+H]+. 1H NMR (400 MHz, CDCl3) δ: 7.42-7.28 (m, 5H), 6.73 (d, J=8.8 Hz, 1H), 6.27 (d, J=2.8 Hz, 1H), 6.11 (dd, J=2.8, 8.8 Hz, 1H), 4.51 (s, 2H), 4.46 (s, 2H), 4.24 (t, J=4.6 Hz, 2H), 4.16 (q, J=7.2 Hz, 2H), 3.57 (s, 2H), 3.40 (t, J=4.4 Hz, 2H), 1.24 (t, J=7.2 Hz, 3H).

Step 7: Synthesis of Intermediate WX003-8

At room temperature and under nitrogen atmosphere, intermediate WX003-7 (0.693 g, 1.60 mmol, purity: 85.45%) was dissolved in toluene (10 mL), and then polyphosphoric acid (0.500 g) was added; and the reaction mixture was heated to 110° C. and stirred and reacted for 2 hours. After completion of the reaction, the reaction mixture was cooled to room temperature, added water (50 mL) and extracted with ethyl acetate (30 mL×3). The organic phase was combined, washed with saturated brine (30 mL×2), dried over anhydrous sodium sulfate and filtered; and the solvent was removed from the filtrate under reduced pressure. The resulting residue was purified by column chromatography (eluent: petroleum ether/ethyl acetate=20/1-10/1, volume ratio) to obtain intermediate WX003-8. MS-ESI m/z: 352.5 [M+H]+. 1H NMR (400 MHz, CDCl3) δ: 7.40 (s, 1H), 7.38-7.28 (m, 5H), 6.97 (s, 1H), 6.74 (s, 1H), 4.52 (s, 2H), 4.30 (t, J=4.6 Hz, 2H), 4.20 (q, J=7.2 Hz, 2H), 3.60 (d, J=0.8 Hz, 2H), 3.46 (t, J=4.6 Hz, 2H), 1.30 (t, J=7.0 Hz, 3H).

Step 8: Synthesis of Intermediate WX003-9

At room temperature and under nitrogen atmosphere, intermediate WX003-8 (0.110 g, 313.04 μmol) was dissolved in tetrahydrofuran (1 mL), and wet palladium carbon (30 mg, purity: 10%) was added; and the reaction mixture was evacuated and subjected to replacement with hydrogen several times; and the reaction mixture was stirred and reacted at room temperature and a hydrogen (15 psi) atmosphere for 0.5 hour. After completion of the reaction, the reaction mixture was filtered, and the solvent was removed from the filtrate under reduced pressure. The resulting residue was purified by column chromatography (eluent: petroleum ether/ethyl acetate=5/1-2/1, volume ratio) to obtain intermediate WX003-9. MS-ESI m/z: 262.1 [M+H]$^+$.
$^1$H NMR (400 MHz, CDCl$_3$) δ: 7.34 (s, 1H), 6.84 (s, 1H), 6.62 (s, 1H), 4.18 (t, J=4.4 Hz, 2H), 4.10 (q, J=7.4 Hz, 2H), 3.51 (s, 2H), 3.38 (t, J=4.4 Hz, 2H), 1.20 (t, J=7.2 Hz, 3H).

Step 9: Synthesis of WX003

At 0° C. and under nitrogen atmosphere, intermediate WX003-9 (78 mg, 298.54 μmol) was dissolved in N,N-dimethylformamide (10 mL), and then potassium tert-butoxide (33.50 mg, 298.54 μmol) and acrylamide (42.44 mg, 597.08 μmol) were added successively; and the reaction mixture was stirred and reacted at 0° C. and under nitrogen atmosphere for 2 hours. After completion of the reaction, water (50 mL) was added and extraction with ethyl acetate (30 mL×3) was performed. The organic phase was combined, washed with saturated brine (30 mL×2), dried over anhydrous sodium sulfate and filtered; and the solvent was removed from the filtrate under reduced pressure. The resulting residue was subjected to preparative HPLC (mobile phase: acetonitrile/water; acid system: 0.05% HCl) to obtain compound WX003. MS-ESI m/z: 287.0 [M+H]$^+$. $^1$H NMR (400 MHz, MeOD_d$_4$) δ: 7.75 (s, 1H), 7.31 (s, 1H), 7.16 (s, 1H), 4.39 (t, J=4.6 Hz, 2H), 4.10 (dd, J=5.2, 11.2 Hz, 1H), 3.66 (t, J=4.6 Hz, 2H), 2.88-2.61 (m, 2H), 2.44-2.20 (m, 2H).

Example 4

WX004

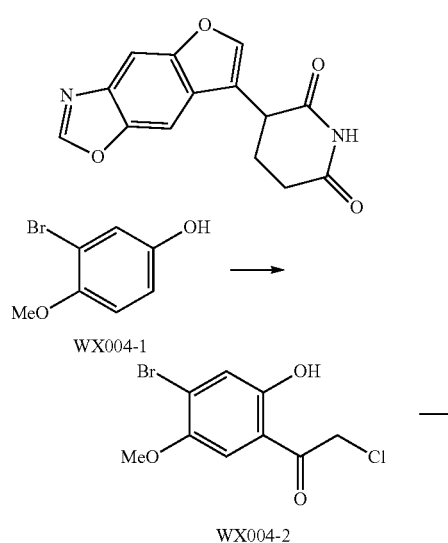

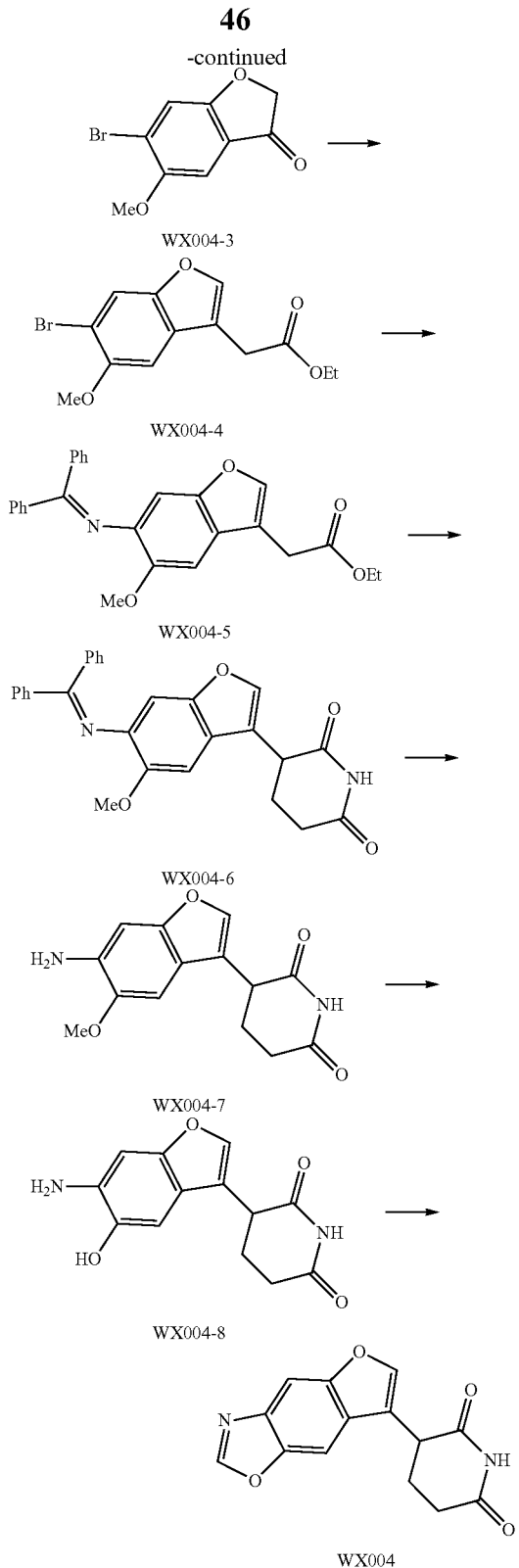

Step 1: Synthesis of Intermediate WX004-2

At room temperature and under nitrogen atmosphere, boron trichloride (1 M, 118.21 mL) was added to the reaction flask and cooled to 0° C.; and then a solution of WX004-1 (20 g, 98.51 mmol) in dichloromethane (40 mL) was added dropwise. After completion of the dropwise addition, the mixture was stirred and reacted at 0° C. for 0.5 hour, and then chloroacetonitrile (8.92 g, 118.21 mmol, 7.50 mL) was added dropwise. Finally, aluminum trichloride (13.13 g, 98.51 mmol) was slowly added, and the reaction mixture was warmed to room temperature and stirred and reacted for additional 4.5 hours. After completion of the reaction, water (40 mL) was added, and extraction with dichloromethane (40 mL×3) was performed. The organic phase was combined, dried over anhydrous sodium sulfate, and filtered to obtain a solution of crude intermediate WX004-2 in dichloromethane (160 mL), which was directly used in the next step.

Step 2: Synthesis of Intermediate WX004-3

At room temperature and under nitrogen atmosphere, to a solution of intermediate WX004-2 in dichloromethane (92.35 mmol, 150 mL), triethylamine (10.14 g, 100.17 mmol, 13.94 mL) was added; and the reaction mixture was stirred and reacted at room temperature for 2 hours. After completion of the reaction, water (200 mL) was added for separation, and the aqueous phase was extracted with dichloromethane (100 mL×3). The organic phase was combined, dried over anhydrous sodium sulfate and filtered; and the solvent was removed from the filtrate under reduced pressure. The resulting residue was purified by column chromatography (eluent: petroleum ether/ethyl acetate=1/0-3/1, volume ratio) to obtain target intermediate WX004-3. $^1$H NMR (400 MHz, CDCl$_3$) δ: 7.44 (s, 1H), 7.08 (s, 1H), 4.63 (s, 2H), 3.90 (s, 3H).

Step 3: Synthesis of Intermediate WX004-4

At room temperature, intermediate WX004-3 (7.87 g, 32.38 mmol) was dissolved in toluene (100 mL), and then ethyl (triphenylphosphine) acetate (16.92 g, 48.57 mmol) was added; and the reaction mixture was heated to 130° C. and stirred and reacted for 40 hours. After completion of the reaction, the reaction mixture was cooled to room temperature, and the solvent was removed under reduced pressure; the resulting residue was slurried with methyl tert-butyl ether (100 mL) and filtered; and the solvent was removed from the filtrate under reduced pressure. The resulting residue was purified by column chromatography (eluent: petroleum ether/ethyl acetate=1/0-3/1, volume ratio) to obtain target intermediate WX004-4. $^1$H NMR (400 MHz, CDCl$_3$) δ: 7.67 (s, 1H), 7.58 (s, 1H), 7.03 (s, 1H), 4.18 (q, J=7.2 Hz, 2H), 3.92 (s, 3H), 3.65 (s, 2H), 1.26 (t, J=7.2 Hz, 3H).

Step 4: Synthesis of Intermediate WX004-5

At room temperature and under nitrogen atmosphere, intermediate WX004-4 (2.8 g, 8.94 mmol) was dissolved in 1,4-dioxane (50 mL), and then benzophenonimine (2.43 g, 13.41 mmol), tris(dibenzylideneacetone)dipalladium (655.04 mg, 715.33 μmol), 4,5-bisdiphenylphosphino-9,9-dimethylxanthene (827.81 mg, 1.43 mmol) and cesium carbonate (8.74 g, 26.82 mmol) were added successively; and the reaction mixture was heated to 80° C. and stirred and reacted for 4 hours. After completion of the reaction, the reaction mixture was cooled to room temperature and filtered; and the solvent was removed from the filtrate under reduced pressure. The resulting residue was purified by column chromatography (eluent: petroleum ether/ethyl acetate=1/0-20/1, volume ratio) to obtain target intermediate WX004-5. $^1$H NMR (400 MHz, CDCl$_3$) δ: 7.86-7.72 (m, 2H), 7.57-7.38 (m, 4H), 7.25-7.10 (m, 5H), 6.85 (s, 1H), 6.72 (s, 1H), 4.18 (q, J=7.2 Hz, 2H), 3.75 (s, 3H), 3.61 (s, 2H), 1.25 (t, J=7.2 Hz, 3H).

Step 5: Synthesis of Intermediate WX004-6

At room temperature and under nitrogen atmosphere, intermediate WX004-5 (1.2 g, 2.90 mmol) was dissolved in N,N-dimethylformamide (30 mL) and cooled to 0° C., and then potassium tert-butoxide (325.67 mg, 2.90 mmol) and acrylamide (206.29 mg, 2.90 mmol) were added successively; and the reaction mixture was stirred and reacted at 0° C. for 0.5 hour. After completion of the reaction, water (100 mL) and ethyl acetate (100 mL) were added for dilution; after separation, the organic phase was collected, and the aqueous phase was extracted with ethyl acetate (50 mL×2). The organic phase was combined, washed with half-saturated brine (50 mL×3), dried over anhydrous sodium sulfate and filtered; and the solvent was removed from the filtrate under reduced pressure. The resulting residue was purified by column chromatography (eluent: petroleum ether/ethyl acetate=1/0-2/3, volume ratio) to obtain intermediate WX004-6. $^1$H NMR (400 MHz, DMSO_d$_6$) δ: 10.85 (s, 1H), 7.68-7.61 (m, 3H), 7.55-7.44 (m, 3H), 7.36-7.24 (m, 3H), 7.15 (dd, J=1.7, 7.5 Hz, 2H), 7.00 (s, 1H), 6.77 (s, 1H), 4.10-3.97 (m, 1H), 3.68 (s, 3H), 2.76-2.63 (m, 1H), 2.61-2.53 (m, 1H), 2.36-2.22 (m, 1H), 2.13-2.02 (m, 1H).

Step 6: Synthesis of Intermediate WX004-7

At room temperature, to intermediate WX004-6 (500 mg, 1.14 mmol), hydrochloric acid/ethyl acetate solution (20 mL, 4 M) and water (0.2 mL) were added; and the reaction mixture was stirred and reacted at room temperature for 48 hours. After completion of the reaction, water (40 mL) was added; after separation, the organic phase was removed, and the aqueous phase was adjusted to pH 6-7 with a saturated sodium bicarbonate solution and extracted with ethyl acetate (20 mL×2). The organic phase was combined, and the solvent was removed under reduced pressure to obtain target intermediate WX004-7. MS-ESI m/z: 275.1 [M+H]$^+$.

Step 7: Synthesis of Intermediate WX004-8

At room temperature, intermediate WX004-7 (300 mg, 717.87 μmol, purity: 65.63%) was dissolved in dichloromethane (10 mL), cooled to 0° C., and then boron tribromide (5.20 g, 20.76 mmol, 2 mL) was added; and the reaction mixture was naturally warmed to room temperature and stirred and reacted for 3 hours. After completion of the reaction, the reaction mixture was poured into ice water (50 mL), and diluted with ethyl acetate (20 mL); after separation, the organic phase was removed, and the aqueous phase was adjusted to pH 6-7 with saturated sodium bicarbonate solution and extracted with ethyl acetate (20 mL×3). The organic phase was combined, dried over anhydrous sodium sulfate and filtered; and the solvent was removed from the filtrate under reduced pressure. The resulting residue was purified by column chromatography (eluent: petroleum ether/ethyl acetate=1/1-0/1, volume ratio) to obtain target intermediate WX004-8. $^1$H NMR (400 MHz, DMSO_d$_6$) δ: 10.86 (s, 1H), 9.00 (s, 1H), 7.47 (s, 1H), 6.72 (s, 1H), 6.70 (s, 1H), 4.69 (br s, 2H), 3.94 (dd, J=4.8, 11.2 Hz, 1H), 2.79-2.65 (m, 1H), 2.61-2.53 (m, 1H), 2.26-2.03 (m, 2H).

Step 8: Synthesis of WX004

At room temperature and under nitrogen atmosphere, intermediate WX004-8 (60 mg, 230.55 μmol) was dissolved in N,N-dimethylformamide (3 mL), and then triethyl orthoformate (41.00 mg, 276.66 μmol, 46.02 μL) and zirconium tetrachloride (5.37 mg, 23.06 μmol) were added successively; and the reaction mixture was stirred and reacted at room temperature for 2 hours. After completion of the reaction, water (20 mL) and ethyl acetate (20 mL) were added for dilution; after separation, the organic phase was collected, and the aqueous phase was extracted with ethyl acetate (15 mL×3). The organic phase was combined, dried over anhydrous sodium sulfate and filtered; and the solvent was removed from the filtrate under reduced pressure. The resulting residue was purified by preparative HPLC (mobile phase: acetonitrile/water; alkalic system: 10 mM NH₄HCO₃) to obtain compound WX004. MS-ESI m/z: 271.0 [M+H]⁺. ¹H NMR (400 MHz, DMSO_d₆) δ: 10.92 (s, 1H), 8.74 (s, 1H), 8.01 (s, 1H), 8.00 (s, 1H), 7.97 (s, 1H), 4.21 (dd, J=4.8, 12.0 Hz, 1H), 2.85-2.70 (m, 1H), 2.69-2.56 (m, 1H), 2.44-2.30 (m, 1H), 2.22-2.09 (m, 1H).

Example 5

WX005

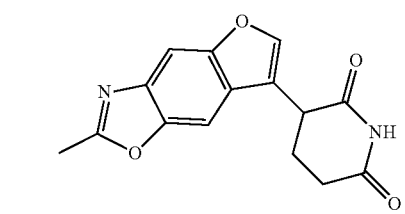

WX004-8

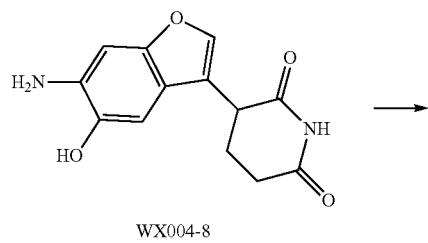

WX005

At room temperature and under nitrogen atmosphere, intermediate WX004-8 (80 mg, 307.40 μmol) was dissolved in N,N-dimethylformamide (5 mL), and then triethyl orthoacetate (59.84 mg, 368.88 μmol, 67.62 μL) and zirconium tetrachloride (7.16 mg, 30.74 μmol) were added successively; and the reaction mixture was stirred and reacted at room temperature for 2 hours. After completion of the reaction, water (20 mL) and ethyl acetate (20 mL) were added for dilution; after separation, the organic phase was collected, and the aqueous phase was extracted with ethyl acetate (20 mL×2). The organic phase was combined, dried over anhydrous sodium sulfate and filtered; and the solvent was removed from the filtrate under reduced pressure. The resulting residue was purified by preparative HPLC (mobile phase: acetonitrile/water; alkalic system: 10 mM NH₄HCO₃) to obtain compound WX005. MS-ESI m/z: 285.1 [M+H]⁺. ¹H NMR (400 MHz, DMSO_d₆) δ: 10.90 (s, 1H), 7.96 (s, 1H), 7.84 (s, 1H), 7.83 (s, 1H), 4.19 (dd, J=4.6, 12.2 Hz, 1H), 2.83-2.68 (m, 1H), 2.62 (s, 3H), 2.57-2.50 (m, 1H), 2.46-2.31 (m, 1H), 2.16-2.15 (m, 1H).

Example 6

WX006

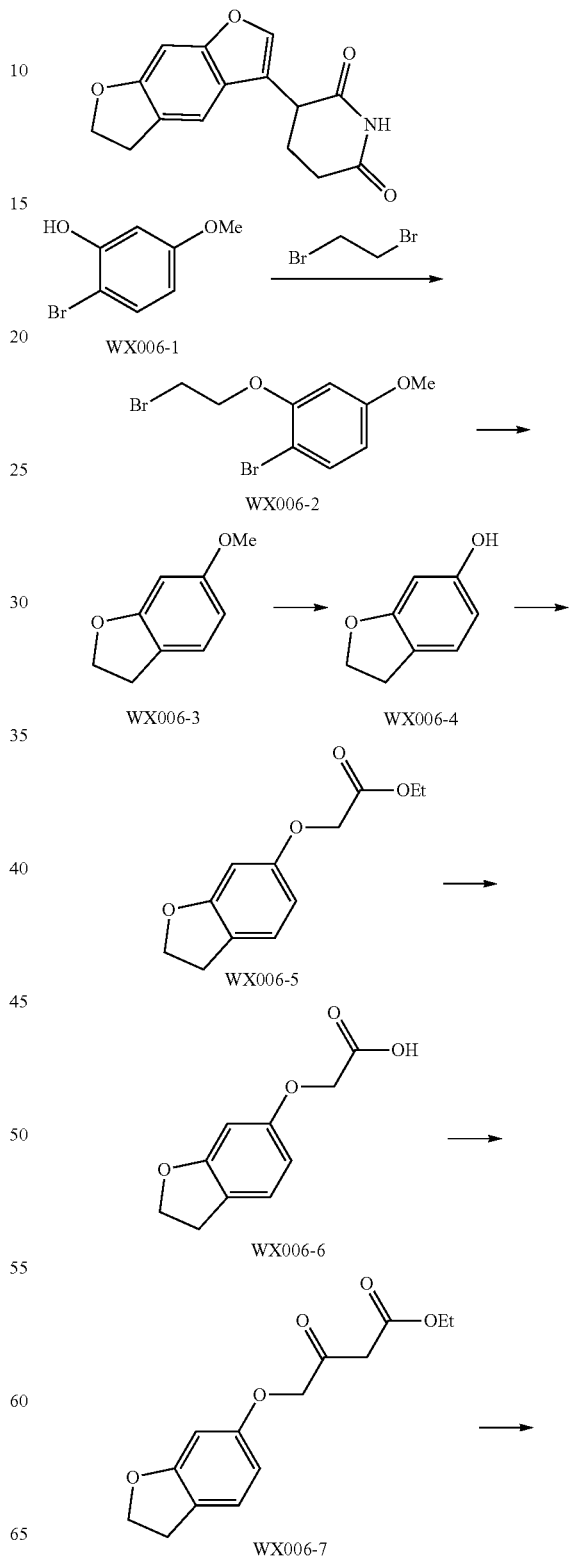

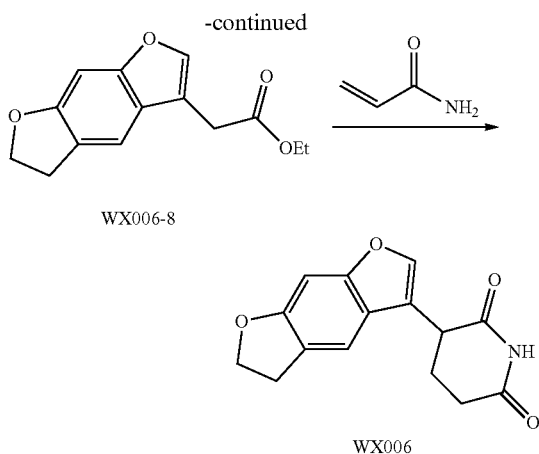

WX006-8

WX006

Step 1: Synthesis of Intermediate WX006-2

At room temperature and under nitrogen atmosphere, WX006-1 (15.00 g, 73.88 mmol) and 1,2-dibromoethane (41.64 g, 221.64 mmol, 16.72 mL) were dissolved in N,N-dimethylformamide (150 mL), then potassium carbonate (20.42 g, 147.76 mmol) was added; and the reaction mixture was heated to 50° C. and stirred and reacted at 50° C. for 12 hours. After completion of the reaction, the reaction mixture was cooled to room temperature, poured into water (300 mL) and extracted with ethyl acetate (200 mL×3). The organic phase was combined, washed with saturated brine (100 mL×2), dried over anhydrous sodium sulfate and filtered; and the solvent was removed from the filtrate under reduced pressure. The resulting residue was purified by column chromatography (eluent: petroleum ether/ethyl acetate=20/1-10/1, volume ratio) to obtain intermediate WX006-2. $^1$H NMR (400 MHz, CDCl$_3$) δ: 7.42 (d, J=8.8 Hz, 1H), 6.49 (d, J=2.8 Hz, 1H), 6.45 (dd, J=2.8, 8.8 Hz, 1H), 4.32 (t, J=6.8 Hz, 2H), 3.80 (s, 3H), 3.68 (t, J=6.6 Hz, 2H).

Step 2: Synthesis of Intermediate WX006-3

At −70° C. and under nitrogen atmosphere, intermediate WX006-2 (5.41 g, 16.97 mmol, purity: 97.26%) was dissolved in tetrahydrofuran (40 mL), and then a solution of n-butyllithium in n-hexane (2.5 M, 20.37 mL) was slowly added dropwise; at −70° C. and under nitrogen atmosphere, the reaction mixture was stirred and reacted for 2 hours. After completion of the reaction, the reaction mixture was poured into saturated ammonium chloride solution (100 mL) and extraction with ethyl acetate (50 mL×3) was performed. The organic phase was combined, washed with saturated brine (50 mL×2), dried over anhydrous sodium sulfate and filtered; and the solvent was removed from the filtrate under reduced pressure. The resulting residue was purified by column chromatography (eluent: petroleum ether/ethyl acetate=50/1-10/1, volume ratio) to obtain intermediate WX006-3. MS-ESI m/z: 151.0 [M+H]$^+$. $^1$H NMR (400 MHz, CDCl$_3$) δ: 7.07 (d, J=4.4 Hz, 1H), 6.43-6.37 (m, 2H), 4.58 (t, J=8.6 Hz, 2H), 3.77 (s, 3H), 3.15 (t, J=8.6 Hz, 2H).

Step 3: Synthesis of Intermediate WX006-4

At −78° C. and under nitrogen atmosphere, intermediate WX006-3 (2.63 g, 16.39 mmol, purity: 93.61%) was dissolved in dichloromethane (30 mL), and a solution of boron tribromide (12.32 g, 49.18 mmol, 4.74 mL) in dichloromethane (5 mL) was slowly added dropwise to the above-mentioned reaction mixture; and the reaction mixture was warmed to room temperature and stirred and reacted at room temperature for 12 hours. After completion of the reaction, the reaction mixture was cooled to 0° C., poured into methanol (5 mL), and then added water (50 mL) and extracted with dichloromethane (30 mL×3). The organic phase was combined, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=10/1-3/1, volume ratio) to obtain intermediate WX006-4. MS-ESI m/z: 137.0 [M+H]$^+$. $^1$H NMR (400 MHz, DMSO_d$_6$) δ: 9.33 (s, 1H), 6.86 (d, J=8.0 Hz, 1H), 6.28 (d, J=2.4 Hz, 1H), 6.14 (dd, J=2.2, 8.2 Hz, 1H), 3.55 (t, J=7.8 Hz, 2H), 2.93 (t, J=7.6 Hz, 2H).

Step 4: Synthesis of Intermediate WX006-5

At 0° C. and under nitrogen atmosphere, intermediate WX006-4 (1.72 g, 12.63 mmol) was dissolved in N,N-dimethylformamide (20 mL), and then potassium carbonate (3.49 g, 25.27 mmol) was added; the mixture was stirred and reacted at 0° C. for 0.5 hours, and then ethyl bromoacetate (2.11 g, 12.63 mmol, 1.40 mL) was added; and the reaction mixture was warmed to room temperature and stirred and reacted at room temperature for additional 12 hours. After completion of the reaction, water (30 mL) was added to the reaction mixture, and extraction with ethyl acetate (20 mL×3) was performed. The organic phase was combined, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=10/1-5/1, volume ratio) to obtain intermediate WX006-5. MS-ESI m/z: 223.1 [M+H]$^+$. $^1$H NMR (400 MHz, CDCl$_3$) δ: 7.07 (d, J=4.4 Hz, 1H), 6.43-6.34 (m, 2H), 4.62-4.54 (m, 4H), 4.27 (q, J=7.0 Hz, 2H), 3.14 (t, J=8.6 Hz, 2H), 1.31 (t, J=7.2 Hz, 3H).

Step 5: Synthesis of Intermediate WX006-6

At room temperature and under nitrogen atmosphere, intermediate WX006-5 (2.67 g, 11.73 mmol, purity: 97.64%) was dissolved in tetrahydrofuran (16 mL), ethanol (8 mL) and water (4 mL), and then sodium hydroxide (469.23 mg, 11.73 mmol) was added; and the reaction mixture was stirred and reacted at room temperature for 12 hours. After completion of the reaction, tetrahydrofuran and ethanol were removed under reduced pressure. The resulting residue was added water (100 mL) and adjusted to pH 2-3 with 2 M hydrochloric acid aqueous; and extraction with ethyl acetate (50 mL×3) was performed. The organic phase was combined, washed with saturated brine (50 mL×2), dried over anhydrous sodium sulfate and filtered; and the solvent was removed from the filtrate under reduced pressure to obtain intermediate WX006-6. MS-ESI m/z: 195.0 [M+H]$^+$. $^1$H NMR (400 MHz, DMSO_d$_6$) δ: 12.90 (s, 1H), 7.08 (d, J=8.8 Hz, 1H), 6.38-6.30 (m, 2H), 4.60 (s, 2H), 4.52 (t, J=8.8 Hz, 2H), 3.08 (t, J=8.6 Hz, 2H).

Step 6: Synthesis of Intermediate WX006-7

At 10° C. and under nitrogen atmosphere, in the first reaction flask, ethyl potassium malonate (2.55 g, 14.99 mmol) was added to acetonitrile (20 mL), and then a mixture of triethylamine (2.44 g, 24.12 mmol, 3.36 mL) and magnesium chloride (1.68 g, 17.60 mmol) was added to the above-mentioned reaction mixture; and the reaction mixture was warmed to room temperature and stirred and reacted at room temperature for 2 hours. At 0° C. and under nitrogen atmosphere, in another reaction flask, intermediate WX006-6 (1.28 g, 6.52 mmol, purity: 98.88%) was dissolved in acetonitrile (5 mL), and then N,N-carbonyldiimidazole (1.06 g, 6.52 mmol) and triethylamine (659.54 mg, 6.52 mmol, 907.21 μL) were added successively; and the reaction mixture was warmed to room temperature and stirred and reacted at room temperature for 2 hours. Finally, at 0° C. and under nitrogen atmosphere, the reaction mixture in the second reaction flask was added dropwise to the first reaction flask; and the reaction mixture was warmed to room temperature and stirred and reacted at room temperature for additional 10 hours. After completion of the reaction, ice water (100 mL) was added to the reaction mixture, and extraction with ethyl acetate (60 mL×3) was performed. The organic phase was combined, washed with saturated brine (50 mL×2), dried over anhydrous sodium sulfate and filtered; and the solvent was removed from the filtrate under reduced pressure. The resulting residue was purified by column chromatography (eluent: petroleum ether/ethyl acetate=10/1-5/1, volume ratio) to obtain intermediate WX006-7. $^1$H NMR (400 MHz, CDCl$_3$) δ: 7.07 (d, J=8.0 Hz, 1H), 6.41-6.33 (m, 2H), 4.63-4.54 (m, 4H), 4.20 (q, J=7.0 Hz, 2H), 3.62 (s, 2H), 3.15 (t, J=8.4 Hz, 2H), 1.27 (t, J=7.0 Hz, 3H).

Step 7: Synthesis of Intermediate WX006-8

At room temperature and under nitrogen atmosphere, intermediate WX006-7 (0.845 g, 2.73 mmol, purity: 85.36%) was dissolved in toluene (10 mL), and then polyphosphoric acid (0.400 g) was added; and the reaction mixture was heated to 110° C. and stirred and reacted at 110° C. for 1 hour. After completion of the reaction, the reaction mixture was cooled to room temperature, added water (30 mL) and extracted with ethyl acetate (20 mL×3). The organic phase was combined, washed with saturated brine (10 mL×2), dried over anhydrous sodium sulfate and filtered; and the solvent was removed from the filtrate under reduced pressure. The resulting residue was purified by column chromatography (eluent: petroleum ether/ethyl acetate=20/1-10/1, volume ratio) to obtain intermediate WX006-8. MS-ESI m/z: 246.6 [M+H]$^+$. $^1$H NMR (400 MHz, CDCl$_3$) δ: 7.49 (s, 1H), 7.32 (s, 1H), 6.89 (s, 1H), 4.63 (t, J=8.6 Hz, 2H), 4.19 (q, J=7.0 Hz, 2H), 3.64 (s, 2H), 3.28 (t, J=8.4 Hz, 2H), 1.28 (t, J=7.2 Hz, 3H).

Step 8: Synthesis of WX006

At 0° C. and under nitrogen atmosphere, intermediate WX006-8 (0.670 g, 2.67 mmol, purity: 98.12%) was dissolved in N,N-dimethylformamide (10 mL); potassium tert-butoxide (299.55 mg, 2.67 mmol) was added, and then acrylamide (189.75 mg, 2.67 mmol) was added; and the reaction mixture was stirred and reacted at 0° C. and under nitrogen atmosphere for 1 hour. After completion of the reaction, water (50 mL) was added to the reaction mixture, and the reaction was quenched and extracted with ethyl acetate (30 mL×3). The organic phase was combined, washed with saturated brine (30 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain compound WX006. MS-ESI m/z: 272.0 [M+H]$^+$. $^1$H NMR (400 MHz, DMSO_d$_6$) δ: 10.87 (s, 1H), 7.71 (s, 1H), 7.37 (s, 1H), 6.96 (s, 1H), 4.59 (t, J=8.6 Hz, 2H), 4.05 (dd, J=4.8, 12.0 Hz, 1H), 3.22 (t, J=8.6 Hz, 2H), 2.78-2.66 (m, 1H), 2.61-2.53 (m, 1H), 2.36-2.23 (m, 1H), 2.15-2.05 (m, 1H).

Example 7

WX007

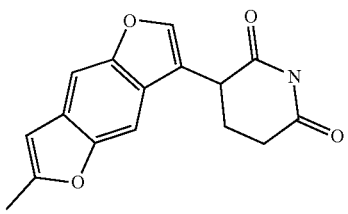

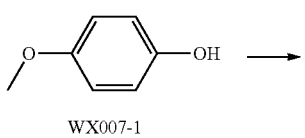

WX007-1

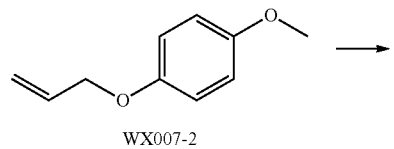

WX007-2

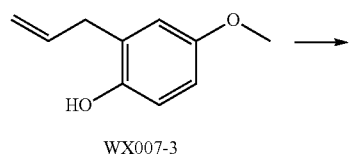

WX007-3

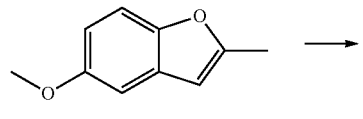

WX007-4

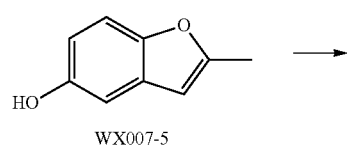

WX007-5

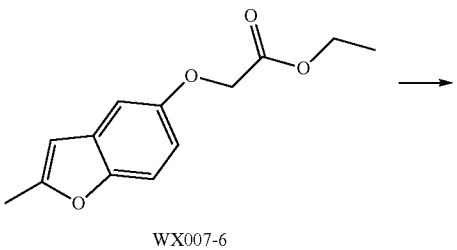

WX007-6

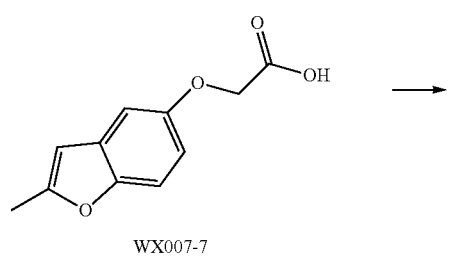

WX007-7

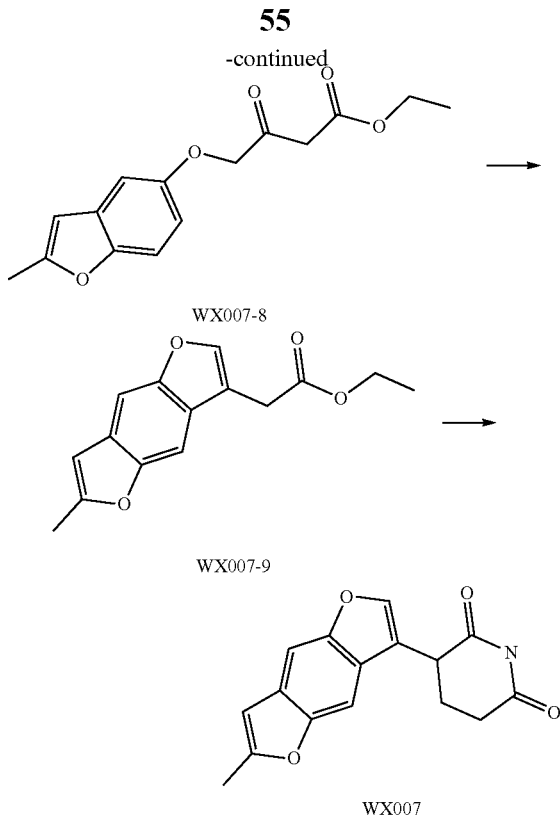

Step 1: Synthesis of Intermediate WX007-2

At room temperature under nitrogen atmosphere, compound WX007-1 (30.00 g, 241.67 mmol) and allyl bromide (35.08 g, 290.00 mmol) were dissolved in acetone (300 mL), and potassium carbonate (66.80 g, 483.34 mmol) was added; and the reaction mixture was heated to 65° C. and stirred and reacted at 65° C. for 12 hours. After completion of the reaction, the reaction mixture was cooled to room temperature and filtered, and the filter cake was discarded, the solvent was removed from the filtrate under reduced pressure. The resulting residue was purified by column chromatography (eluent: petroleum ether/ethyl acetate=1/0-100/1, volume ratio) to obtain intermediate WX007-2. MS-ESI m/z: 165.0 [M+H]$^+$. $^1$H NMR (400 MHz, CDCl$_3$) δ: 6.92-6.78 (m, 4H), 6.13-6.00 (m, 1H), 5.41 (dq, J=1.6, 17.2 Hz, 1H), 5.28 (dq, J=1.4, 10.2 Hz, 1H), 4.51 (t, J=1.6 Hz, 1H), 4.50 (t, J=1.4 Hz, 1H), 3.78 (s, 3H).

Step 2: Synthesis of Intermediate WX007-3

At room temperature under nitrogen atmosphere, intermediate WX007-2 (33.00 g, 196.63 mmol, purity: 97.84%) was added to a single-necked flask; and the reaction mixture was heated to 180° C. and stirred and reacted at 180° C. for 6 hours. After completion of the reaction, the reaction mixture was cooled to room temperature. The resulting residue was purified by column chromatography (eluent: petroleum ether/ethyl acetate=100/1-10/1, volume ratio) to obtain intermediate WX007-3. MS-ESI m/z: 165.0 [M+H]$^+$. $^1$H NMR (400 MHz, CDCl$_3$) δ: 6.79-6.73 (m, 1H), 6.72-6.64 (m, 2H), 6.11-5.92 (m, 1H), 5.23-5.17 (m, 1H), 5.16-5.13 (m, 1H), 4.63 (s, 1H), 3.77 (s, 3H), 3.39 (d, J=6.0 Hz, 2H).

Step 3: Synthesis of Intermediate WX007-4

At room temperature, intermediate WX007-3 (5.00 g, 28.86 mmol, purity: 94.77%) was dissolved in dimethylacetamide (3 mL) and water (0.5 mL). Palladium chloride (102.35 mg, 577.16 μmol) and sodium acetate (4.73 g, 57.72 mmol) were added. The reaction mixture was evacuated and ventilated with oxygen several times. The reaction mixture was stirred and reacted for 1 hour at 25° C. and under oxygen (15 psi) atmosphere. Three batches were combined for treatment. After completion of the reaction, water (200 mL) was added to the reaction mixture, and extraction with ethyl acetate (100 mL×3) was performed. The organic phase was combined, washed with saturated brine (100 mL×2), dried over anhydrous sodium sulfate and filtered, and the solvent was removed from the filtrate under reduced pressure. The resulting residue was purified by column chromatography (eluent: petroleum ether/ethyl acetate=20/1-10/1, volume ratio) to obtain intermediate WX007-4. MS-ESI m/z: 163.0 [M+H]$^+$. $^1$H NMR (400 MHz, CDCl$_3$) δ: 7.29 (d, J=9.2 Hz, 1H), 6.96 (d, J=2.8 Hz, 1H), 6.81 (dd, J=2.6, 9.0 Hz, 1H), 6.32 (s, 1H), 3.84 (s, 3H), 2.44 (d, J=0.8 Hz, 3H).

Step 4: Synthesis of Intermediate WX007-5

At −78° C. and under nitrogen atmosphere, intermediate WX007-4 (4.22 g, 25.42 mmol, purity: 97.69%) was dissolved in dichloromethane (40 mL), and a solution of boron tribromide (19.10 g, 76.26 mmol, 7.35 mL) in dichloromethane (10 mL) was added; and the reaction mixture was warmed to 25° C. and stirred and reacted at 25° C. for 5 hours. After completion of the reaction, the reaction mixture was poured into water (100 mL) and extracted with dichloromethane (50 mL×3). The organic phase was combined, washed with saturated brine (50 mL×2), dried over anhydrous sodium sulfate and filtered, and the solvent was removed from the filtrate under reduced pressure. The resulting residue was purified by column chromatography (eluent: petroleum ether/ethyl acetate=20/1-8/1, volume ratio) to obtain intermediate WX007-5. MS-ESI m/z: 148.9 [M+H]$^+$. $^1$H NMR (400 MHz, CDCl$_3$) δ: 7.24 (d, J=8.4 Hz, 1H), 6.89 (d, J=2.4 Hz, 1H), 6.71 (dd, J=2.4, 8.8 Hz, 1H), 6.28 (s, 1H), 4.80 (s, 1H), 2.43 (d, J=0.8 Hz, 3H).

Step 5: Synthesis of Intermediate WX007-6

At room temperature and under nitrogen atmosphere, intermediate WX007-5 (3.08 g, 20.48 mmol, purity: 98.53%) was dissolved in N,N-dimethylformamide (30 mL), and potassium carbonate (5.66 g, 40.97 mmol) was added, and the reaction mixture was stirred and reacted at 0° C. for 0.5 hours. Ethyl bromoacetate (3.42 g, 20.48 mmol, 2.27 mL) was added, and the reaction mixture was stirred and reacted at 25° C. and under nitrogen atmosphere for 12 hours. After completion of the reaction, water (100 mL) was added to the reaction mixture, and extraction with ethyl acetate (50 mL×3) was performed. The organic phase was combined, washed with saturated brine (50 mL×2), dried over anhydrous sodium sulfate and filtered, and the solvent was removed from the filtrate under reduced pressure. The resulting residue was purified by column chromatography (eluent: petroleum ether/ethyl acetate=20/1-10/1, volume ratio) to obtain intermediate WX007-6. MS-ESI m/z: 235.1 [M+H]$^+$. $^1$H NMR (400 MHz, CDCl$_3$) δ: 7.30 (d, J=9.2 Hz, 1H), 6.95 (d, J=2.4 Hz, 1H), 6.86 (dd, J=2.4, 8.8 Hz, 1H), 6.31 (s, 1H), 4.64 (s, 2H), 4.28 (q, J=7.0 Hz, 2H), 2.43 (d, J=0.8 Hz, 3H), 1.31 (t, J=7.2 Hz, 3H).

Step 6: Synthesis of Intermediate WX007-7

At room temperature under nitrogen atmosphere, intermediate WX007-6 (2.10 g, 8.67 mmol, purity: 96.74%) was dissolved in tetrahydrofuran (20 mL), ethanol (10 mL) and water (5 mL), sodium hydroxide (346.91 mg, 8.67 mmol) was added, and the reaction mixture was stirred and reacted at 25° C. for 12 hours. Tetrahydrofuran and ethanol were removed from the reaction mixture under reduced pressure, and water (100 mL) was added to the reaction mixture. The reaction mixture was adjusted to pH 2-3 by adding 2 M hydrochloric acid aqueous (10 mL) and extracted with ethyl acetate (50 mL×3). The organic phase was combined, washed with saturated brine (50 mL×2), dried over anhydrous sodium sulfate and filtered; and the solvent was removed from the filtrate under reduced pressure to obtain intermediate WX007-7. MS-ESI m/z: 207.1 [M+H]$^+$. $^1$H NMR (400 MHz, CDCl$_3$) δ: 7.32 (d, J=8.8 Hz, 1H), 6.98 (d, J=2.8 Hz, 1H), 6.86 (dd, J=2.6, 9.0 Hz, 1H), 6.33 (s, 1H), 4.70 (s, 2H), 2.44 (d, J=0.8 Hz, 3H).

Step 7: Synthesis of Intermediate WX007-8

At 10° C. and under nitrogen atmosphere, ethyl potassium malonate (3.29 g, 19.31 mmol) was dissolved in acetonitrile (20 mL), and a mixture of triethylamine (3.14 g, 31.06 mmol, 4.32 mL) and magnesium chloride (2.16 g, 22.66 mmol, 930.14 µL) was added to the above-mentioned reaction mixture; and the reaction mixture was warmed to 25° C. and stirred and reacted at 25° C. for 2 hours. At 0° C. and under nitrogen atmosphere, intermediate WX007-7 (1.77 g, 8.39 mmol, purity: 97.79%) was dissolved in acetonitrile (10 mL), and N,N-carbonyldiimidazole (1.36 g, 8.39 mmol) and triethylamine (849.43 mg, 8.39 mmol, 1.17 mL) were added; and the reaction mixture was warmed to 25° C. and stirred and reacted at 25° C. for 2 hours. At 0° C. and under nitrogen atmosphere, the reaction mixture was added dropwise to the above-mentioned solution; and the reaction mixture was warmed to 25° C. and stirred and reacted at 25° C. for 10 hours. After completion of the reaction, ice water (100 mL) was added to the reaction mixture, and extraction with ethyl acetate (60 mL×3) was performed. The organic phase was combined, washed with saturated brine (50 mL×2), dried over anhydrous sodium sulfate and filtered, and the solvent was removed from the filtrate under reduced pressure. The resulting residue was purified by column chromatography (eluent: petroleum ether/ethyl acetate=10/1-5/1, volume ratio) to obtain intermediate WX007-8. MS-ESI m/z: 277.0 [M+H]$^+$. $^1$H NMR (400 MHz, CDCl$_3$) δ: 7.31 (d, J=8.8 Hz, 1H), 6.91 (d, J=2.8 Hz, 1H), 6.81 (dd, J=2.8, 8.8 Hz, 1H), 6.32 (t, J=0.8 Hz, 1H), 4.66 (s, 2H), 4.20 (q, J=7.0 Hz, 2H), 3.66 (s, 2H), 2.44 (d, J=1.2 Hz, 3H), 1.26 (t, J=7.2 Hz, 3H).

Step 8: Synthesis of Intermediate WX007-9

At room temperature and under nitrogen atmosphere, intermediate WX007-8 (0.821 g, 2.44 mmol, purity: 82.04%) was dissolved in toluene (10 mL), and polyphosphoric acid (0.300 g) was added; and the reaction mixture was heated to 110° C. and stirred and reacted at 110° C. for 1 hour. After completion of the reaction, the reaction mixture was cooled to room temperature, added water (30 mL) and extracted with ethyl acetate (20 mL×3). The organic phase was combined, washed with saturated brine (10 mL×2), dried over anhydrous sodium sulfate and filtered; and the solvent was removed from the filtrate under reduced pressure. The resulting residue was purified by supercritical fluid chromatography (separation conditions: chromatographic column: ChiralPak AD-3 150×4.6 mm I.D., 3 µm; mobile phase: A: carbon dioxide, B: ethanol (0.05% diethylamine); flow rate: 2.5 mL/min; column temperature: 40° C.; wavelength: 220 nm), and the sample with a retention time of 3.066 min was collected to obtain intermediate WX007-9. MS-ESI m/z: 259.1 [M+H]$^+$. $^1$H NMR (400 MHz, CDCl$_3$) δ: 7.62 (s, 1H), 7.52 (s, 1H), 7.49 (s, 1H), 6.43 (t, J=0.8 Hz, 1H), 4.21 (q, J=7.2 Hz, 2H), 3.72 (d, J=0.8 Hz, 2H), 2.48 (d, J=1.2 Hz, 3H), 1.29 (t, J=7.2 Hz, 3H).

Step 9: Synthesis of WX007

At 0° C. and under nitrogen atmosphere, to a solution of intermediate WX007-9 (0.100 g, 387.19 µmol, purity: 100%) in N,N-dimethylformamide (10 mL), potassium tert-butoxide (43.45 mg, 387.19 µmol) was added, and then acrylamide (27.52 mg, 387.19 µmol) was added; and the reaction mixture was stirred and reacted at 0° C. and under nitrogen atmosphere for 1 hour. After completion of the reaction, the reaction mixture was diluted by adding water (50 mL) and extracted with ethyl acetate (30 mL×3). The organic phase was combined, washed with saturated brine (30 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain target compound WX007. MS-ESI m/z: 284.1 [M+H]$^+$. $^1$H NMR (400 MHz, DMSO-d$_6$) δ: 10.90 (s, 1H), 7.86 (s, 1H), 7.65 (s, 2H), 6.63 (s, 1H), 4.16 (dd, J=5.0, 11.8 Hz, 1H), 2.83-2.70 (m, 1H), 2.65-2.55 (m, 1H), 2.46 (s, 3H), 2.43-2.31 (m, 1H), 2.20-2.08 (m, 1H).

Example 8

WX008

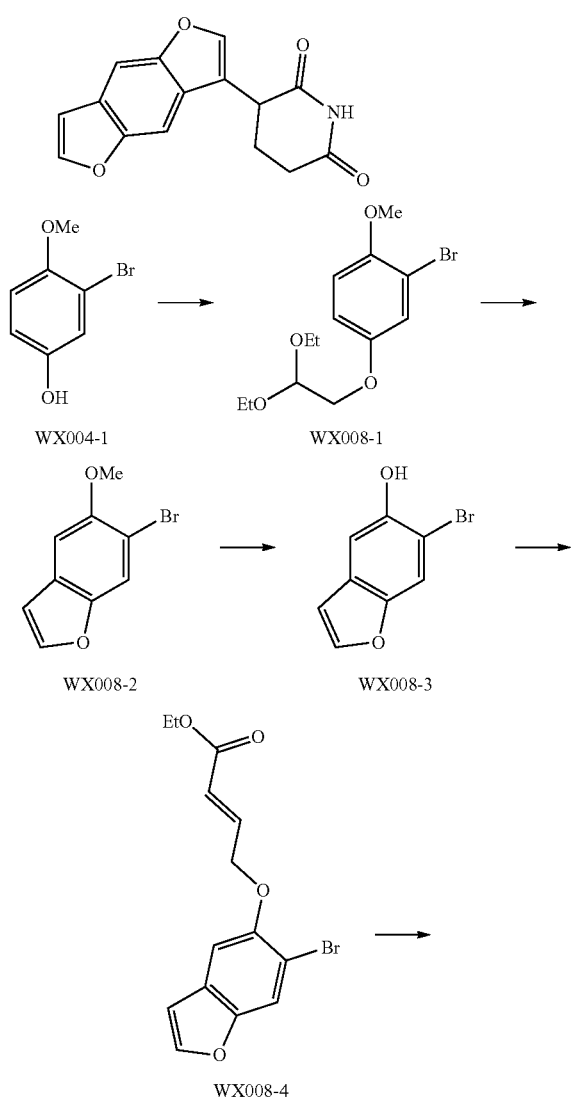

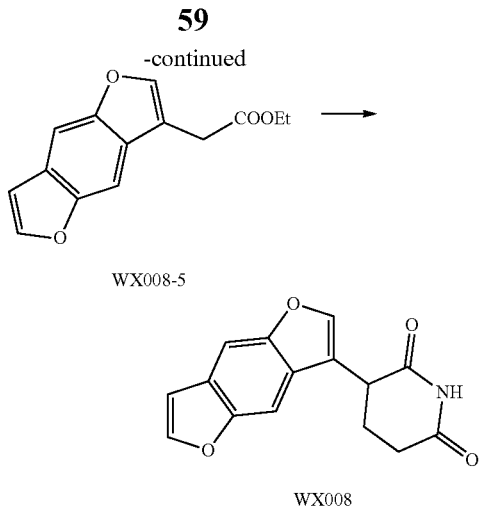

WX008-5

WX008

Step 1: Synthesis of Intermediate WX008-1

At 0° C. and under nitrogen atmosphere, compound WX004-1 (10.00 g, 49.25 mmol) was dissolved in N,N-dimethylformamide (100 mL), and then sodium hydride (2.17 g, 54.18 mmol, purity: 60%) was added in batches; finally, bromoacetaldehyde diethyl acetal (12.62 g, 64.03 mmol, 9.63 mL) was added; and the reaction mixture was heated to 110° C. and stirred and reacted for 12 hours. After completion of the reaction, the reaction mixture was cooled to room temperature, added water (300 mL) and extracted with methyl tert-butyl ether (100 mL×3). The organic phase was combined, dried over anhydrous sodium sulfate and filtered, and the filtrate was concentrated under reduced pressure to remove the solvent. The resulting residue was purified by column chromatography (eluent: petroleum ether/ethyl acetate=1/0-19/1, volume ratio) to obtain intermediate WX008-1. $^1$H NMR (400 MHz, CDCl$_3$) δ: 7.18 (d, J=2.8 Hz, 1H), 6.85 (d, J=2.8 Hz, 1H), 6.84 (s, 1H), 4.80 (t, J=5.4 Hz, 1H), 3.95 (d, J=5.2 Hz, 2H), 3.85 (s, 3H), 3.82-3.71 (m, 2H), 3.70-3.57 (m, 2H), 1.25 (t, J=7.0 Hz, 6H).

Step 2: Synthesis of Intermediate WX008-2

At room temperature and under nitrogen atmosphere, intermediate WX008-1 (10 g, 31.33 mmol) was dissolved in toluene (150 mL), and then polyphosphoric acid (10 g) was added; and the reaction mixture was heated to 110° C. and stirred and reacted for 2 hours. After completion of the reaction, the reaction mixture was cooled to room temperature, and the supernatant was collected and concentrated under reduced pressure to remove the solvent. The resulting residue was purified by column chromatography (eluent: petroleum ether/ethyl acetate=1/0-49/1, volume ratio) to obtain intermediate WX008-2. $^1$H NMR (400 MHz, CDCl$_3$) δ: 7.73 (d, J=0.8 Hz, 1H), 7.59 (d, J=2.0 Hz, 1H), 7.09 (s, 1H), 6.71 (d, J=2.0 Hz, 1H), 3.93 (s, 3H).

Step 3: Synthesis of Intermediate WX008-3

At 10° C. and under nitrogen atmosphere, intermediate WX008-2 (2.8 g, 12.33 mmol) was dissolved in dichloromethane (80 mL) and cooled to −60° C., and boron tribromide (3.71 g, 14.80 mmol, 1.43 mL) was added dropwise; and the reaction mixture was slowly returned to 10° C. and stirred and reacted for 1 hour. After completion of the reaction, the reaction mixture was poured into ice water (20 mL) and extracted with ethyl acetate (100 mL×3). The organic phase was combined, dried over anhydrous sodium sulfate and filtered, and the filtrate was concentrated under reduced pressure to remove the solvent. The resulting residue was purified by column chromatography (eluent: petroleum ether/ethyl acetate=1/0-19/1, volume ratio) to obtain intermediate WX008-3. $^1$H NMR (400 MHz, CDCl$_3$) δ: 7.65 (s, 1H), 7.59 (d, J=2.4 Hz, 1H), 7.22 (s, 1H), 6.68 (dd, J=0.8, 2.0 Hz, 1H), 5.38 (s, 1H).

Step 4: Synthesis of Intermediate WX008-4

At 20° C., intermediate WX008-3 (1.45 g, 6.81 mmol) was dissolved in acetonitrile (20 mL), and then potassium carbonate (2.82 g, 20.42 mmol) and ethyl 4-bromocrotonate (2.23 g, 11.57 mmol, 1.60 mL) were added successively; and the reaction mixture was stirred and reacted at 20° C. for 12 hours. After completion of the reaction, the reaction mixture was directly filtered; the filter cake was washed with ethyl acetate (20 mL×2), and the filtrate was collected and concentrated under reduced pressure to remove the solvent. The resulting residue was purified by column chromatography (eluent: petroleum ether/ethyl acetate=1/0-19/1, volume ratio) to obtain intermediate WX008-4. $^1$H NMR (400 MHz, CDCl$_3$) δ: 7.74 (s, 1H), 7.60 (d, J=2.0 Hz, 1H), 7.12 (dt, J=4.0, 15.6 Hz, 1H), 7.06 (s, 1H), 6.70 (d, J=1.6 Hz, 1H), 6.35 (dt, J=2.0, 15.6 Hz, 1H), 4.77 (dd, J=2.2, 3.8 Hz, 2H), 4.24 (q, J=7.0 Hz, 2H), 1.32 (t, J=7.2 Hz, 3H).

Step 5: Synthesis of Intermediate WX008-5

At room temperature and under nitrogen atmosphere, intermediate WX008-4 (1.3 g, 4.00 mmol) was dissolved in N,N-dimethylformamide (30 mL), and then sodium carbonate (1.06 g, 10.00 mmol), sodium formate (271.91 mg, 4.00 mmol, 215.80 μL), palladium acetate (44.88 mg, 199.91 μmol) and tetrabutylammonium chloride hydrate (1.22 g, 4.40 mmol, 1.23 mL) were added successively; and the reaction mixture was warmed to 80° C. and stirred and reacted for 8 hours. After completion of the reaction, the reaction mixture was cooled to room temperature, added water (100 mL) and extracted with ethyl acetate (50 mL×3). The organic phase was combined, successively washed with half-saturated brine (50 mL×2), dried over anhydrous sodium sulfate and filtered, and the filtrate was concentrated under reduced pressure to obtain a residue. The resulting residue was purified by column chromatography (eluent: petroleum ether/ethyl acetate=1/0-19/1, volume ratio) to obtain intermediate WX008-5. $^1$H NMR (399 MHz, CDCl$_3$) δ: 7.68-7.65 (m, 2H), 7.63 (s, 2H), 6.83 (d, J=1.6 Hz, 1H), 4.22 (q, J=7.2 Hz, 2H), 3.74 (s, 2H), 1.29 (t, J=7.4 Hz, 3H).

Step 6: Synthesis of WX008

At 20° C., intermediate WX008-5 (400 mg, 1.64 mmol) was dissolved in N,N-dimethylformamide (10 mL), and then acrylamide (116.41 mg, 1.64 mmol) and potassium tert-butoxide (183.77 mg, 1.64 mmol) were added successively; and the reaction mixture was stirred and reacted at 20° C. for 1 hour. After completion of the reaction, water (30 mL) was added to the reaction mixture, and extraction with ethyl acetate was performed (30 mL×3). The organic phase was combined, dried over anhydrous sodium sulfate and filtered, and the filtrate was concentrated under reduced pressure to remove the solvent. The resulting residue was purified by column chromatography (eluent: petroleum ether/ethyl acetate=4/1-3/1, volume ratio); and then the resulting residue was purified again by preparative HPLC (mobile phase: acetonitrile/water: acid system: 0.05% HCl) to obtain target compound WX008. MS-ESI m/z: 270.0 [M+H]$^+$. $^1$H NMR (400 MHz, DMSO-d$_6$) δ: 10.91 (s, 1H), 8.00 (d, J=2.4 Hz, 1H), 7.91 (s, 1H), 7.78 (d, J=6.0 Hz, 2H), 7.01 (d, J=1.6 Hz, 1H), 4.18 (dd, J=5.0, 11.8 Hz, 1H), 2.82-2.71 (m, 1H), 2.69-2.55 (m, 1H), 2.46-2.32 (m, 1H), 2.19-2.08 (m, 1H).

Example 9

WX009

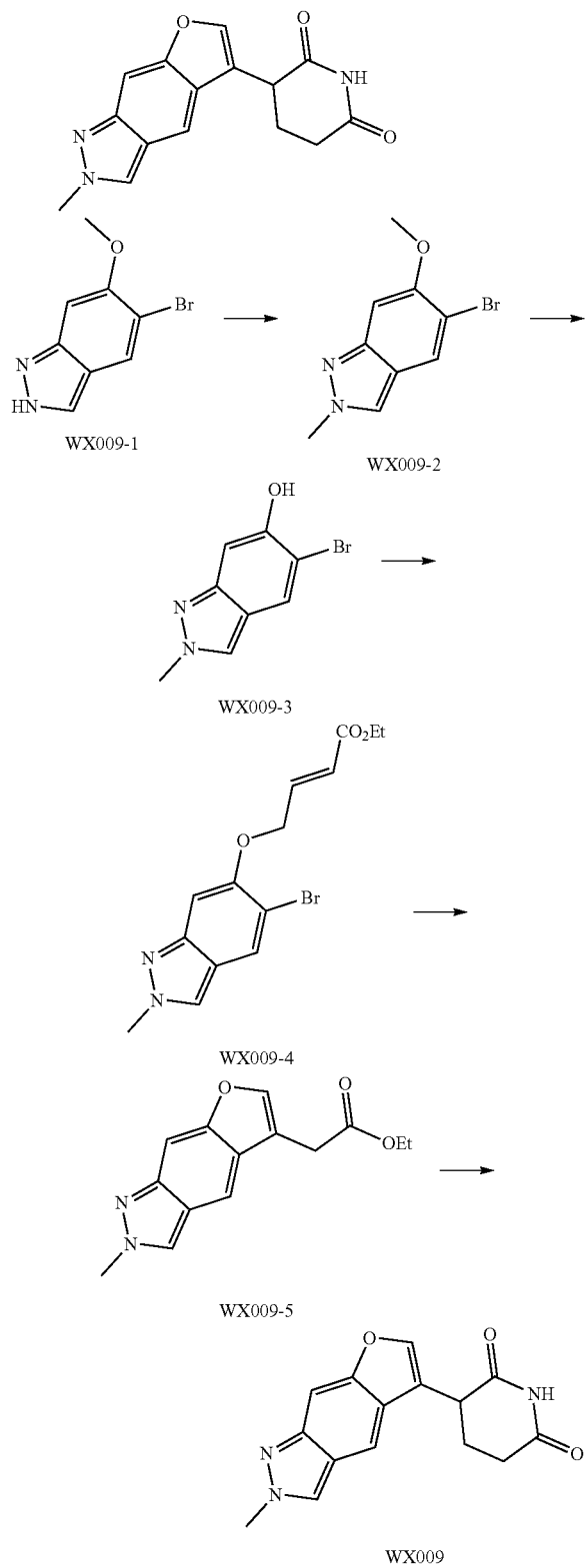

Step 1: Synthesis of Intermediate WX009-2

At room temperature, compound WX009-1 (10 g, 44.04 mmol) was dissolved in ethyl acetate (100 mL), and then trimethyloxonium tetrafluoroborate (7.82 g, 52.85 mmol) was added; and the reaction mixture was stirred and reacted at room temperature for 12 hours. After completion of the reaction, water (100 mL) was added to the reaction mixture, and extraction with ethyl acetate was performed (50 mL×3). The organic phase was combined, dried over anhydrous sodium sulfate and filtered, and the filtrate was concentrated under reduced pressure to remove the solvent. The resulting residue was purified by column chromatography (eluent: petroleum ether/ethyl acetate=4/1-3/2, volume ratio) to obtain intermediate WX009-2. $^1$H NMR (399 MHz, CDCl$_3$) δ: 7.94 (s, 1H), 7.75 (s, 1H), 6.92 (s, 1H), 4.15 (s, 3H), 3.89 (s, 3H).

Step 2: Synthesis of Intermediate WX009-3

At 20° C. and under nitrogen atmosphere, intermediate WX009-2 (6.7 g, 27.79 mmol) was dissolved in dichloromethane (100 mL) and cooled to −60° C.-50° C., and boron tribromide (10.44 g, 41.69 mmol, 4.02 mL) was then added dropwise; and the reaction mixture was warmed to 20° C. and stirred and reacted for 3 hours. After completion of the reaction, the reaction mixture was poured into ice water (200 mL) and extracted with ethyl acetate (200 mL×3). The organic phase was combined, dried over anhydrous sodium sulfate and filtered, and the filtrate was concentrated under reduced pressure to remove the solvent. The resulting residue was stirred with methyl tert-butyl ether (30 mL) at room temperature for 30 minutes, and a solid was precipitated. The solid was filtered, collected and concentrated under reduced pressure to remove the solvent to obtain intermediate WX009-3. $^1$H NMR (400 MHz, DMSO_d$_6$) δ: 8.11 (s, 1H), 7.83 (s, 1H), 7.06 (s, 1H), 6.45 (s, 1H), 4.08 (s, 3H).

Step 3: Synthesis of Intermediate WX009-4

At room temperature and under nitrogen atmosphere, intermediate WX009-3 (2.5 g, 11.01 mmol) was dissolved in acetonitrile (30 mL), and then potassium carbonate (4.57 g, 33.03 mmol) and ethyl 4-bromocrotonate (3.19 g, 16.52 mmol, 2.28 mL) were added successively. The reaction mixture was stirred and reacted at room temperature for 12 hours, and then the reaction mixture was heated to 50° C. and stirred and reacted for 6 hours. After completion of the reaction, the reaction mixture was cooled to room temperature, added water (200 mL) and extracted with ethyl acetate (100 mL×3). The organic phase was combined, successively washed with saturated brine (50 mL), dried over anhydrous sodium sulfate and filtered, and the filtrate was concentrated under reduced pressure to remove the solvent. The resulting residue was purified by column chromatography (eluent: petroleum ether/ethyl acetate=9/1-3/2, volume ratio) to obtain intermediate WX009-4. $^1$H NMR (400 MHz, CDCl$_3$) δ: 7.95 (s, 1H), 7.75 (s, 1H), 7.10 (dt, J=3.8, 15.6 Hz, 1H), 6.89 (s, 1H), 6.35 (dt, J=1.8, 14.0 Hz, 1H), 4.72 (dd, J=2.0, 3.6 Hz, 2H), 4.22 (q, J=7.0 Hz, 2H), 4.15 (s, 3H), 1.31 (t, J=7.2 Hz, 3H).

Step 4: Synthesis of Intermediate WX009-5

At room temperature and under nitrogen atmosphere, intermediate WX009-4 (1.6 g, 4.72 mmol) was dissolved in N,N-dimethylformamide (30 mL), and then sodium carbonate (999.94 mg, 9.43 mmol), sodium formate (320.80 mg, 4.72 mmol), palladium acetate (52.95 mg, 235.86 μmol), and tetrabutylammonium chloride hydrate (1.44 g, 5.19 mmol, 1.45 mL) were added successively; and the reaction mixture was heated to 80° C. and stirred and reacted for 6 hours. After completion of the reaction, the reaction mixture was cooled to room temperature, added water (200 mL) and extracted with ethyl acetate (60 mL×3). The organic phase was combined, dried over anhydrous sodium sulfate and filtered, and the filtrate was concentrated under reduced pressure to remove the solvent. The resulting residue was purified by column chromatography (eluent: petroleum ether/ethyl acetate=1/0-3/2, volume ratio) to obtain intermediate WX009-5. $^1$H NMR (400 MHz, MeOD_$d_4$) δ: 8.23 (s, 1H), 7.69 (s, 1H), 7.67 (s, 1H), 7.63 (s, 1H), 4.23 (s, 3H), 4.18 (q, J=7.2 Hz, 2H), 3.75 (s, 2H), 1.26 (t, J=7.2 Hz, 3H).

Step 5: Synthesis of WX009

At room temperature, intermediate WX009-5 (600 mg, 2.32 mmol) was dissolved in tetrahydrofuran (20 mL), and then acrylamide (165.12 mg, 2.32 mmol) and a solution of potassium tert-butoxide in tetrahydrofuran (1 M, 2.32 mL) were added successively; and the reaction mixture was stirred and reacted at room temperature for 2 hours. After completion of the reaction, the reaction mixture was diluted by adding water (50 mL) and extracted with ethyl acetate (50 mL×3). The organic phase was combined, dried over anhydrous sodium sulfate and filtered, and the filtrate was concentrated under reduced pressure to remove the solvent. The resulting residue was stirred with N,N-dimethylformamide (10 mL) at room temperature for 15 minutes, and a light-yellow solid was precipitated. The solid was filtered and the filter cake was washed with acetonitrile (2 mL×2) and collected to obtain target compound WX009. MS-ESI m/z: 284.1 [M+H]$^+$. $^1$H NMR (400 MHz, DMSO_$d_6$) δ: 10.91 (s, 1H), 8.39 (s, 1H), 7.84 (s, 1H), 7.74 (s, 1H), 7.70 (s, 1H), 4.21 (s, 3H), 4.16 (dd, J=4.8, 11.6 Hz, 1H), 2.82-2.69 (m, 1H), 2.68-2.55 (m, 1H), 2.43-2.30 (m, 1H), 2.19-2.09 (m, 1H).

Example 10

WX010

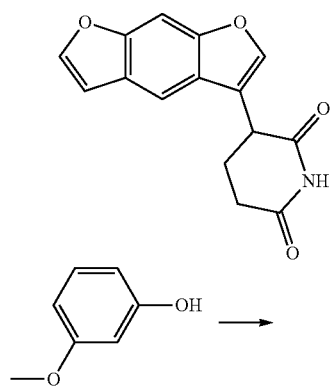

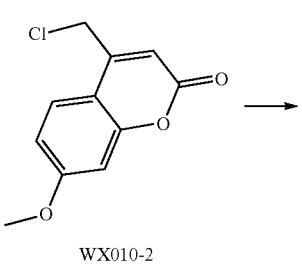

WX010-2

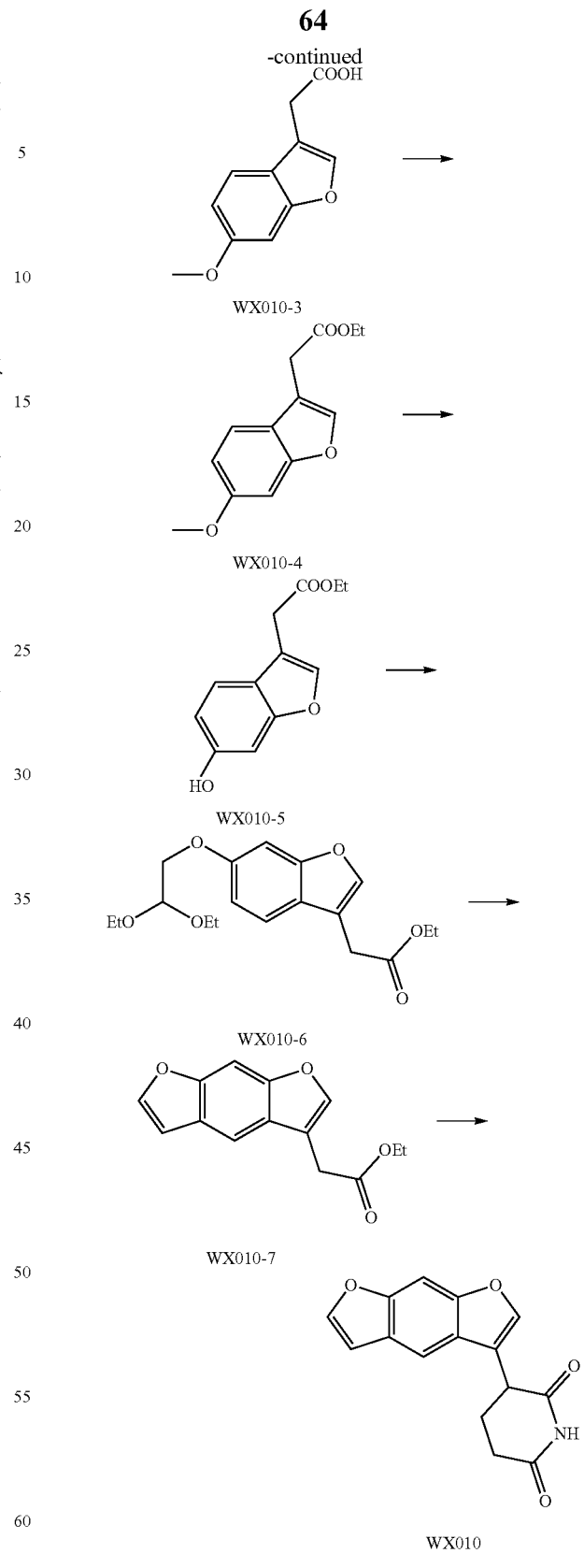

Step 1: Synthesis of Intermediate WX010-2

At room temperature, concentrated sulfuric acid (220.80 g, 2.21 mol, 120 mL, purity: 98%) was added dropwise to ice water (40 mL), and then compound WX010-1 (15 g, 120.83 mmol, 13.04 mL) was added. The reaction mixture was cooled to 5-10° C., and then ethyl 4-chloroacetoacetate (25.85 g, 157.08 mmol, 21.19 mL) was added dropwise; and the reaction mixture was returned to room temperature and stirred and reacted for 12 hours. After completion of the reaction, the reaction mixture was poured into ice water (200 mL), and a light-yellow solid was precipitated. The solid was filtered and collected. Toluene (50 mL) was added, and the solvent was removed by concentration under reduced pressure to obtain intermediate WX010-2.

Step 2: Synthesis of Intermediate WX010-3

At room temperature, sodium hydroxide (16.00 g, 400 mmol) was dissolved in water (200 mL), and intermediate WX010-2 (27 g, 120.19 mmol) was then added; and the reaction mixture was heated to 80° C. and stirred and reacted for 12 hours. After completion of the reaction, the reaction mixture was cooled to room temperature, adjusted to pH 5-6 by adding 2 M hydrochloric acid aqueous and extracted with ethyl acetate (100 mL×3). The organic phase was combined, dried over anhydrous sodium sulfate and filtered; the filtrate and concentrated under reduced pressure to remove the solvent to obtain intermediate WX010-3.

Step 3: Synthesis of Intermediate WX010-4

At room temperature, intermediate WX010-3 (20 g, 97.00 mmol) was dissolved in ethanol (200 mL), and then concentrated sulfuric acid (5.52 g, 55.16 mmol, 3 mL, purity: 98%) was added; and the reaction mixture was heated to 80° C. and stirred and reacted for 4 hours. After completion of the reaction, the reaction mixture was cooled to room temperature, and concentrated under reduced pressure to remove ethanol; the resulting residue was diluted with water (200 mL) and ethyl acetate (200 mL); after separation, the organic phase was collected, and the aqueous phase was extracted with ethyl acetate (100 mL×3). The organic phase was combined, dried over anhydrous sodium sulfate and filtered, and the filtrate was concentrated under reduced pressure to obtain a residue. The resulting residue was purified by column chromatography (eluent: petroleum ether/ethyl acetate=1/0-19/1, volume ratio) to obtain intermediate WX010-4. $^1$H NMR (400 MHz, CDCl$_3$) δ: 7.54 (s, 1H), 7.44 (d, J=8.8 Hz, 1H), 7.01 (d, J=2.0 Hz, 1H), 6.90 (dd, J=2.0, 8.4 Hz, 1H), 4.19 (q, J=7.2 Hz, 2H), 3.86 (s, 3H), 3.67 (s, 2H), 1.28 (t, J=7.0 Hz, 3H).

Step 4: Synthesis of Intermediate WX010-5

At 20° C. and under nitrogen atmosphere, intermediate WX010-4 (14.2 g, 60.62 mmol) was dissolved in dichloromethane (200 mL) and cooled to −60° C., and boron tribromide (22.78 g, 90.93 mmol, 8.76 mL) was then added dropwise; and the reaction mixture was returned to 20° C. and stirred and reacted for 1 hour. After completion of the reaction, the reaction mixture was poured into ice water (500 mL) and extracted with dichloromethane (200 mL×3). The organic phase was combined, dried over anhydrous sodium sulfate and filtered, and the filtrate was concentrated under reduced pressure to obtain a residue. The resulting residue was purified by column chromatography (eluent: petroleum ether/ethyl acetate=1/0-9/1, volume ratio) to obtain intermediate WX010-5. $^1$H NMR (400 MHz, CDCl$_3$) δ: 7.51 (s, 1H), 7.35 (d, J=8.4 Hz, 1H), 6.90 (d, J=2.0 Hz, 1H), 6.75 (dd, J=1.6, 8.4 Hz, 1H), 5.64 (s, 1H), 4.21 (q, J=7.0 Hz, 2H), 3.67 (s, 2H), 1.29 (t, J=7.2 Hz, 3H).

Step 5: Synthesis of Intermediate WX010-6

At room temperature and under nitrogen atmosphere, intermediate WX010-5 (5 g, 22.70 mmol) was dissolved in N,N-dimethylformamide (50 mL), and potassium carbonate (6.28 g, 45.41 mmol) and bromoacetaldehyde diethyl acetal (6.71 g, 34.06 mmol, 5.12 mL) were then added; and the reaction mixture was heated to 100° C. and stirred and reacted for 24 hours. After completion of the reaction, the reaction mixture was cooled to room temperature, added water (300 mL) and extracted with ethyl acetate (100 mL×3). The organic phase was combined, successively washed with half-saturated brine (100 mL×3), dried over anhydrous sodium sulfate and filtered, and the filtrate was concentrated under reduced pressure to remove the solvent. The resulting residue was purified by column chromatography (eluent: petroleum ether/ethyl acetate=1/0-9/1, volume ratio) to obtain intermediate WX010-6. $^1$H NMR (400 MHz, CDCl$_3$) δ: 7.54 (s, 1H), 7.43 (d, J=8.8 Hz, 1H), 7.03 (d, J=2.4 Hz, 1H), 6.93 (dd, J=2.2, 8.6 Hz, 1H), 4.87 (t, J=5.2 Hz, 1H), 4.19 (q, J=7.2 Hz, 2H), 4.05 (d, J=5.2 Hz, 2H), 3.84-3.75 (m, 2H), 3.71-3.59 (m, 4H), 1.33-1.19 (m, 9H).

Step 6: Synthesis of Intermediate WX010-7

At room temperature and under nitrogen atmosphere, intermediate WX010-6 (2 g, 5.95 mmol) was dissolved in toluene (50 mL), and then polyphosphoric acid (3 g) was added; and the reaction mixture was heated to 100° C. and stirred and reacted for 15 minutes. After completion of the reaction, the reaction mixture was directly poured, and the supernatant was collected and concentrated under reduced pressure to remove the solvent. The resulting residue was purified by column chromatography (eluent: petroleum ether/ethyl acetate=1/0-9/1, volume ratio); the resulting residue was purified by preparative HPLC (mobile phase: acetonitrile/water; acid system: 0.05% HCl) and concentrated under reduced pressure to remove acetonitrile; and the aqueous phase was extracted with ethyl acetate (100 mL×3). The organic phase was combined, dried over anhydrous sodium sulfate and filtered, and the solvent was removed by concentration under reduced pressure to obtain intermediate WX010-7. $^1$H NMR (399 MHz, CDCl$_3$) δ: 7.69 (s, 1H), 7.67-7.63 (m, 2H), 7.61 (s, 1H), 6.84 (d, J=2.0 Hz, 1H), 4.21 (q, J=6.8 Hz, 2H), 3.74 (s, 2H), 1.29 (t, J=7.2 Hz, 3H).

Step 7: Synthesis of WX010

At room temperature, intermediate WX010-7 (500 mg, 2.05 mmol) was dissolved in N,N-dimethylformamide (10 mL), and then acrylamide (145.51 mg, 2.05 mmol) and potassium tert-butoxide (229.71 mg, 2.05 mmol) were added successively; and the reaction mixture was stirred and reacted at room temperature for hours. After completion of the reaction, the reaction mixture was diluted by adding water (20 mL) and extracted with ethyl acetate (20 mL×3). The organic phase was combined, successively washed with half-saturated brine (20 mL×3), dried over anhydrous sodium sulfate and filtered, and the filtrate was concentrated under reduced pressure to remove the solvent. The resulting residue was purified by preparative HPLC (mobile phase: acetonitrile/water; acid system: 0.05% HCl) to obtain target compound WX010. MS-ESI m/z: 270.0 [M+H]$^+$. $^1$H NMR (400 MHz, DMSO_d$_6$) δ: 10.93 (s, 1H), 7.99 (d, J=2.4 Hz, 1H), 7.91 (s, 1H), 7.85 (s, 1H), 7.77 (s, 1H), 7.01 (d, J=2.4 Hz, 1H), 4.18 (dd, J=5.0, 11.8 Hz, 1H), 2.82-2.70 (m, 1H), 2.69-2.55 (m, 1H), 2.44-2.30 (m, 1H), 2.19-2.10 (m, 1H).

Example 11

WX011

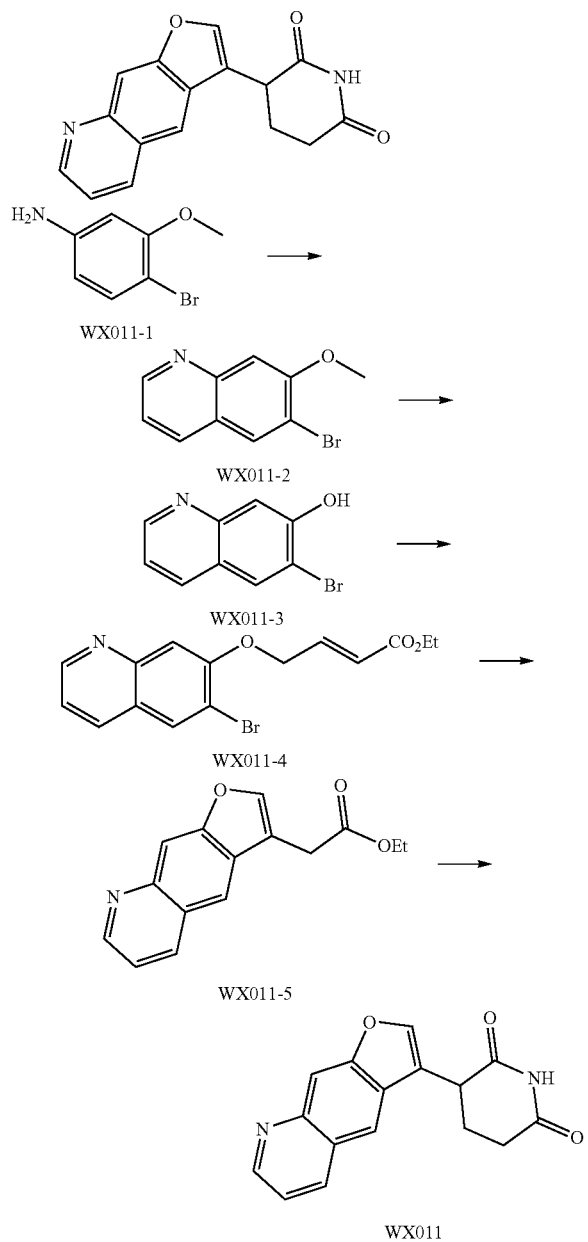

Step 1: Synthesis of Intermediate WX011-2

At room temperature and under nitrogen atmosphere, concentrated sulfuric acid (37.15 g, 371.20 mmol, purity: 98%) was dissolved in water (20 mL), and 3-nitrobenzenesulfonic acid hydrate (15.99 g, 78.69 mmol) and glycerine (25.30 g, 274.69 mmol, 20.57 mL) were added. The reaction mixture was warmed to 110° C., and then compound WX011-1 (15 g, 74.24 mmol), water (20 mL), concentrated sulfuric acid (20 mL, purity: 98%) and glycerine (20 mL) were added; and the reaction mixture was warmed to 140° C. and stirred and reacted for 3 hours. After completion of the reaction, the reaction mixture was poured into ice water (500 mL), adjusted to pH 8 with 2 N sodium hydroxide aqueous solution, and then extracted with ethyl acetate (500 mL×3). The organic phase was combined, dried over anhydrous sodium sulfate and filtered, and concentrated under reduced pressure to obtain a residue. The resulting residue was purified by column chromatography (eluent: petroleum ether/ethyl acetate=1/0-6/1, volume ratio) to obtain intermediate WX011-2. $^1$H NMR (400 MHz, CDCl$_3$) δ: 8.85 (dd, J=1.6, 4.4 Hz, 1H), 8.04 (s, 1H), 8.01 (dd, J=1.0, 8.2 Hz, 1H), 7.46 (s, 1H), 7.30 (dd, J=4.4, 8.0 Hz, 1H), 4.04 (s, 3H).

Step 2: Synthesis of Intermediate WX011-3

At room temperature and under nitrogen atmosphere, intermediate WX011-2 (12.6 g, 52.92 mmol) was dissolved in dichloromethane (1500 mL) and cooled to −20° C.; boron tribromide (66.29 g, 264.62 mmol) was added; and the reaction mixture was stirred and reacted at −20° C. for 1 hour. Then, the reaction mixture was stirred and reacted at 20° C. for 12 hours. At 20° C., boron tribromide (13.5 g) was added; and the reaction mixture was stirred and reacted at 20° C. for 12 hours. At 0° C., boron tribromide (13.5 g) was added; and the reaction mixture was stirred and reacted at room temperature for 12 hours. After completion of the reaction, the reaction mixture was poured into ice water (2000 mL) and filtered; the filter cake was dissolved in water (4000 mL), adjusted to pH 8-9 with saturated sodium bicarbonate solution, and then extracted with 2-methyl tetrahydrofuran (1500 mL×3). The organic phase was combined, successively washed with saturated brine (200 mL×2), dried over anhydrous sodium sulfate and filtered, and the filtrate was concentrated under reduced pressure to remove the solvent. The resulting residue was purified by preparative HPLC (mobile phase: acetonitrile/water; acid system: 0.05% HCl) to obtain intermediate WX011-3. $^1$H NMR (400 MHz, DMSO_d$_6$) δ: 12.53 (s, 1H), 9.07 (dd, 5.6 Hz, 1H), 8.86 (d, J=8.4 Hz, 1H), 8.65 (s, 1H), 7.81-7.74 (m, 2H).

Step 3: Synthesis of Intermediate WX011-4

At 20° C. and under nitrogen atmosphere, intermediate WX011-3 (2.22 g, 9.91 mmol) was dissolved in acetonitrile (50 mL), and then potassium carbonate (6.85 g, 49.54 mmol) and ethyl 4-bromocrotonate (2.42 g, 9.41 mmol) were added; and the reaction mixture was stirred and reacted at 20° C. for 12 hours. After completion of the reaction, the reaction mixture was poured into water (100 mL) and diluted by adding ethyl acetate (80 mL). After separation, the organic phase was collected, and the aqueous phase was extracted with ethyl acetate (80 mL×3). The organic phase was combined, washed with saturated brine (50 mL×2), dried over anhydrous sodium sulfate and filtered, and the filtrate was concentrated under reduced pressure to remove the solvent. The resulting residue was purified by column chromatography (eluent: petroleum ether/ethyl acetate=1/0-6/1, volume ratio) to obtain intermediate WX011-4.

Step 4: Synthesis of Intermediate WX011-5

At room temperature and under nitrogen atmosphere, intermediate WX011-4 (1 g, 2.97 mmol) was dissolved in N,N-dimethylformamide (50 mL); sodium carbonate (493.78 mg, 5.95 mmol) and chloro(2-dicyclohexylphosphino-2,4,6-triisopropyl-1,1-biphenylyl)[2-(2-amino-1,1-biphenyl)]palladium (II) (468.08 mg, 594.92 μmol) were added successively; and the reaction mixture was warmed to 80° C. and stirred and reacted for 16 hours. Chloro(2-dicyclohexylphosphino-2,4,6-triisopropyl-1,1-biphenylyl) [2-(2-amino-1,1-biphenyl)]palladium (II) (60 mg) was added, and the reaction mixture was warmed to 80° C. and stirred and reacted for 12 hours. After completion of the reaction, the reaction mixture was cooled to room temperature, and half-saturated brine (400 mL) and ethyl acetate (200 mL) were added to the reaction mixture. After separation, the organic phase was collected, and the aqueous phase was extracted with ethyl acetate (100 mL×3). The organic phase was combined, washed with half-saturated brine (100 mL×2), then washed with saturated brine (100 mL×2), dried over anhydrous sodium sulfate and filtered, and the filtrate was concentrated under reduced pressure to remove the solvent. The resulting residue was purified by column chromatography (eluent: petroleum ether/ethyl acetate=1/0-4/1, volume ratio) and then purified again by preparative HPLC (mobile phase: acetonitrile/water; acid system: 0.05% HCl) to obtain intermediate WX011-5. $^1$H NMR (400 MHz, DMSO_d$_6$) δ: 9.24 (dd, J=1.2, 4.8 Hz, 1H), 9.16 (d, J=8.4 Hz, 1H), 8.58 (s, 1H), 8.47 (s, 1H), 8.34 (s, 1H), 7.93 (dd, J=5.0, 8.6 Hz, 1H), 4.16 (q, J=7.2 Hz, 2H), 3.99 (s, 2H), 1.22 (t, J=7.2 Hz, 3H).

Step 5: Synthesis of WX011

At 20° C. and under nitrogen atmosphere, intermediate WX011-5 (120 mg, 470.09 μmol) was dissolved in N,N-dimethylformamide (2 mL), and then acrylamide (33.41 mg, 470.09 μmol) and potassium tert-butoxide (79.13 mg, 705.14 μmol) were added successively; and the reaction mixture was stirred and reacted at 20° C. for 2 hours. After completion of the reaction, the reaction mixture was adjusted to pH 6-7 by adding dropwise 2M hydrochloric acid aqueous, and the resulting residue was purified by preparative HPLC (mobile phase: acetonitrile/water; alkalic system: 10 mM NH$_4$HCO$_3$) to obtain target compound WX011. MS-ESI m/z: 281.1 [M+H]$^+$. $^1$H NMR (400 MHz, DMSO_d$_6$) δ: 10.98 (s, 1H), 8.90 (s, 1H), 8.46 (d, J=8.0 Hz, 1H), 8.22 (s, 1H), 8.14 (d, J=2.8 Hz, 2H), 7.48 (dd, J=3.6, 8.0 Hz, 1H), 4.28 (dd, J=4.2, 12.2 Hz, 1H), 2.88-2.74 (m, 1H), 2.69-2.58 (m, 1H), 2.46-2.31 (m, 1H), 2.24-2.12 (m, 1H).

Example 12

WX012

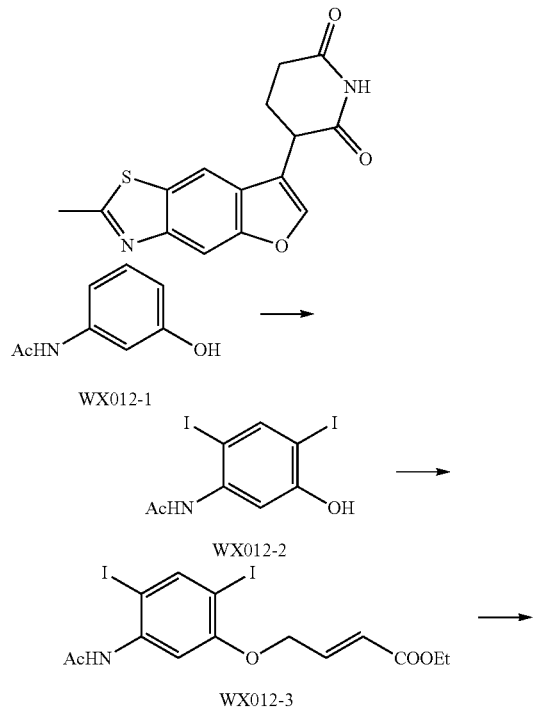

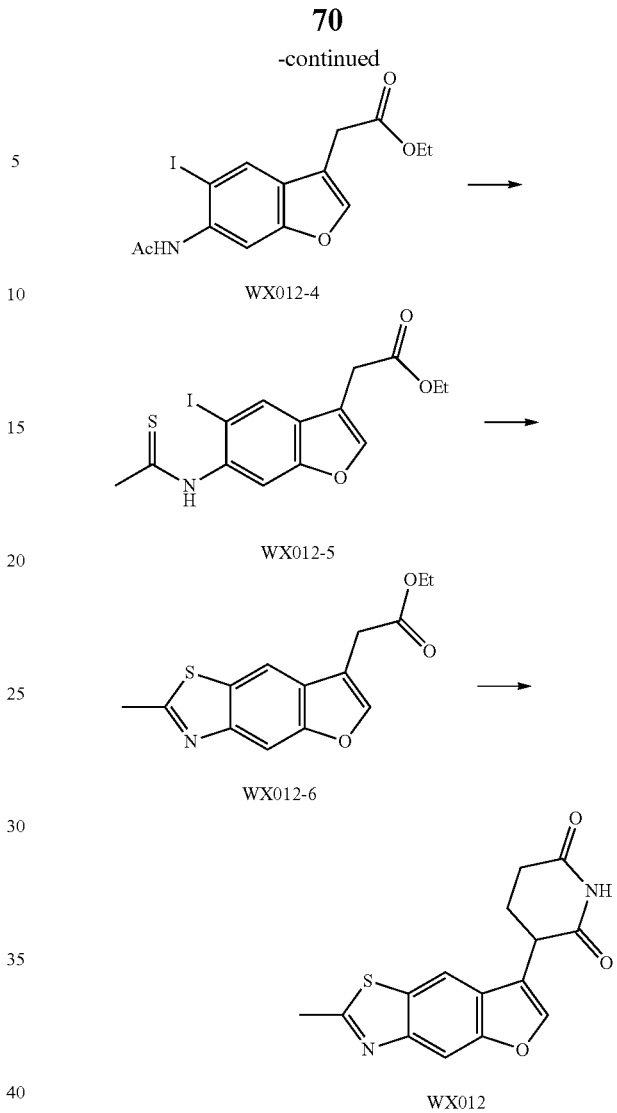

Step 1: Synthesis of Intermediate WX012-2

At 0° C., compound WX012-1 (5 g, 33.08 mmol) was dissolved in dichloromethane (50 mL), and then N-iodosuccinimide (14.88 g, 66.15 mmol) was added; and the reaction mixture was returned to room temperature and stirred and reacted for 12 hours. After completion of the reaction, the reaction mixture was filtered, and the filter cake was collected and concentrated under reduced pressure to remove the solvent to obtain WX012-2. $^1$H NMR (400 MHz, DMSO_d6) δ: 10.56 (s, 1H), 9.19-9.06 (m, 1H), 7.96 (s, 1H), 7.08 (s, 1H), 1.98 (s, 3H).

Step 2: Synthesis of Intermediate WX012-3

At 20° C., intermediate WX012-2 (4.7 g, 11.66 mmol) and ethyl 4-bromocrotonate (3.00 g, 11.66 mmol, 2.14 mL) were dissolved in acetonitrile (70 mL), and then potassium carbonate (4.03 g, 29.16 mmol) was added; and the reaction mixture was stirred and reacted at 20° C. for 12 hours. After completion of the reaction, the reaction mixture was poured into water (100 mL) and filtered; and the filter cake was collected, washed with water (100 mL) and concentrated under reduced pressure to remove the solvent to obtain intermediate WX012-3.

Step 3: Synthesis of Intermediate WX012-4

At 20° C., intermediate WX012-3 (2.9 g, 5.63 mmol) was dissolved in N,N-dimethylformamide (90 mL), and then sodium formate (585.75 mg, 5.63 mmol), sodium carbonate (1.49 g, 14.08 mmol), benzyltriethyl ammonium chloride (1.41 g, 6.19 mmol) and palladium acetate (63.20 mg, 281.51 µmol) were added successively; and the reaction mixture was stirred and reacted at 20° C. for 3 hours. After completion of the reaction, the reaction mixture was poured into ice water (300 mL) and extracted with ethyl acetate (400 mL×3). The organic phase was combined, dried over anhydrous sodium sulfate and filtered, and the filtrate was concentrated under reduced pressure to remove the solvent. The resulting residue was purified by column chromatography (eluent: petroleum ether/ethyl acetate=1/0-3/1, volume ratio) to obtain intermediate WX012-4.

Step 4: Synthesis of Intermediate WX012-5

At room temperature and under nitrogen atmosphere, intermediate WX012-4 (0.33 g, 852.34 µmol) was dissolved in tetrahydrofuran (10 mL), and then Lawesson's reagent (344.74 mg, 852.34 µmol) was added; and the reaction mixture was heated to 55° C. and stirred and reacted for 12 hours. After completion of the reaction, the reaction mixture was concentrated under reduced pressure to remove the solvent. The resulting residue was purified by column chromatography (eluent: petroleum ether/ethyl acetate=10/1, volume ratio) to obtain intermediate WX012-5.

Step 5: Synthesis of Intermediate WX012-6

At room temperature and under nitrogen atmosphere, intermediate WX012-5 (250 mg, 619.99 µmol) was dissolved in N,N-dimethylformamide (4 mL), and wet palladium carbon (0.25 g, purity: 10%) was then added; and the reaction mixture was stirred and reacted at room temperature for 12 hours. After completion of the reaction, the reaction mixture was filtered, and the filtrate was collected, added water (20 mL) and extracted with ethyl acetate (20 mL×3). The organic phase was combined, successively washed with half-saturated brine (10 mL×3), dried over anhydrous sodium sulfate and filtered, and the filtrate was concentrated under reduced pressure to remove the solvent. The resulting residue was purified by column chromatography (eluent: petroleum ether/ethyl acetate=1/0 to 5/1, volume ratio) to obtain intermediate WX012-6. $^1$H NMR (400 MHz, CDCl$_3$) δ: 8.04 (s, 1H), 7.96 (s, 1H), 7.71 (s, 1H), 4.21 (q, J=7.2 Hz, 2H), 3.74 (d, J=0.8 Hz, 2H), 2.86 (s, 3H), 1.28 (t, J=7.0 Hz, 3H).

Step 6: Synthesis of WX012

At room temperature and under nitrogen atmosphere, intermediate WX012-6 (40 mg, 145.28 µmol) was dissolved in N,N-dimethylformamide (1 mL), and then acrylamide (10.33 mg, 145.28 µmol) and potassium tert-butoxide (16.30 mg, 145.28 µmol) were added successively; and the reaction mixture was stirred and reacted at room temperature for 1 hour. After completion of the reaction, water (10 mL) was added to the reaction mixture, and extraction with ethyl acetate was performed (20 mL×2). The organic phase was combined, dried over anhydrous sodium sulfate and filtered, and the filtrate was concentrated under reduced pressure to remove the solvent. The resulting residue was purified by preparative HPLC (mobile phase: acetonitrile/water; neutral system: 10 mM NH$_4$HCO$_3$) to obtain target compound WX012. MS-ESI m/z: 301.0 [M+H]$^+$. $^1$H NMR (400 MHz, DMSO_d$_6$) δ: 10.91 (s, 1H), 8.22 (s, 1H), 8.10 (s, 1H), 8.00 (s, 1H), 4.19 (dd, J=5.0, 12.2 Hz, 1H), 2.81 (s, 3H), 2.79-2.71 (m, 1H), 2.64-2.57 (m, 1H), 2.44-2.36 (m, 1H), 2.19-2.09 (m, 1H).

Example 13

WX013

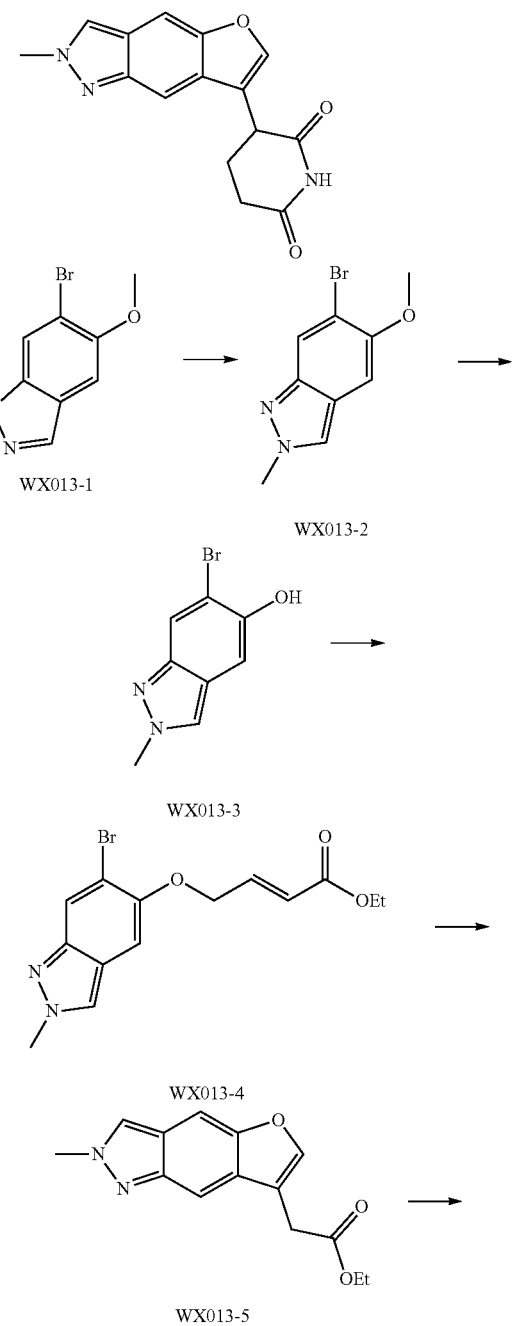

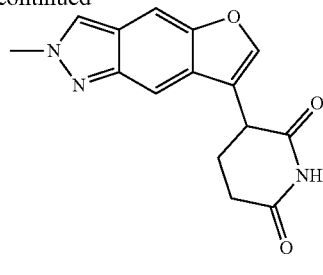

WX013

Step 1: Synthesis of Intermediate WX013-2

At room temperature and under nitrogen atmosphere, compound WX013-1 (10 g, 44.04 mmol) was dissolved in tetrahydrofuran (100 mL); potassium tert-butoxide (7.41 g, 66.06 mmol) was added in batches to the above-mentioned solution, and then iodomethane (17.19 g, 121.11 mmol, 7.54 mL) was added dropwise to the above-mentioned reaction mixture; and the reaction mixture was stirred and reacted at 20° C. for 2 hours. After completion of the reaction, ethyl acetate (200 mL) and deionized water (200 mL) were added to the reaction mixture. The organic phase was separated, washed with saturated brine (100 mL×2), dried over anhydrous sodium sulfate and filtered; and the solvent was removed from the filtrate under reduced pressure. The resulting residue was purified by column chromatography (eluent: petroleum ether/ethyl acetate=5:1, volume ratio) to obtain intermediate WX013-2. MS-ESI m/z: 240.6 [M+H]$^+$, 242.6 [M+H+2]$^+$.

Step 2: Synthesis of Intermediate WX013-3

At room temperature and under nitrogen atmosphere, intermediate WX013-2 (5 g, 20.74 mmol) was dissolved in dichloromethane (100 mL); boron tribromide (15.59 g, 62.22 mmol, 6.00 mL) was slowly added dropwise to the above-mentioned reaction mixture; and the reaction mixture was stirred and reacted at 20° C. for 12 hours. After completion of the reaction, water (50 mL) was added to the reaction mixture, and extraction with ethyl acetate (200 mL) was performed. The organic phase was separated, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=1:1, volume ratio) to obtain intermediate WX013-3. MS-ESI m/z: 226.7 [M+H]$^+$, 228.7 [M+H+2]$^+$.

Step 3: Synthesis of Intermediate WX013-4

At room temperature and under nitrogen atmosphere, intermediate WX013-3 (1.0 g, 4.40 mmol), ethyl 4-bromocrotonate (1.28 g, 6.61 mmol, 910.90 μL) and potassium carbonate (1.22 g, 8.81 mmol) were added to N,N-dimethylformamide (30 mL); and the reaction mixture was stirred and reacted at room temperature for 12 hours. After completion of the reaction, water (50 mL) was added to the reaction mixture, and extraction with ethyl acetate (100 mL) was performed. The organic phase was separated, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=1:1, volume ratio) to obtain intermediate WX013-4. MS-ESI m/z: 338.9 [M+H]$^+$, 340.9 [M+H+2]$^+$. $^1$H NMR (400 MHz, CDCl$_3$) δ: 7.97 (s, 1H), 7.76 (s, 1H), 7.15-7.10 (m, 1H), 6.92 (s, 1H), 6.39-6.34 (m, 1H), 4.78-4.74 (m, 2H), 4.24 (q, J=14.4 Hz, 2H), 4.18 (s, 3H), 1.32 (t, J=7.2 Hz, 3H).

Step 4: Synthesis of Intermediate WX013-5

At room temperature and under nitrogen atmosphere, intermediate WX013-4 (0.9 g, 2.23 mmol), palladium acetate (50.04 mg, 222.89 μmol), tetrabutylammonium chloride (743.33 mg, 2.67 mmol), sodium formate (151.58 mg, 2.23 mmol) and sodium carbonate (590.60 mg, 5.57 mmol) were dissolved in N,N-dimethylformamide (50 mL); and the reaction mixture was heated to 80° C. and stirred and reacted for 2 hours. After completion of the reaction, water (50 mL) was added to the reaction mixture, and extraction with ethyl acetate (100 mL) was performed. The organic phase was separated, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=1:1, volume ratio) to obtain intermediate WX013-5. MS-ESI m/z: 258.9 [M+H]$^+$.

Step 5: Synthesis of WX013

At 0° C.-5° C. and under nitrogen atmosphere, intermediate WX013-5 (0.3 g, 1.03 mmol) was dissolved in N,N-dimethylformamide (10 mL); potassium tert-butoxide (116.00 mg, 1.03 mmol) and acrylamide (73.48 mg, 1.03 mmol) were added successively; and the reaction mixture was stirred at 0° C.-5° C. for 1 hour. After completion of the reaction, water (20 mL) was added to the reaction mixture, and extraction with ethyl acetate (20 mL) was performed. The organic phase was separated, washed with saturated brine (20 mL×2), dried over anhydrous sodium sulfate and filtered, and the solvent was removed from the filtrate under reduced pressure. The resulting residue was purified by preparative HPLC (mobile phase: acetonitrile/water; acid system: 0.05% HCl) to obtain target compound WX013. $^1$H NMR (400 MHz, DMSO-d$_6$) δ: 10.92 (s, 1H), 8.41 (s, 1H), 7.85 (s, 1H), 7.75 (s, 1H), 7.70 (s, 1H), 4.22 (s, 3H), 4.17 (dd, J=4.6, 12.2 Hz, 1H), 2.72-2.50 (m, 2H), 2.34-2.30 (m, 1H), 2.19-2.09 (m, 1H).

Example 14

WX014

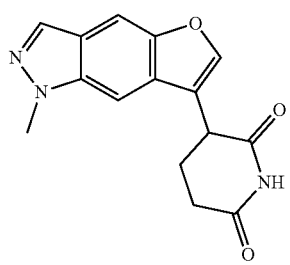

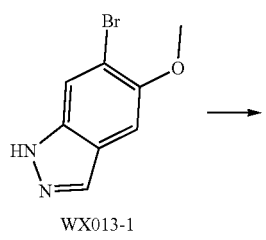

WX013-1

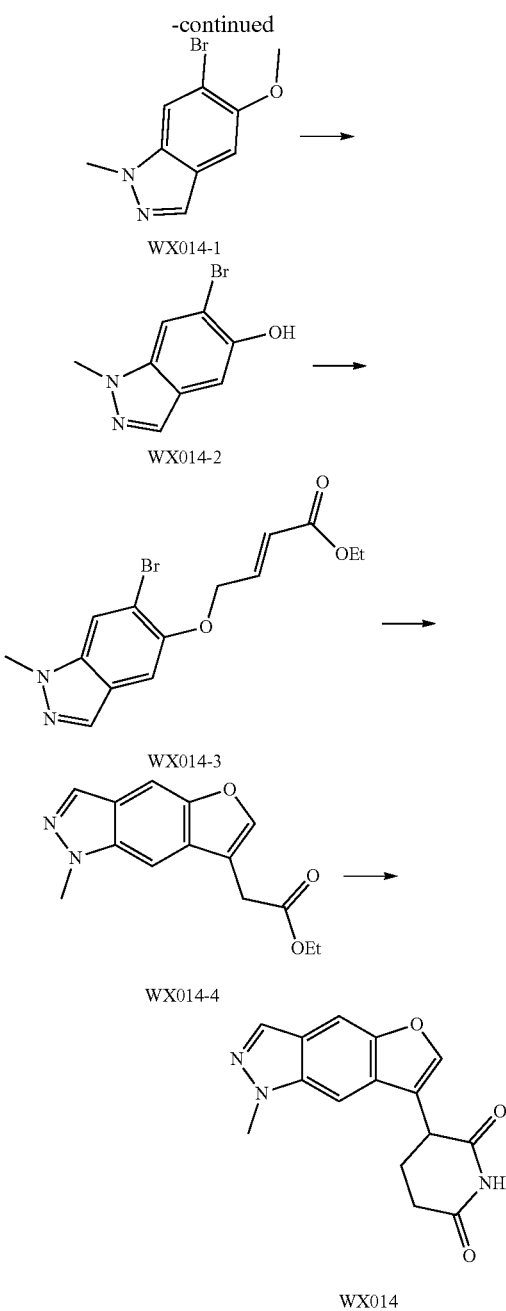

Step 1: Synthesis of Intermediate WX014-1

At room temperature and under nitrogen atmosphere, compound WX013-1 (10 g, 44.04 mmol) was dissolved in tetrahydrofuran (100 mL); potassium tert-butoxide (7.41 g, 66.06 mmol) was added in batches to the above-mentioned solution, and then iodomethane (17.19 g, 121.11 mmol, 7.54 mL) was added dropwise to the above-mentioned reaction mixture; and the reaction mixture was stirred and reacted at room temperature for 2 hours. After completion of the reaction, ethyl acetate (200 mL) and deionized water (200 mL) were added to the reaction mixture. The organic phase was separated, washed with saturated brine (100 mL×2), dried over anhydrous sodium sulfate and filtered; and the solvent was removed from the filtrate under reduced pressure. The resulting residue was purified by column chromatography (eluent: petroleum ether/ethyl acetate=5:1, volume ratio) to obtain intermediate WX014-1. MS-ESI m/z: 240.7 [M+H]$^+$, 242.7 [M+H+2]$^+$.

Step 2: Synthesis of Intermediate WX014-2

At room temperature and under nitrogen atmosphere, intermediate WX014-1 (0.13 g, 539.23 μmol) was dissolved in toluene (10 mL) and aluminum trichloride (143.80 mg, 1.08 mmol) was added; and the reaction mixture was heated to 110° C. and stirred and reacted for 12 hours. After completion of the reaction, water (30 mL) was added to the reaction mixture, and extraction with ethyl acetate (20 mL×3) was performed. The organic phase was combined, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=1:1, volume ratio) to obtain intermediate WX014-2. MS-ESI m/z: 226.8 [M+H]$^+$, 228.8 [M+H+2]$^+$. $^1$H NMR (400 MHz, CDCl$_3$) δ: 7.86 (s, 1H), 7.60 (s, 1H), 7.30 (s, 1H), 5.43 (s, 1H), 4.03 (s, 3H).

Step 3: Synthesis of Intermediate WX014-3

At room temperature and under nitrogen atmosphere, intermediate WX014-2 (0.09 g, 396.38 μmol) was dissolved in N,N-dimethylformamide (10 mL); potassium carbonate (109.56 mg, 792.75 μmol) and ethyl 4-bromocrotonate (114.77 mg, 594.56 μmol, 81.98 μL) were added; and the reaction mixture was stirred and reacted at room temperature for 12 hours. After completion of the reaction, water (50 mL) was added to the reaction mixture, and extraction with ethyl acetate (50 mL) was performed. The organic phase was separated, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=3:1, volume ratio) to obtain intermediate WX014-3. MS-ESI m/z: 338.9 [M+H]$^+$, 340.9 [M+H]$^+$. $^1$H NMR (400 MHz, CDCl$_3$) δ: 7.86 (s, 1H), 7.68 (s, 1H), 7.16-7.09 (m, 2H), 6.38-6.33 (m, 1H), 4.78 (t, J=2.4 Hz, 2H), 4.24 (q, J=14.4 Hz, 2H), 4.04 (s, 3H), 1.32 (t, J=7.2 Hz, 3H).

Step 4: Synthesis of Intermediate WX014-4

At room temperature and under nitrogen atmosphere, intermediate WX014-3 (0.095 g, 280.08 μmol), palladium acetate (6.29 mg, 28.01 μmol), tetrabutylammonium chloride (93.41 mg, 336.10 μmol), sodium formate (19.05 mg, 280.08 μmol) and sodium carbonate (74.22 mg, 700.21 μmol) were dissolved in N,N-dimethylformamide (10 mL); and the reaction mixture was heated to 80° C. and stirred for 2 hours. After completion of the reaction, water (50 mL) was added to the reaction mixture, and extraction with ethyl acetate (50 mL) was performed. The organic phase was combined, washed with saturated brine (20 mL×2), dried over anhydrous sodium sulfate and filtered; and the solvent was removed from the filtrate under reduced pressure. The resulting residue was purified by column chromatography (eluent: petroleum ether/ethyl acetate=1:1, volume ratio) to obtain intermediate WX014-4. MS-ESI m/z: 258.9 [M+H]$^+$. $^1$H NMR (400 MHz, CDCl$_3$) δ: 8.06 (s, 1H), 7.73 (d, J=0.8 Hz, 1H), 7.72 (s, 1H), 7.45 (s, 1H), 4.22 (q, J=14.4 Hz, 2H), 4.14 (s, 3H), 3.76 (s, 2H), 1.30 (t, J=7.2 Hz, 3H).

Step 5: Synthesis of WX014

Under nitrogen atmosphere, intermediate WX014-4 (0.07 g, 271.03 μmol) was dissolved in N,N-dimethylformamide (10 mL); potassium tert-butoxide (30.41 mg, 271.03 μmol) was added; acrylamide (19.26 mg, 271.03 μmol) was added; and the reaction mixture was stirred at 0° C.-5° C. for 1 hour. After completion of the reaction, water (50 mL) was added to the reaction mixture, and extraction with ethyl acetate (50 mL) was performed. The organic phase was separated, washed with saturated brine (20 mL×2), dried over anhydrous sodium sulfate and filtered; and the solvent was removed from the filtrate under reduced pressure. The resulting residue was subjected to preparative HPLC (mobile phase: acetonitrile/water; acid system: 0.05% HCl) to obtain target compound WX014. $^1$H NMR (400 MHz, DMSO_d$_6$) δ: 10.92 (s, 1H), 8.41 (s, 1H), 7.85 (s, 1H), 7.75 (s, 1H), 7.71 (s, 1H), 4.22 (s, 3H), 4.19 (dd, J=4.6, 12.2 Hz, 1H), 2.68-2.57 (m, 2H), 2.34-2.25 (m, 1H), 2.19-2.09 (m, 1H).

Example 15

Hydrochloride Salt of WX015

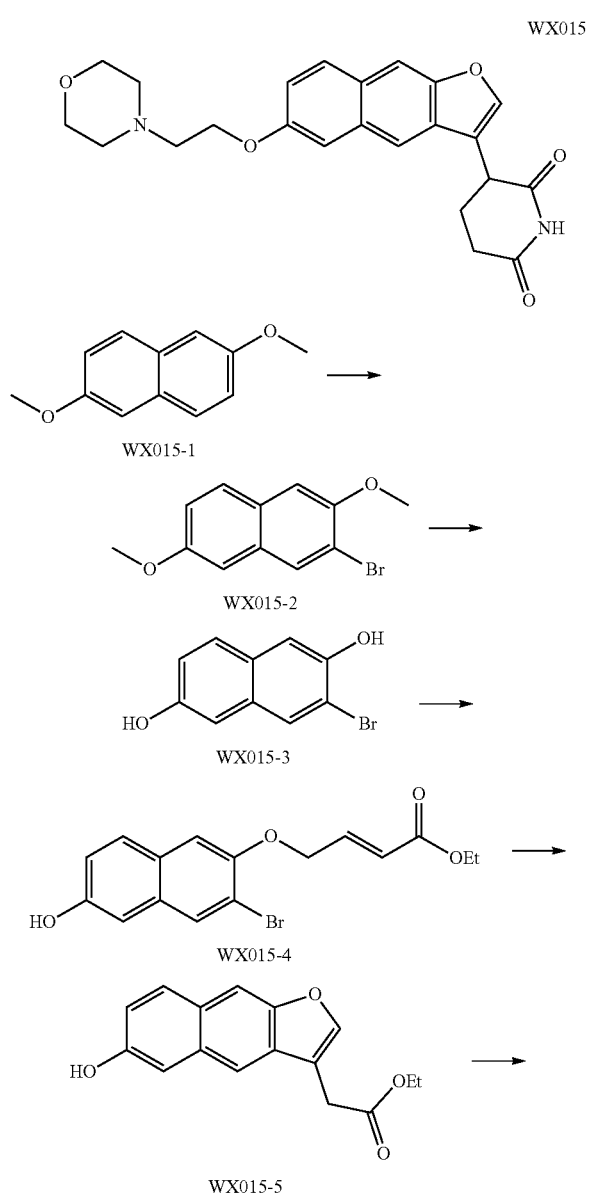

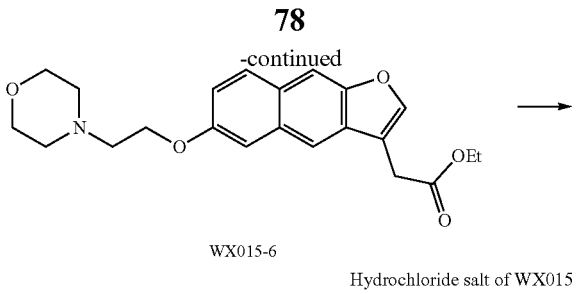

Step 1: Synthesis of Intermediate WX015-2

At room temperature and under nitrogen atmosphere, compound WX015-1 (50 g, 265.64 mmol) was dissolved in tetrahydrofuran (3000 mL); and the reaction mixture was cooled to −65° C.; n-butyllithium (2.5 M, 116.88 mL) was slowly added dropwise to the above-mentioned reaction mixture for about 30 minutes; at −65° C., 1,2-dibromoethane (49.9 g, 265.64 mmol, 20.04 mL) was slowly added dropwise to the above-mentioned solution; and the reaction mixture was stirred and reacted at 20° C. for 12 hours. After completion of the reaction, ethyl acetate (6000 mL) and deionized water (1000 mL) were added to the reaction mixture. The organic phase was separated, washed with saturated brine (1000 mL), dried over anhydrous sodium sulfate and filtered; and the solvent was removed from the filtrate under reduced pressure. The resulting residue was purified by column chromatography (eluent: petroleum ether/ethyl acetate=10:1, volume ratio) to obtain intermediate WX015-2.

Step 2: Synthesis of Intermediate WX015-3

At room temperature and under nitrogen atmosphere, intermediate WX015-2 (50 g, 187.18 mmol) was dissolved in dichloromethane (1000 mL); and the reaction mixture was cooled to −78° C., boron tribromide (187.57 g, 748.73 mmol, 72.14 mL) was slowly added dropwise to the above-mentioned reaction mixture; and the reaction mixture was stirred and reacted at 20° C. for 12 hours. After completion of the reaction, the reaction mixture was cooled to 0° C.-5° C.; methanol (200 mL) was slowly added dropwise to the reaction mixture, which was then stirred at 0° C.-5° C. for 10 minutes; and deionized water (500 mL) was added. The organic phase was separated, washed with saturated brine (500 mL), dried over anhydrous sodium sulfate and filtered; and the solvent was removed from the filtrate under reduced pressure. The resulting residue was purified by column chromatography (eluent: petroleum ether/ethyl acetate=3:1, volume ratio) to obtain intermediate WX015-3. $^1$H NMR (400 MHz, DMSO_d6) δ: 10.18 (s, 1H), 9.57 (s, 1H), 7.93 (s, 1H), 7.57-7.51 (m, 1H), 7.20 (s, 1H), 7.04-6.97 (m, 2H).

Step 3: Synthesis of Intermediate WX015-4

At 0° C.-5° C. and under nitrogen atmosphere, intermediate WX015-3 (25 g, 104.57 mmol), ethyl 4-bromocrotonate (20.19 g, 104.57 mmol, 14.42 mL) and potassium carbonate (28.91 g, 209.15 mmol) were added to N,N-dimethylformamide (500 mL); and the reaction mixture was stirred and reacted at 0° C.-5° C. for 2 hours. After completion of the reaction, water (2000 mL) was added to the reaction mixture, and extraction with ethyl acetate (2000 mL) was performed. The organic phase was separated, washed with saturated brine (500 mL), dried over anhydrous sodium sulfate and filtered; and the solvent was removed from the filtrate under reduced pressure. The resulting residue was purified by column chromatography (eluent:

petroleum ether/ethyl acetate=3:1, volume ratio) to obtain intermediate WX015-4. MS-ESI m/z: 351.0 [M+H]⁺, 353.0 [M+H+2]⁺.

Step 4: Synthesis of Intermediate WX015-5

At room temperature and under nitrogen atmosphere, intermediate WX015-4 (20 g, 50.68 mmol), palladium acetate (3.41 g, 15.21 mmol), tetrabutyl ammonium chloride (14.09 g, 50.68 mmol), sodium formate (10.34 g, 152.05 mmol) and sodium carbonate (16.12 g, 152.05 mmol) were dissolved in N,N-dimethylformamide (500 mL); and the reaction mixture was heated to 80° C. and stirred and reacted for 5 hours. After completion of the reaction, water (200 mL) was added to the reaction mixture, and extraction with ethyl acetate (300 mL) was performed. The organic phase was separated, washed with saturated brine (100 mL), dried over anhydrous sodium sulfate and filtered; and the solvent was removed from the filtrate under reduced pressure. The resulting residue was purified by column chromatography (eluent: petroleum ether/ethyl acetate=3:1, volume ratio) to obtain intermediate WX015-5. MS-ESI m/z: 271.0 [M+H]⁺. ¹H NMR (400 MHz, DMSO_d₆) δ: 9.59 (s, 1H), 7.98 (s, 1H), 7.93 (s, 1H), 7.86 (t, J=3.2 Hz, 2H), 7.21 (d, J=2.0 Hz, 1H), 7.09 (dd, J=2.4, 8.8 Hz, 1H), 4.15 (q, J=7.2 Hz, 2H), 3.85 (s, 2H), 1.22 (t, J=7.2 Hz, 3H).

Step 5: Synthesis of Intermediate WX015-6

At room temperature and under nitrogen atmosphere, intermediate WX015-5 (0.5 g, 1.85 mmol), N-(2-hydroxyethyl)morpholine (363.99 mg, 2.77 mmol, 340.18 μL), triphenylphosphine (727.82 mg, 2.77 mmol) and diisopropyl azodicarboxylate (561.11 mg, 2.77 mmol, 539.53 μL) were dissolved in tetrahydrofuran (20 mL); and the reaction mixture was heated to 70° C. and stirred and reacted for 2 hours. After completion of the reaction, water (20 mL) was added to the reaction mixture, and extraction with ethyl acetate (50 mL) was performed. The organic phase was separated, washed with saturated brine (20 mL), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain intermediate WX015-6. MS-ESI m/z: 384.1 [M+H]⁺.

Step 1: Synthesis of WX015

At room temperature and under nitrogen atmosphere, intermediate WX015-6 (0.15 g, 391.20 μmol) was dissolved in N,N-dimethylformamide (30 mL); potassium tert-butoxide (65.85 mg, 586.80 μmol) was added; acrylamide (27.81 mg, 391.20 μmol) was added; and the reaction mixture was stirred and reacted at 0° C.-5° C. for 2 hours. After completion of the reaction, water (50 mL) was added to the reaction mixture, and extraction with ethyl acetate (100 mL) was performed. The organic phase was separated, washed with saturated brine (20 mL), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain a hydrochloride salt of target compound WX015. MS-ESI m/z: 409.1 [M+H]⁺. ¹H NMR (400 MHz, DMSO_d₆) δ: 11.59 (s, 1H), 10.98 (s, 1H), 8.04 (t, J=4.2 Hz, 3H), 7.96 (d, J=8.8 Hz, 1H), 7.48 (d, J=1.6 Hz, 1H), 7.22 (dd, J=2.2, 9.0 Hz, 1H), 4.66-4.53 (m, 2H), 4.23 (dd, J=4.8, 12.0 Hz, 1H), 4.04-3.81 (m, 4H), 3.67-3.55 (m, 4H), 3.35-3.14 (m, 2H), 2.91-2.75 (m, 1H), 2.69-2.58 (m, 1H), 2.47-2.38 (m, 1H), 2.25-2.11 (m, 1H).

Example 16

Hydrochloride Salt of WX016

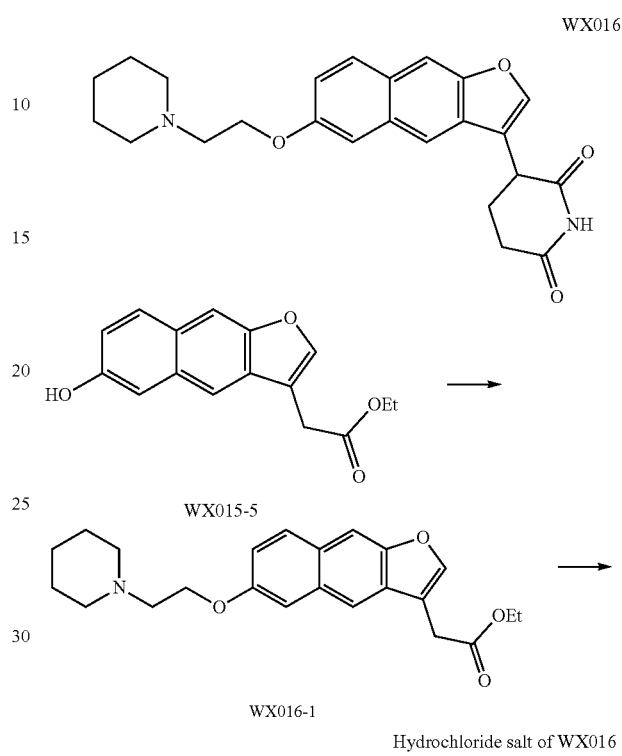

Hydrochloride salt of WX016

Step 1: Synthesis of Intermediate WX016-1

At room temperature and under nitrogen atmosphere, intermediate WX015-5 (0.5 g, 1.85 mmol), 1-(2-hydroxyethyl)piperidine (358.52 mg, 2.77 mmol), triphenylphosphine (727.83 mg, 2.77 mmol) and diisopropyl azodicarboxylate (561.11 mg, 2.77 mmol, 539.53 μL) were dissolved in tetrahydrofuran (20 mL); and the reaction mixture was heated to 70° C. and stirred and reacted for 2 hours. After completion of the reaction, water (20 mL) was added to the reaction mixture, and extraction with ethyl acetate (50 mL) was performed. The organic phase was separated, washed with saturated brine (20 mL), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain intermediate WX016-1. MS-ESI m/z: 382.1 [M+H]⁺.

Step 2: Synthesis of WX016

At room temperature and under nitrogen atmosphere, intermediate WX016-1 (0.15 g, 393.22 μmol) was dissolved in N,N-dimethylformamide (30 mL); potassium tert-butoxide (66.19 mg, 589.83 μmol) was added; acrylamide (27.95 mg, 393.22 μmol) was added; and the reaction mixture was stirred and reacted at 0° C.-5° C. for 2 hours. After completion of the reaction, water (50 mL) was added to the reaction mixture, and extraction with ethyl acetate (100 mL) was performed. The organic phase was separated, washed with saturated brine (20 mL), dried over anhydrous sodium sulfate and filtered; and the solvent was removed from the filtrate under reduced pressure. The resulting residue was purified by preparative HPLC (mobile phase: acetonitrile/ water; acid system: 0.05% HCl) to obtain a hydrochloride salt of target compound WX016. MS-ESI m/z: 407.2 [M+H]+. 1H NMR (400 MHz, DMSO_$d_6$) δ: 10.98 (s, 1H), 10.78 (s, 1H), 8.04 (d, J=3.6 Hz, 2H), 8.02 (s, 1H), 7.96 (d, J=9.2 Hz, 1H), 7.48 (d, J=1.6 Hz, 1H), 7.21 (dd, J=2.2, 9.0 Hz, 1H), 4.61-4.49 (m, 2H), 4.23 (dd, J=4.8, 12.0 Hz, 1H), 3.56-3.51 (m, 4H), 3.11-2.96 (m, 2H), 2.89-2.76 (m, 1H), 2.69-2.58 (m, 1H), 2.47-2.39 (m, 1H), 2.23-2.12 (m, 1H), 1.90-1.78 (m, 4H), 1.75-1.66 (m, 1H), 1.47-1.32 (m, 1H).

Example 17

WX017

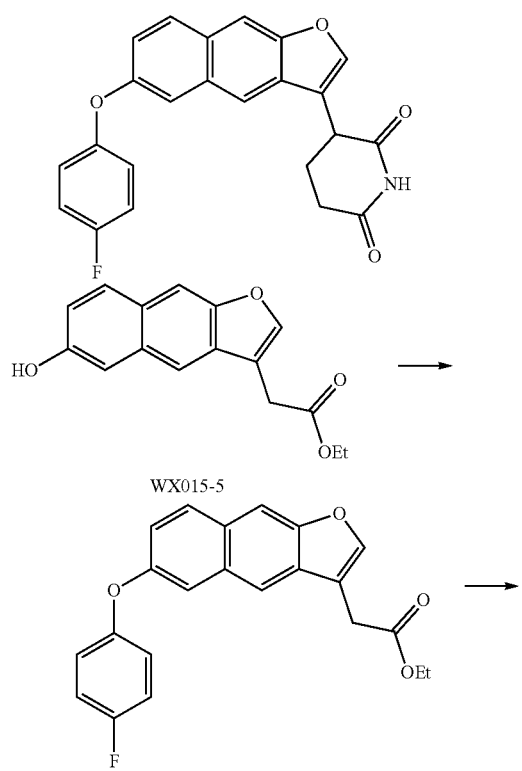

Step 1: Synthesis of Intermediate WX017-1

At room temperature and under nitrogen atmosphere, intermediate WX015-5 (300 mg, 1.11 mmol) was dissolved in dichloromethane (10 mL); copper acetate (201.60 mg, 1.11 mmol), pyridine (175.60 mg, 2.22 mmol, 179.18 μL), triethylamine (224.63 mg, 2.22 mmol, 308.99 μL) and 4-fluorophenylboronic acid (310.61 mg, 2.22 mmol) were added successively; and the reaction mixture was stirred and reacted at room temperature for 14 hours. After completion of the reaction, water (30 mL) was added to the reaction mixture, and extraction with dichloromethane (30 mL×3) was performed. The organic phase was combined, washed with saturated brine (60 mL×2), dried over anhydrous sodium sulfate and filtered; and the solvent was removed from the filtrate under reduced pressure. The resulting residue was purified by column chromatography (eluent: petroleum ether/ethyl acetate=1/0-100/1, volume ratio) to obtain intermediate WX017-1. 1H NMR (400 MHz, CDCl$_3$) δ: 7.92 (d, J=9.2 Hz, 1H), 7.87 (d, J=1.6 Hz, 2H), 7.74 (s, 1H), 7.36 (d, J=2.4 Hz, 1H), 7.25 (dd, J=2.6, 9.0 Hz, 1H), 7.07 (d, J=1.6 Hz, 2H), 7.06 (s, 2H), 4.21 (q, J=7.0 Hz, 2H), 3.76 (d, J=1.2 Hz, 2H), 1.28 (t, J=7.2 Hz, 3H).

Step 2: Synthesis of WX017

At 0° C. and under nitrogen atmosphere, intermediate WX017-1 (180 mg, 494.01 μmol) was added to N,N-dimethylformamide (5 mL), and then potassium tert-butoxide (55.43 mg, 494.01 μmol) and acrylamide (35.11 mg, 494.01 μmol) were added. At 0° C. under nitrogen atmosphere, the reaction mixture was stirred and reacted for additional 1.5 hours. After completion of the reaction, water (30 mL) was added and extraction with ethyl acetate (30 mL×3) was performed. The organic phase was combined, washed with saturated brine (50 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain target compound WX017. MS-ESI m/z: 390.0 [M+H]+. 1H NMR (400 MHz, DMSO_$d_6$) δ: 10.91 (s, 1H), 8.09 (s, 1H), 8.06 (t, J=4.6 Hz, 2H), 8.03 (s, 1H), 7.37 (d, J=2.4 Hz, 1H), 7.32-7.24 (m, 3H), 7.20-7.13 (m, 2H), 4.19 (dd, J=4.6, 12.2 Hz, 1H), 2.82-2.71 (m, 1H), 2.62-2.55 (m, 1H), 2.47-2.40 (m, 1H), 2.16-2.09 (m, 1H).

Example 18

WX018

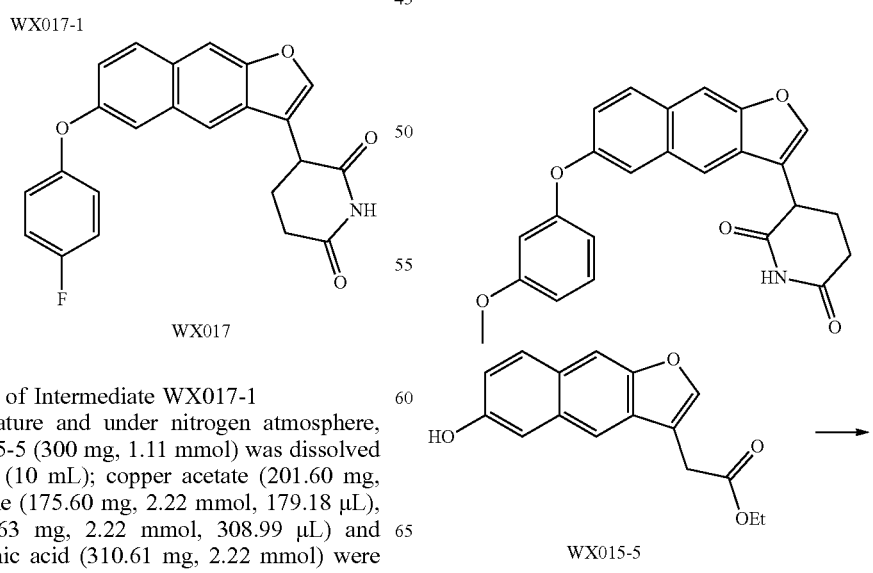

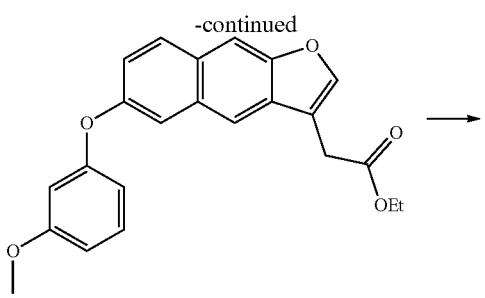

-continued

WX018-1

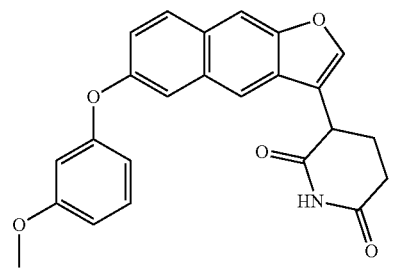

WX018

Step 1: Synthesis of Intermediate WX018-1

At room temperature and under nitrogen atmosphere, intermediate WX015-5 (300 mg, 1.11 mmol) was dissolved in dichloromethane (10 mL); copper acetate (201.60 mg, 1.11 mmol), pyridine (175.60 mg, 2.22 mmol, 179.18 μL), triethylamine (224.63 mg, 2.22 mmol, 308.99 μL) and 3-methoxyphenylboronic acid (337.34 mg, 2.22 mmol) were added successively; and the reaction mixture was stirred and reacted at room temperature for 14 hours. After completion of the reaction, water (30 mL) was added to the reaction mixture, and extraction with dichloromethane (30 mL×3) was performed. The organic phase was combined, washed with saturated brine (60 mL×2), dried over anhydrous sodium sulfate and filtered; and the solvent was removed from the filtrate under reduced pressure. The resulting residue was purified by column chromatography (eluent: petroleum ether/ethyl acetate=1/0-100/1, volume ratio) to obtain intermediate WX018-1. MS-ESI m/z: 377.0 [M+H]$^+$. $^1$H NMR (400 MHz, CDCl$_3$) δ: 7.92 (d, J=9.2 Hz, 1H), 7.89 (d, J=4.0 Hz, 2H), 7.75 (s, 1H), 7.47 (d, J=2.0 Hz, 1H), 7.28 (d, J=2.4 Hz, 1H), 7.24 (dd, J=1.6, 6.4 Hz, 1H), 6.72-6.68 (m, 1H), 6.67-6.63 (m, 2H), 4.22 (q, J=7.0 Hz, 2H), 3.80 (s, 3H), 3.77 (d, J=0.8 Hz, 2H), 1.29 (t, J=7.0 Hz, 3H).

Step 2: Synthesis of WX018

At 0° C. and under nitrogen atmosphere, intermediate WX018-1 (250 mg, 612.11 μmol, purity: 92.16%) was added to N,N-dimethylformamide (5 mL), and then potassium tert-butoxide (68.69 mg, 612.11 μmol) and acrylamide (43.51 mg, 612.11 μmol) were added. At 0° C. under nitrogen atmosphere, the reaction mixture was stirred and reacted for additional 2 hours. After completion of the reaction, water (30 mL) was added and extraction with ethyl acetate (30 mL×3) was performed. The organic phase was combined, washed with saturated brine (50 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain target compound WX018. MS-ESI m/z: 402.0 [M+H]$^+$. $^1$H NMR (400 MHz, DMSO-d$_6$) δ: 10.93 (s, 1H), 8.11-8.07 (m, 2H), 8.06-8.02 (m, 2H), 7.46 (d, J=2.4 Hz, 1H), 7.34-7.26 (m, 2H), 6.75 (dd, J=2.4, 8.0 Hz, 1H), 6.67 (t, J=2.4 Hz, 1H), 6.62 (dd, J=2.0, 8.0 Hz, 1H), 4.20 (dd, J=4.8, 12.4 Hz, 1H), 3.74 (s, 3H), 2.83-2.72 (m, 1H), 2.67-2.56 (m, 1H), 2.45-2.31 (m, 1H), 2.17-2.09 (m, 1H).

Example 19

WX019

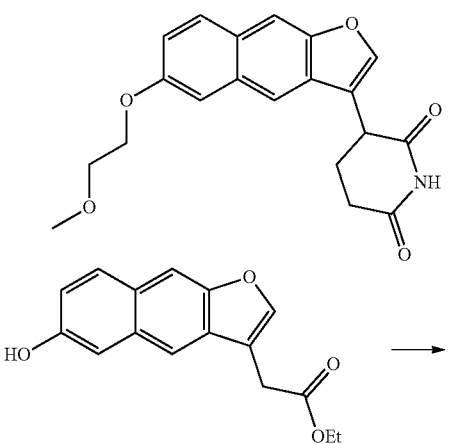

WX015-5

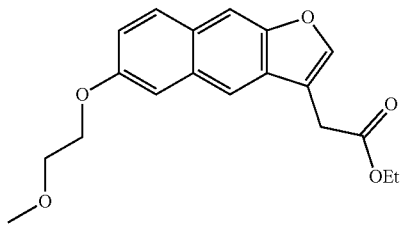

WX019-1

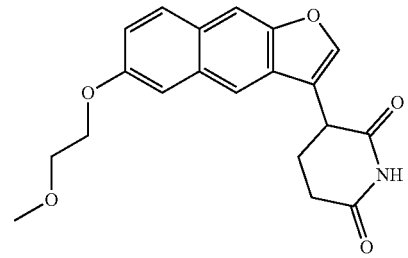

WX019

Step 1: Synthesis of Intermediate WX019-1

At room temperature and under nitrogen atmosphere, intermediate WX015-5 (400 mg, 1.48 mmol) and 2-bromoethyl methyl ether (205.70 mg, 1.48 mmol) were dissolved in N, N-dimethylformamide (50 mL), and then potassium carbonate (613.63 mg, 4.44 mmol) and potassium iodide (1.23 g, 7.40 mmol) were added; and the reaction mixture was warmed to 50° C. and stirred and reacted for 36 hours. After completion of the reaction, the reaction mixture was cooled to room temperature; water (50 mL) was added, and extraction with ethyl acetate (20 mL×3) was performed. The organic phase was combined, washed with saturated brine (100 mL×2), dried over anhydrous sodium sulfate and filtered; and the solvent was removed from the filtrate under reduced pressure. The resulting residue was purified by a silica gel plate (eluent: petroleum ether/ethyl acetate=5/1, volume ratio) to obtain intermediate WX019-1. MS-ESI m/z: 328.9 [M+H]⁺. ¹H NMR (400 MHz, CDCl₃) δ: 7.89 (s, 1H), 7.82 (t, J=4.6 Hz, 2H), 7.72 (s, 1H), 7.25 (d, J=2.4 Hz, 1H), 7.21 (dd, J=2.6, 9.0 Hz, 1H), 4.27 (t, J=4.8 Hz, 2H), 4.22 (q, J=7.6 Hz, 2H), 3.85 (t, J=4.6 Hz, 2H), 3.77 (d, J=0.8 Hz, 2H), 3.50 (s, 3H), 1.29 (t, J=7.0 Hz, 3H).

Step 2: Synthesis of WX019

At 0° C. and under nitrogen atmosphere, intermediate WX019-1 (360 mg, 1.01 mmol, purity: 92.40%) was dissolved in N,N-dimethylformamide (30 mL), and then potassium tert-butoxide (113.67 mg, 1.01 mmol) and acrylamide (72.00 mg, 1.01 mmol) were added; and the reaction mixture was stirred and reacted at 0° C. for additional 2 hours. After completion of the reaction, water (50 mL) was added for dilution, and extraction with ethyl acetate (20 mL×3) was performed. The organic phase was combined, washed with saturated brine (40 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain target compound WX019. MS-ESI m/z: 354.1 [M+H]⁺. ¹H NMR (400 MHz, DMSO_d₆) δ: 10.96 (s, 1H), 8.01 (s, 2H), 7.99 (s, 1H), 7.91 (d, J=9.2 Hz, 1H), 7.39 (d, J=2.0 Hz, 1H), 7.15 (dd, J=2.2, 9.0 Hz, 1H), 4.22 (dd, J=4.8, 12.4 Hz, 1H), 4.20-4.18 (m, 2H), 3.73 (t, J=4.4 Hz, 2H), 3.30 (s, 3H), 2.86-2.74 (m, 1H), 2.69-2.59 (m, 1H), 2.45-2.33 (m, 1H), 2.20-2.11 (m, 1H).

Example 20

WX020

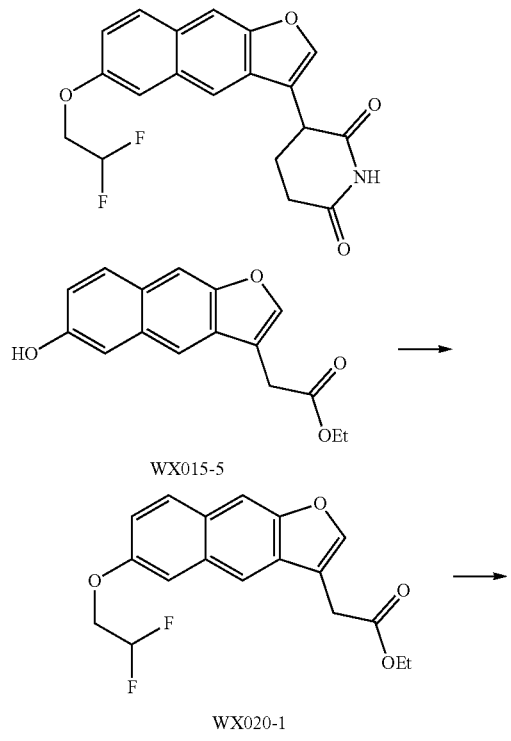

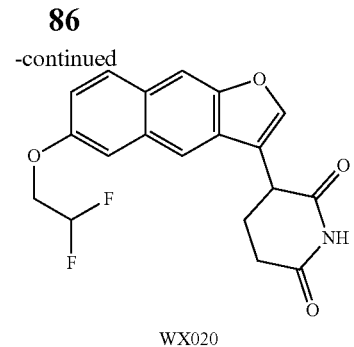

Step 1: Synthesis of Intermediate WX020-1

At room temperature and under nitrogen atmosphere, intermediate WX015-5 (300 mg, 1.11 mmol) and 2,2-difluoroethyl trifluoromethanesulfonate (237.66 mg, 1.11 mmol) were dissolved in N,N-dimethylformamide (30 mL), and then potassium carbonate (460.22 mg, 3.33 mmol) was added; and the reaction mixture was stirred and reacted at room temperature for additional 36 hours. After completion of the reaction, water (50 mL) was added, and extraction with ethyl acetate (20 mL×3) was performed. The organic phase was combined, washed with saturated brine (100 mL×2), dried over anhydrous sodium sulfate and filtered; and the solvent was removed from the filtrate under reduced pressure. The resulting residue was purified by column chromatography (eluent: petroleum ether/ethyl acetate=1/0-10/1, volume ratio) to obtain intermediate WX020-1. MS-ESI m/z: 334.9 [M+H]⁺. ¹H NMR (400 MHz, CDCl₃) δ: 7.92 (s, 1H), 7.88-7.83 (m, 2H), 7.74 (s, 1H), 7.24 (d, J=2.4 Hz, 1H), 7.19 (dd, J=2.6, 9.0 Hz, 1H), 6.35-6.03 (m, 1H), 4.33 (td, J=4.2, 13.0 Hz, 2H), 4.23 (q, J=7.0 Hz, 2H), 3.78 (s, 2H), 1.30 (t, J=7.2 Hz, 3H).

Step 2: Synthesis of WX020

At 0° C. and under nitrogen atmosphere, intermediate WX020-1 (101 mg, 299.36 μmol, purity: 99.09%) was dissolved in N,N-dimethylformamide (30 mL), and then potassium tert-butoxide (33.59 mg, 299.36 μmol) and acrylamide (21.28 mg, 299.36 μmol) were added; and the reaction mixture was stirred and reacted at 0° C. for additional 2 hours. After completion of the reaction, water (50 mL) was added for dilution, and extraction with ethyl acetate (50 mL×3) was performed. The organic phase was combined, washed with saturated brine (100 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain target compound WX020. MS-ESI m/z: 360.0. [M+H]⁺. ¹H NMR (400 MHz, DMSO_d₆) δ: 10.98 (s, 1H), 8.04 (d, J=5.6 Hz, 2H), 8.01 (s, 1H), 7.95 (d, J=9.2 Hz, 1H), 7.50 (d, J=2.4 Hz, 1H), 7.21 (dd, J=2.6, 9.0 Hz, 1H), 6.66-6.28 (m, 1H), 4.49-4.37 (m, 2H), 4.23 (dd, J=5.0, 12.2 Hz, 1H), 2.85-2.76 (m, 1H), 2.69-2.64 (m, 1H), 2.43-2.33 (m, 1H), 2.21-2.13 (m, 1H).

Example 21

WX021

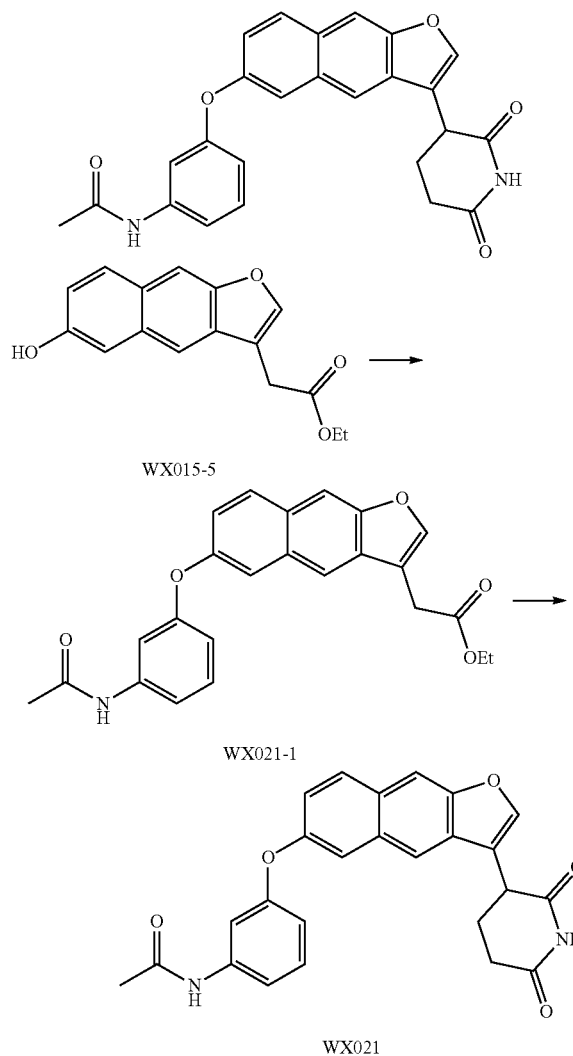

Step 1: Synthesis of Intermediate WX021-1

At 20° C. and under nitrogen atmosphere, intermediate WX015-5 (300 mg, 1.11 mmol) and 3-acetamidophenylboronic acid (397.32 mg, 2.22 mmol) were dissolved in N,N-dimethylformamide (50 mL), and then copper acetate (201.60 mg, 1.11 mmol), triethylamine (224.63 mg, 2.22 mmol) and pyridine (175.60 mg, 2.22 mmol) were added; and the reaction mixture was warmed to 50° C. and stirred and reacted for additional 14 hours. After completion of the reaction, the reaction mixture was cooled to room temperature; water (50 mL) was added; and extraction with ethyl acetate (20 mL×3) was performed. The organic phase was combined, washed with saturated brine (100 mL×2), dried over anhydrous sodium sulfate and filtered; and the solvent was removed from the filtrate under reduced pressure. The resulting residue was purified by a plate (eluent: petroleum ether/ethyl acetate=2/1, volume ratio) to obtain intermediate WX021-1. MS-ESI m/z: 403.9 [M+H]$^+$. $^1$H NMR (400 MHz, CDCl$_3$) δ: 7.92 (d, J=8.8 Hz, 1H), 7.88 (d, J=4.0 Hz, 2H), 7.74 (s, 1H), 7.49 (d, J=7.6 Hz, 1H), 7.46 (d, J=2.4 Hz, 1H), 7.36-7.29 (m, 3H), 7.22-7.17 (m, 2H), 4.21 (q, J=7.2 Hz, 2H), 3.76 (d, J=1.2 Hz, 2H), 2.15 (s, 3H), 1.29 (t, J=7.4 Hz, 3H).

Step 2: Synthesis of WX021

At 0° C. and under nitrogen atmosphere, intermediate WX021-1 (115 mg, 222.80 µmol, purity: 78.16%) was dissolved in N,N-dimethylformamide (30 mL), and then potassium tert-butoxide (25.00 mg, 222.80 µmol) and acrylamide (15.84 mg, 222.80 µmol) were added; and the reaction mixture was stirred and reacted at 0° C. for additional 2 hours. After completion of the reaction, water (50 mL) was added for dilution, and extraction with ethyl acetate (50 mL×3) was performed. The organic phase was combined, washed with saturated brine (100 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain target compound WX021. MS-ESI m/z: 429.1. [M+H]$^+$. $^1$H NMR (400 MHz, DMSO_d$_6$) δ: 10.93 (s, 1H), 10.01 (s, 1H), 8.11 (s, 1H), 8.09-8.02 (m, 3H), 7.47 (d, J=2.4 Hz, 1H), 7.37 (d, J=8.0 Hz, 1H), 7.32 (d, J=8.0 Hz, 2H), 7.28 (dd, J=2.6, 9.0 Hz, 1H), 6.77 (dd, J=1.6, 8.0 Hz, 1H), 4.20 (dd, J=4.8, 12.0 Hz, 1H), 2.82-2.73 (m, 1H), 2.63-2.56 (m, 1H), 2.47-2.41 (m, 1H), 2.17-2.10 (m, 1H), 1.99 (s, 3H).

Example 22

Hydrochloride Salt of WX022

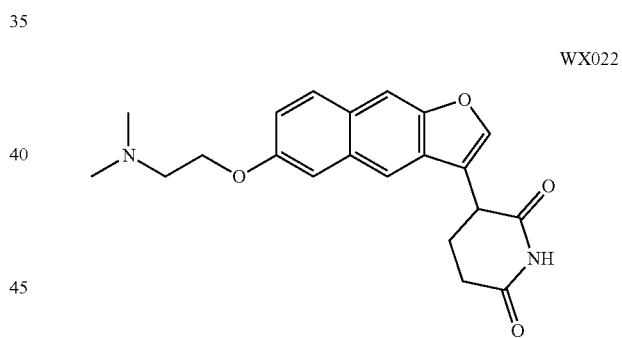

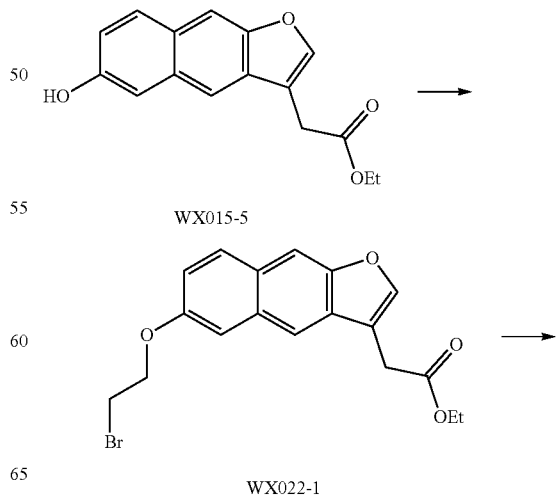

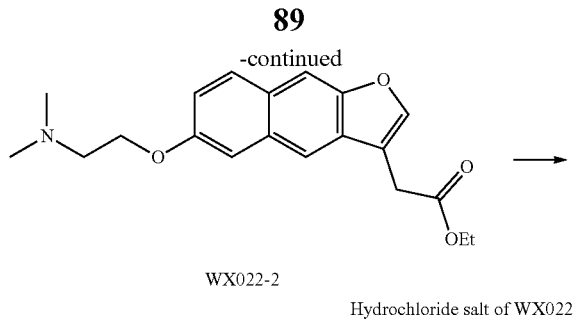

WX022-2

Hydrochloride salt of WX022

Step 1: Synthesis of Intermediate WX022-1

At room temperature and under nitrogen atmosphere, intermediate WX015-5 (0.5 g, 1.68 mmol, purity: 91%) was dissolved in toluene (50 mL), and then 1,2-dibromoethane (948.76 mg, 5.05 mmol, 381.03 μL), potassium carbonate (698.01 mg, 5.05 mmol) and 18-Crown-6 (4.45 g, 16.83 mmol) were added; and the reaction mixture was heated to 110° C. and stirred and reacted for 12 hours. After completion of the reaction, two batches were combined for treatment. The reaction mixture was cooled to room temperature, diluted by pouring into water (50 mL) and extracted with ethyl acetate (30 mL×3). The organic phase was combined, washed with water (50 mL×2) and saturated brine (50 mL), dried over anhydrous sodium sulfate and filtered; and the solvent was removed from the filtrate under reduced pressure. The resulting residue was purified by column chromatography (eluent: petroleum ether/ethyl acetate=20/1 to 5/1, volume ratio) to obtain intermediate WX022-1. MS-ESI m/z: 376.8 [M+H]$^+$, 378.8 [M+H+2]$^+$. $^1$H NMR (400 MHz, CDCl$_3$) δ: 7.90 (s, 1H), 7.87-7.83 (m, 2H), 7.73 (s, 1H), 7.25 (d, J=2.4 Hz, 1H), 7.19 (dd, J=2.6, 9.0 Hz, 1H), 4.44 (t, J=6.4 Hz, 2H), 4.22 (q, J=7.0 Hz, 2H), 3.78 (s, 2H), 3.74 (t, J=6.4 Hz, 2H), 1.30 (t, J=7.2 Hz, 3H).

Step 2: Synthesis of Intermediate WX022-2

At room temperature and under nitrogen atmosphere, intermediate WX022-1 (0.25 g, 662.73 μmol) was dissolved in acetonitrile (25 mL), and then dimethanamine aqueous solution (283.84 mg, 2.52 mmol, purity: 40%) and potassium carbonate (183.19 mg, 1.33 mmol) were added; and the reaction mixture was heated to 80° C. and stirred and reacted for 12 hours. After completion of the reaction, the reaction mixture was cooled to room temperature, and the solvent was removed under reduced pressure. The residue was diluted by adding water (30 mL) and extracted with ethyl acetate (30 mL×3). The organic phase was combined, washed with saturated brine (30 mL×2), dried over anhydrous sodium sulfate and filtered; and the solvent was removed from the filtrate under reduced pressure. The resulting residue was purified by a silica gel plate (developing agent: dichloromethane/methanol=30/1, volume ratio) to obtain target intermediate WX022-2. MS-ESI m/z: 341.9 [M+H]$^+$. $^1$H NMR (400 MHz, CDCl$_3$) δ: 7.89 (s, 1H), 7.84-7.79 (m, 2H), 7.72 (s, 1H), 7.25 (d, J=2.0 Hz, 1H), 7.19 (dd, J=2.6, 9.0 Hz, 1H), 4.26-4.18 (m, 4H), 3.77 (d, J=0.8 Hz, 2H), 2.83 (t, J=5.6 Hz, 2H), 2.39 (s, 6H), 1.29 (t, J=7.0 Hz, 3H).

Step 3: Synthesis of WX022

At 0° C. and under nitrogen atmosphere, intermediate WX022-2 (0.15 g, 421.49 μmol) was dissolved in N,N-dimethylformamide (5 mL); potassium tert-butoxide (52.02 mg, 463.63 μmol) was added, and then acrylamide (29.96 mg, 421.49 μmol) was added; and the reaction mixture was stirred and reacted at 0° C. for 1 hour. After completion of the reaction, water (30 mL) was added for dilution, and extraction with ethyl acetate (20 mL×3) was performed. The organic phase was combined, washed with saturated brine (30 mL×3), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain a hydrochloride salt of target compound WX022. MS-ESI m/z: 367.2 [M+H]$^+$. $^1$H NMR (400 MHz, DMSO_d$_6$) δ: 10.98 (s, 1H), 10.36 (s, 1H), 8.05 (s, 1H), 8.04 (s, 1H), 8.01 (s, 1H), 7.96 (d, J=9.2 Hz, 1H), 7.48 (d, J=2.0 Hz, 1H), 7.21 (dd, J=2.6, 9.0 Hz, 1H), 4.47 (t, J=4.8 Hz, 2H), 4.23 (dd, J=4.8, 12.4 Hz, 1H), 3.62-3.55 (m, 2H), 2.87 (s, 6H), 2.84-2.75 (m, 1H), 2.66-2.59 (m, 1H), 2.47-2.38 (m, 1H), 2.22-2.13 (m, 1H).

Example 23

Hydrochloride Salt of WX023

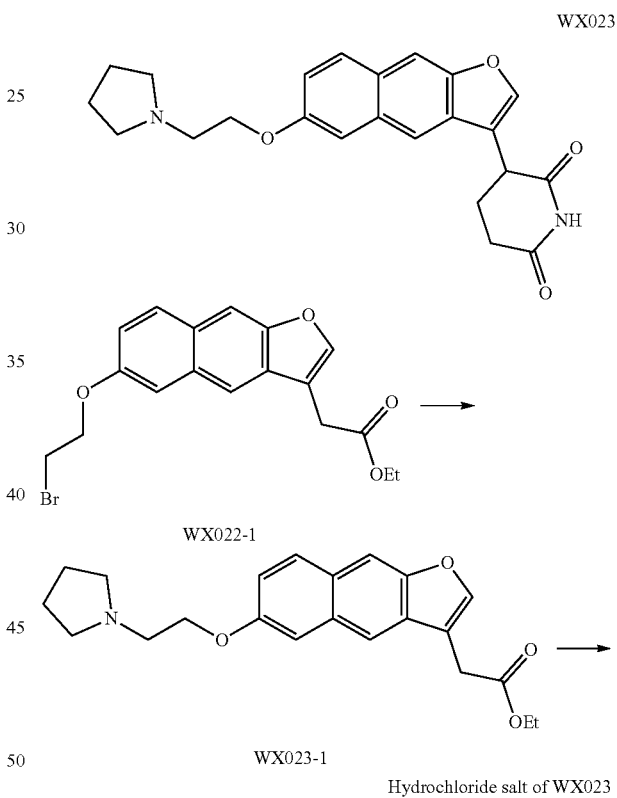

Step 1: Synthesis of Intermediate WX023-1

At room temperature and under nitrogen atmosphere, intermediate WX022-1 (0.3 g, 795.28 μmol) was dissolved in acetonitrile (25 mL), and then pyrrolidine (216.81 mg, 3.05 mmol) and potassium carbonate (219.83 mg, 1.60 mmol) were added; and the reaction mixture was heated to 80° C. and stirred and reacted for 12 hours. After completion of the reaction, the reaction mixture was cooled to room temperature, and the solvent was removed under reduced pressure. The residue was diluted by adding water (30 mL) and extracted with ethyl acetate (30 mL×3). The organic phase was combined, washed with saturated brine (30 mL×2), dried over anhydrous sodium sulfate and filtered; and the solvent was removed from the filtrate under reduced pressure. The resulting residue was purified by a silica gel plate (developing agent: dichloromethane/methanol=30/1, volume ratio) to obtain intermediate WX023-1. MS-ESI m/z: 368.1 [M+H]+. 1H NMR (400 MHz, CDCl3) δ: 7.89 (s, 1H), 7.84-7.79 (m, 2H), 7.72 (s, 1H) 7.25 (d, J=2.4 Hz, 1H), 7.19 (dd, J=2.2, 9.0 Hz, 1H), 4.28-4.19 (m, 4H), 3.77 (d, J=0.8 Hz, 2H), 3.00 (t, J=5.8 Hz, 2H), 2.73-2.65 (m, 4H), 1.88-1.81 (m, 4H), 1.29 (t, J=7.0 Hz, 3H).

Step 2: Synthesis of WX023

At 0° C. and under nitrogen atmosphere, intermediate WX023-1 (0.25 g, 670.73 umol) was dissolved in N,N-dimethylformamide (5 mL); potassium tert-butoxide (82.79 mg, 737.80 μmol) was added, and then acrylamide (47.67 mg, 670.73 μmol) was added; and the reaction mixture was stirred and reacted at 0° C. for 1 hour. After completion of the reaction, water (30 mL) was added for dilution, and extraction with ethyl acetate (20 mL×3) was performed. The organic phase was combined, washed with saturated brine (30 mL×3), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain a hydrochloride salt of target compound WX023. MS-ESI m/z: 393.2 [M+H]+. 1H NMR (400 MHz, DMSO_d6) δ: 10.97 (s, 1H), 10.86 (s, 1H), 8.04 (s, 1H), 8.03 (s, 1H), 8.01 (s, 1H), 7.96 (d, J=9.2 Hz, 1H), 7.47 (d, J=2.0 Hz, 1H), 7.22 (dd, J=2.2, 9.0 Hz, 1H), 4.47 (t, J=4.4 Hz, 2H), 4.23 (dd, J=4.8, 12.4 Hz, 1H), 3.69-3.56 (m, 4H), 3.20-3.07 (m, 2H), 2.87-2.75 (m, 1H), 2.69-2.57 (m, 1H), 2.46-2.38 (m, 1H), 2.22-2.11 (m, 1H), 2.08-1.96 (m, 2H), 1.95-1.84 (m, 2H).

Example 24

Trifluoroacetate Salt of WX024

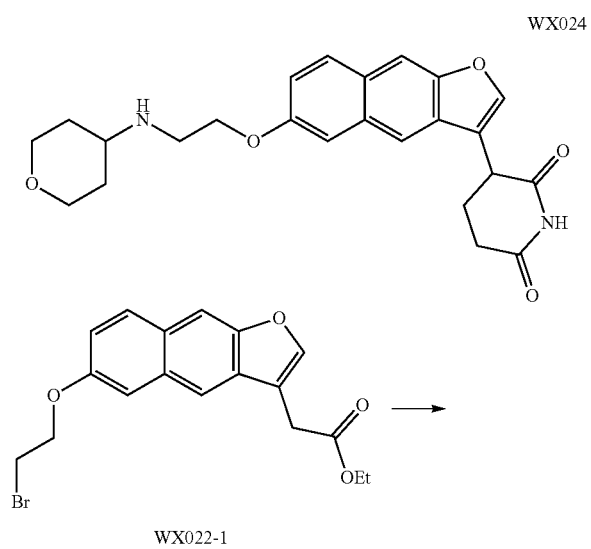

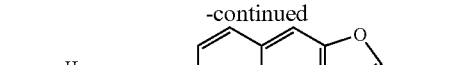

Step 1: Synthesis of Intermediate WX024-1

At room temperature and under nitrogen atmosphere, intermediate WX022-1 (0.15 g, 385.35 μmol, purity: 96.91%) was dissolved in acetonitrile (25 mL), and then 4-amino tetrahydropyran (155.91 mg, 1.54 mmol, 455.11 μL) and potassium carbonate (106.52 mg, 770.70 μmol) were added; and the reaction mixture was heated to 80° C. and stirred and reacted for 12 hours. After completion of the reaction, the reaction mixture was cooled to room temperature, and the solvent was removed by concentration under reduced pressure. The residue was diluted by adding water (30 mL) and extracted with ethyl acetate (20 mL×3). The organic phase was combined, washed with water (30 mL×3), dried over anhydrous sodium sulfate and filtered; and the solvent was removed from the filtrate under reduced pressure. The resulting residue was purified by a silica gel plate (developing agent: dichloromethane/methanol=30/1, volume ratio) to obtain intermediate WX024-1. MS-ESI m/z: 384.4 [M+H]+. 1H NMR (400 MHz, CDCl3) δ: 7.88 (s, 1H), 7.82 (t, J=4.6 Hz, 2H), 7.72 (s, 1H), 7.26 (d, J=2.4 Hz, 1H), 7.16 (dd, J=2.4, 9.2 Hz, 1H), 4.23 (t, J=5.2 Hz, 2H), 4.06-3.98 (m, 2H), 3.80 (s, 2H), 3.76 (s, 3H), 3.44 (td, J=1.6, 11.6 Hz, 2H), 3.13 (t, J=5.2 Hz, 2H), 2.85-2.77 (m, 1H), 1.93-1.88 (m, 2H), 1.55-1.44 (m, 2H).

Step 2: Synthesis of WX024

At 0° C. and under nitrogen atmosphere, intermediate WX024-1 (0.12 g, 308.52 μmol, purity: 98.58%) was dissolved in N,N-dimethylformamide (5 mL); potassium tert-butoxide (38.08 mg, 339.37 μmol) was added, and then acrylamide (21.93 mg, 308.52 μmol) was added; and the reaction mixture was stirred and reacted at 0° C. for 1 hour. After completion of the reaction, water (30 mL) was added for dilution, and extraction with ethyl acetate (20 mL×3) was performed. The organic phase was combined, washed with saturated brine (30 mL×3), dried over anhydrous sodium sulfate and filtered; and the solvent was removed from the filtrate under reduced pressure. The resulting residue was purified by preparative HPLC (mobile phase: acetonitrile/water; acid system: 0.05% TFA) to obtain a trifluoroacetate salt of target compound WX024. MS-ESI m/z: 423.1 [M+H]+. 1H NMR (400 MHz, DMSO_d6) δ: 10.97 (s, 1H), 8.85 (s, 2H), 8.05 (s, 1H), 8.03 (s, 1H), 8.02 (s, 1H), 7.97 (d, J=9.2 Hz, 1H), 7.47 (d, J=2.0 Hz, 1H), 7.22 (dd, J=2.4, 9.2 Hz, 1H), 4.36 (t, J=4.4 Hz, 2H), 4.22 (dd, J=4.8, 12.4 Hz, 1H), 3.94 (dd, J=3.4, 11.4 Hz, 2H), 3.48-3.46 (m, 2H), 3.33-3.28 (m, 2H), 2.85-2.75 (m, 1H), 2.66-2.60 (m, 1H), 2.45-2.32 (m, 1H), 2.24-2.12 (m, 1H), 2.05-1.95 (m, 2H), 1.68-1.55 (m, 2H), 1.25-1.21 (m, 1H).

Example 25

Hydrochloride Salt of WX025

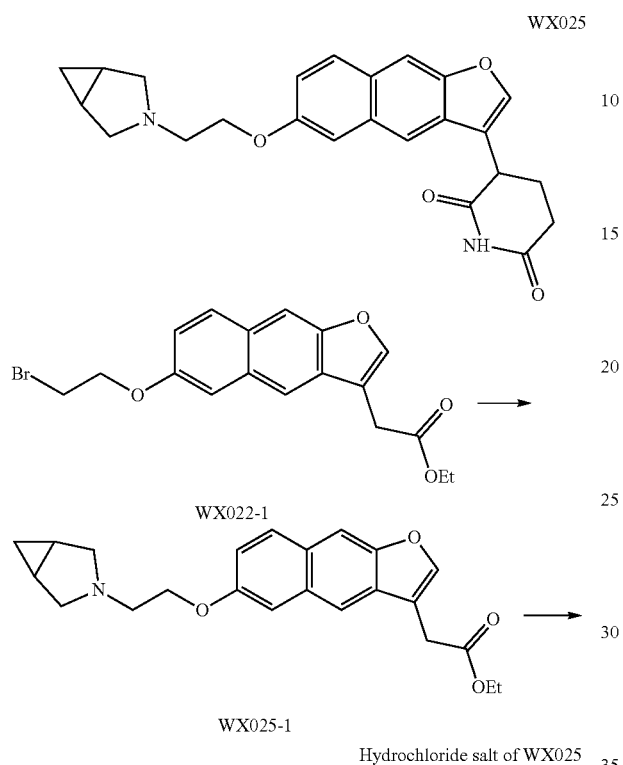

Step 1: Synthesis of Intermediate WX025-1

At room temperature and under nitrogen atmosphere, intermediate WX022-1 (145 mg, 382.04 μmol, purity: 99.39%) was dissolved in acetonitrile (10 mL); 3-azabicyclo [3.1.0]hexane (31.76 mg, 382.04 μmol) and potassium carbonate (105.60 mg, 764.08 μmol) were added; and the reaction mixture was warmed to 80° C. and stirred and reacted at 80° C. for 14 hours. After completion of the reaction, water (30 mL) was added to the reaction mixture, and extraction with ethyl acetate (30 mL×3) was performed. The organic phase was combined, washed with saturated brine (50 mL×2), dried over anhydrous sodium sulfate and filtered; and the solvent was removed from the filtrate under reduced pressure. The resulting residue was purified by a plate (developing agent: petroleum ether/ethyl acetate=1:1, volume ratio) to obtain intermediate WX025-1. MS-ESI m/z: 379.9 [M+H]$^+$.

Step 2: Synthesis of WX025

At 0° C. and under nitrogen atmosphere, intermediate WX025-1 (124 mg, 316.99 μmol, purity: 97.00%) was dissolved in N,N-dimethylformamide (5 mL), and then potassium tert-butoxide (35.57 mg, 316.99 μmol) and acrylamide (22.53 mg, 316.99 μmol) were added. At 0° C. under nitrogen atmosphere, the reaction mixture was stirred and reacted for additional 1.5 hours. After completion of the reaction, water (30 mL) was added and extraction with ethyl acetate (30 mL×3) was performed. The organic phase was combined, washed with saturated brine (50 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain a hydrochloride salt of target compound WX025. MS-ESI m/z: 405.2 [M+H]$^+$. $^1$H NMR (400 MHz, DMSO_d$_6$) δ: 10.97 (s, 1H), 10.50 (s, 1H), 8.03 (d, J=3.6 Hz, 2H), 8.01 (s, 1H), 7.95 (d, J=9.2 Hz, 1H), 7.45 (s, 1H), 7.20 (d, J=9.2 Hz, 1H), 4.53-4.34 (m, 2H), 4.22 (dd, J=5.0, 12.2 Hz, 1H), 3.71-3.53 (m, 2H), 3.52-3.36 (m, 4H), 2.86-2.75 (m, 1H), 2.68-2.59 (m, 1H), 2.47-2.31 (m, 1H), 2.21-2.12 (m, 1H), 1.81-1.60 (m, 2H), 1.06-0.85 (m, 1H), 0.72-0.54 (m, 1H).

Example 26

Hydrochloride Salt of WX026

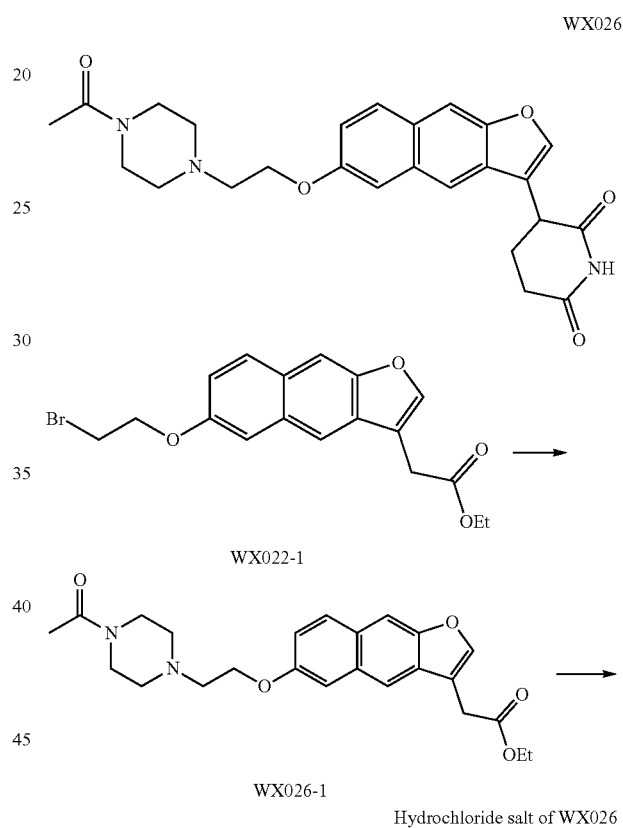

Step 1: Synthesis of Intermediate WX026-1

At room temperature and under nitrogen atmosphere, intermediate WX022-1 (150 mg, 394.58 μmol, purity: 99.23%) was dissolved in acetonitrile (10 mL); 1-acetylpiperazin (50.57 mg, 394.58 μmol) and potassium carbonate (109.07 mg, 789.15 μmol) were added; and the reaction mixture was warmed to 80° C. and stirred and reacted at 80° C. for 14 hours. After completion of the reaction, the reaction mixture was cooled to room temperature, added water (30 mL) and extracted with ethyl acetate (30 mL×3). The organic phase was combined, washed with saturated brine (50 mL×2), dried over anhydrous sodium sulfate and filtered; and the solvent was removed from the filtrate under reduced pressure. The resulting residue was purified by a silica gel plate (developing agent: petroleum ether/ethyl acetate=0:1, volume ratio) to obtain intermediate WX026-1. MS-ESI m/z: 425.4 [M+H]$^+$.

Step 2: Synthesis of WX026

At 0° C. and under nitrogen atmosphere, intermediate WX026-1 (80 mg, 183.92 µmol, purity: 97.59%) was added to N,N-dimethylformamide (5 mL), and then potassium tert-butoxide (20.64 mg, 183.92 µmol) and acrylamide (13.07 mg, 183.92 µmol) were added. At 0° C. and under nitrogen atmosphere, the reaction mixture was stirred and reacted for additional 1.5 hours. After completion of the reaction, water (30 mL) was added and extraction with ethyl acetate (30 mL×3) was performed. The organic phase was combined, washed with saturated brine (50 mL×2), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain a hydrochloride salt of target compound WX026. MS-ESI m/z: 450.2 [M+H]$^+$. $^1$H NMR (400 MHz, DMSO_$d_6$) δ: 10.97 (s, 1H), 10.90 (s, 1H), 8.04 (d, J=5.2 Hz, 2H), 8.01 (s, 1H), 7.97 (d, J=9.2 Hz, 1H), 7.48 (d, J=2.0 Hz, 1H), 7.22 (dd, J=2.4, 9.2 Hz, 1H), 4.56-4.50 (m, 2H), 4.48-4.41 (m, 1H), 4.23 (dd, J=5.2, 12.0 Hz, 1H), 4.08-3.98 (m, 1H), 3.68-3.57 (m, 4H), 3.56-3.49 (m, 1H), 3.27-3.16 (m, 1H), 3.14-3.02 (m, 2H), 2.87-2.76 (m, 1H), 2.69-2.59 (m, 1H), 2.47-2.35 (m, 1H), 2.21-2.13 (m, 1H), 2.05 (s, 3H).

Example 27

Trifluoroacetate Salt of WX027

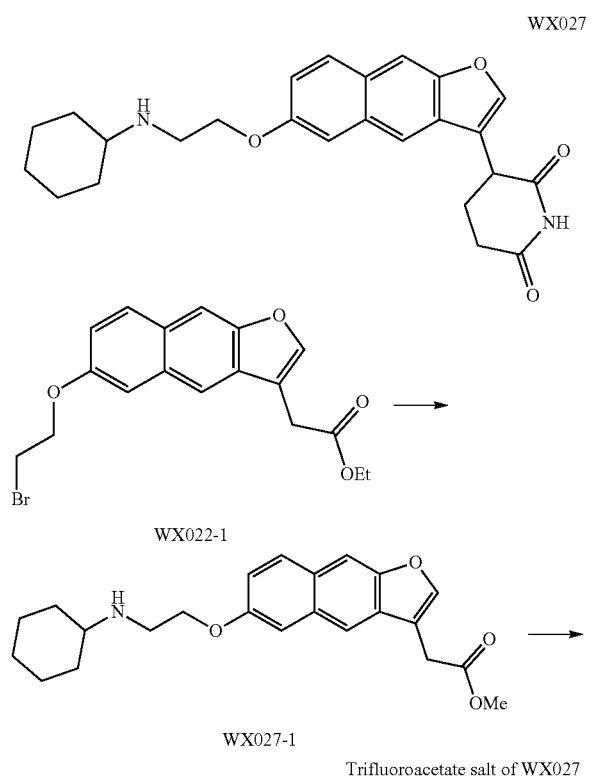

Step 1: Synthesis of Intermediate WX027-1

At room temperature and under nitrogen atmosphere, intermediate WX022-1 (0.15 g, 385.35 µmol, purity: 96.91%) was dissolved in acetonitrile (25 mL), and then cyclohexane (152.87 mg, 1.54 mmol) and potassium carbonate (106.52 mg, 770.70 µmol) were added; and the reaction mixture was heated to 80° C. and stirred and reacted for 12 hours. After completion of the reaction, the reaction mixture was cooled to room temperature, and the solvent was removed under reduced pressure. The residue was diluted by adding water (30 mL) and extracted with ethyl acetate (20 mL×3). The organic phase was combined, washed with water (30 mL×3), dried over anhydrous sodium sulfate and filtered; and the solvent was removed from the filtrate under reduced pressure. The resulting residue was purified by a silica gel plate (developing agent: dichloromethane/methanol=30/1, volume ratio) to obtain intermediate WX027-1. MS-ESI m/z: 382.4 [M+H]$^+$. $^1$H NMR (400 MHz, CDCl$_3$) δ: 7.87 (s, 1H), 7.83-7.79 (m, 2H), 7.72 (s, 1H), 7.25 (d, J=2.4 Hz, 1H), 7.16 (dd, J=2.4, 9.2 Hz, 1H), 4.22 (t, J=5.2 Hz, 2H), 3.79 (s, 2H), 3.76 (s, 3H), 3.12 (t, J=5.2 Hz, 2H), 2.60-2.52 (m, 1H), 2.01-1.93 (m, 2H), 1.77-1.73 (m, 1H), 1.69-1.60 (m, 1H), 1.36-1.10 (m, 6H).

Step 2: Synthesis of WX027

At 0° C. and under nitrogen atmosphere, intermediate WX027-1 (72.04 mg, 183.50 µmol, purity: 97.17%) was dissolved in N,N-dimethylformamide (5 mL); potassium tert-butoxide (22.65 mg, 201.85 µmol) was added, and then acrylamide (13.04 mg, 183.50 µmol) was added; and the reaction mixture was stirred and reacted at 0° C. for 1 hour. After completion of the reaction, water (30 mL) was added for dilution, and extraction with ethyl acetate (20 mL×3) was performed. The organic phase was combined, washed with saturated brine (30 mL×3), dried over anhydrous sodium sulfate and filtered; and the solvent was removed from the filtrate under reduced pressure. The resulting residue was purified by preparative HPLC (mobile phase: acetonitrile/water; acid system: 0.05% TFA) to obtain a trifluoroacetate salt of target compound WX027. MS-ESI m/z: 421.1 [M+H]$^+$. $^1$H NMR (400 MHz, DMSO_$d_6$) δ: 10.97 (s, 1H), 8.67 (s, 2H), 8.05 (s, 1H), 8.03 (s, 1H), 8.02 (s, 1H), 7.97 (d, J=8.8 Hz, 1H), 7.47 (d, J=2.0 Hz, 1H), 7.21 (dd, J=2.2, 9.0 Hz, 1H), 4.35 (t, J=4.8 Hz, 2H), 4.22 (dd, J=4.8, 12.4 Hz, 1H), 3.46-3.43 (m, 2H), 3.18-3.07 (m, 1H), 2.87-2.77 (m, 1H), 2.68-2.60 (m, 1H), 2.45-2.31 (m, 1H), 2.22-2.13 (m, 1H), 2.12-2.05 (m, 2H), 1.83-1.74 (m, 2H), 1.68-1.57 (m, 1H), 1.38-1.23 (m, 5H).

Example 28

Hydrochloride Salt of WX028

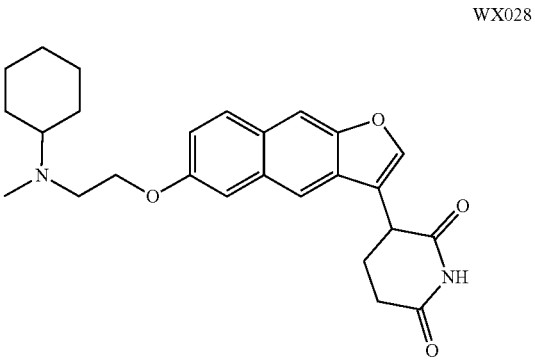

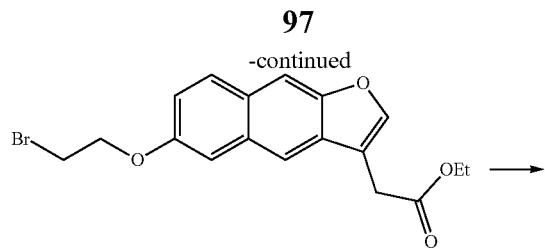

WX022-1

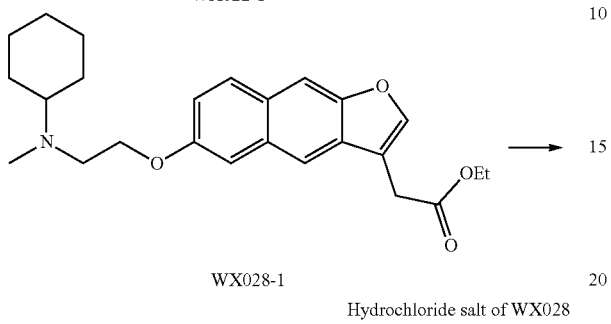

WX028-1

Hydrochloride salt of WX028

Step 1: Synthesis of Intermediate WX028-1

At 25° C. and under nitrogen atmosphere, intermediate WX022-1 (0.2 g, 492.80 μmol), N-methylcyclohexylamine (223.14 mg, 1.97 mmol) and potassium carbonate (136.22 mg, 985.61 μmol) were dissolved in acetonitrile (4 mL); and the reaction mixture was heated to 80° C. and stirred and reacted for 12 hours. After completion of the reaction, water (2 mL) was added to the reaction mixture, and extraction with ethyl acetate (5 mL×3) was performed. The organic phase was combined, washed with saturated brine (5 mL), dried over anhydrous sodium sulfate and filtered, and the filtrate was concentrated under reduced pressure to remove the solvent. The resulting residue was purified by a silica gel plate (eluent: dichloromethane/methanol=10/1, volume ratio) to obtain intermediate WX028-1. MS-ESI m/z: 410.1 [M+H]⁺. ¹H NMR (400 MHz, CDCl₃) δ: 7.88 (s, 1H), 7.83-7.79 (m, 2H), 7.72 (s, 1H), 7.24 (d, J=2.0 Hz, 1H), 7.16 (dd, J=2.4, 9.2 Hz, 1H), 4.22 (q, J=7.6 Hz, 2H), 4.19 (t, J=6.0 Hz, 2H), 3.78 (s, 2H), 2.97 (t, J=6.2 Hz, 2H), 2.54-2.47 (m, 1H), 2.44 (s, 3H), 1.94-1.86 (m, 2H), 1.85-1.78 (m, 2H), 1.34-1.30 (m, 3H), 1.29-1.23 (m, 5H), 1.17-1.09 (m, 1H).

Step 2: Synthesis of WX028

At 25° C. and under nitrogen atmosphere, intermediate WX028-1 (0.15 g, 360.13 μmol, purity: 98.32%) was dissolved in N,N-dimethylformamide (10 mL) and cooled to 0° C. in an ice-water bath; then acrylamide (25.60 mg, 360.13 μmol) and potassium tert-butoxide (44.45 mg, 396.15 μmol) were added to the reaction mixture; and the reaction mixture was stirred and reacted at 0° C. for 2 hours. After completion of the reaction, the reaction mixture was diluted by adding water (2 mL) and extracted with ethyl acetate (5 mL×3). The organic phase was combined, washed with saturated brine (5 mL×2), dried over anhydrous sodium sulfate and filtered, and the filtrate was concentrated under reduced pressure to remove the solvent. The resulting residue was purified by preparative HPLC (mobile phase: acetonitrile/water; acid system: HCl) to obtain a hydrochloride salt of target compound WX028. MS-ESI m/z: 435.1 [M+H]⁺. ¹H NMR (400 MHz, DMSO_d₆) δ: 10.97 (s, 1H), 10.20 (s, 1H), 8.04 (d, J=4.8 Hz, 2H), 8.01 (s, 1H), 7.96 (d, J=9.2 Hz, 1H), 7.48 (s, 1H), 7.20 (dd, J=2.0, 8.8 Hz, 1H), 4.56-4.45 (m, 2H), 4.22 (dd, J=5.0, 12.2 Hz, 1H), 3.73-3.63 (m, 1H), 2.94-2.85 (m, 1H), 2.82 (d, J=4.8 Hz, 4H), 2.74-2.57 (m, 2H), 2.42-2.30 (m, 1H), 2.22-2.14 (m, 1H), 2.12-2.03 (m, 2H), 1.89-1.78 (m, 2H), 1.68-1.57 (m, 1H), 1.53-1.40 (m, 2H), 1.35-1.23 (m, 2H), 1.19-1.07 (m, 1H).

Example 29

Hydrochloride Salt of WX029

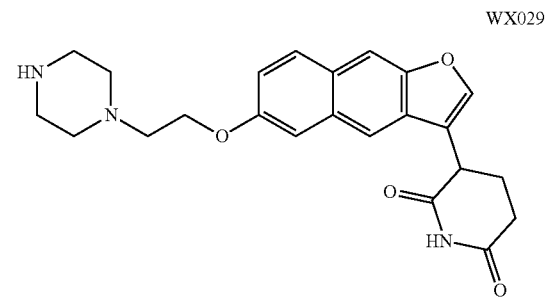 [SMILES: O=C1CCC(c2coc3cc4ccc(OCCN5CCNCC5)cc4cc23)C(=O)N1]

WX029

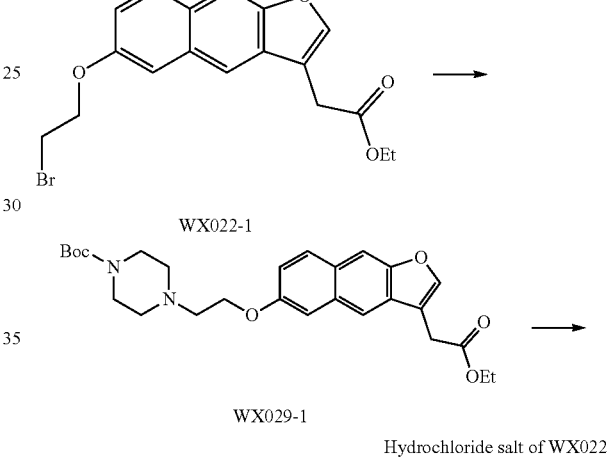

WX029-1

Hydrochloride salt of WX022

Step 1: Synthesis of Intermediate WX029-1

At room temperature and under nitrogen atmosphere, intermediate WX022-1 (252 mg, 609.02 μmol, purity: 91.16%) was dissolved in acetonitrile (15 mL), and then N-Boc-piperazine (567.15 mg, 3.05 mmol) and potassium carbonate (168.35 mg, 1.22 mmol) were added; and the reaction mixture was heated to 80° C. and stirred and reacted for 12 hours. After completion of the reaction, the reaction mixture was cooled to room temperature, poured into water (10 mL) and extracted with ethyl acetate (10 mL×3). The organic phase was combined, washed with saturated brine (30 mL×2), dried over anhydrous sodium sulfate and filtered; and the solvent was removed from the filtrate under reduced pressure. The resulting residue was purifiedd by preparative thin layer chromatography (developing agent: petroleum ether/ethyl acetate=1:1, volume ratio) to obtain intermediate WX029-1. MS-ESI m/z: 483.1 [M+H]⁺. ¹H NMR (400 MHz, MeOD_d₄) δ: 7.63 (s, 1H), 7.55-7.47 (m, 3H), 7.04 (d, J=2.4 Hz, 1H), 6.84 (dd, J=2.6, 9.0 Hz, 1H), 3.96 (t, J=5.4 Hz, 2H), 3.90 (q, J=7.0 Hz, 2H), 3.52 (s, 2H), 3.19-3.15 (m, 4H), 2.60 (t, J=5.4 Hz, 2H), 2.30 (t, J=5.0 Hz, 4H), 1.16 (s, 9H), 0.96 (t, J=7.2 Hz, 3H).

Step 2: Synthesis of WX029

At 0° C. and under nitrogen atmosphere, intermediate WX029-1 (0.28 g, 577.56 μmol, purity: 99.54%) was dissolved in N,N-dimethylformamide (5 mL); potassium tert-butoxide (71.29 mg, 635.32 μmol) was added, and then acrylamide (41.05 mg, 577.56 μmol) was added; and the reaction mixture was stirred and reacted at 0° C. for 1 hour. After completion of the reaction, water (30 mL) was added for dilution, and extraction with ethyl acetate (20 mL×3) was performed. The organic phase was combined, washed with saturated brine (30 mL×3), dried over anhydrous sodium sulfate and filtered; and the solvent was removed from the filtrate under reduced pressure. The resulting residue was dissolved in hydrochloric acid ethyl acetate (5 mL) and then stirred and reacted at room temperature for 12 hours. After completion of the reaction, the solvent was removed under reduced pressure. The resulting residue was purified by preparative HPLC (mobile phase: acetonitrile/water; acid system: 0.05% HCl) to obtain a hydrochloride salt of target compound WX029. MS-ESI m/z: 408.2 [M+H]$^+$. $^1$H NMR (400 MHz, DMSO_d$_6$) δ: 10.97 (s, 1H), 9.55 (s, 2H), 8.05 (s, 1H), 8.04 (s, 1H), 8.02 (s, 1H), 7.96 (d, J=9.2 Hz, 1H), 7.48 (d, J=2.0 Hz, 1H), 7.23 (dd, J=2.0, 8.8 Hz, 1H), 4.58-4.45 (m, 2H), 4.23 (dd, J=4.6, 12.2 Hz, 1H), 2.86-2.77 (m, 1H), 2.70-2.64 (m, 1H), 2.63-2.57 (m, 1H), 2.55-2.52 (m, 8H), 2.47-2.43 (m, 1H), 2.42-2.32 (m, 1H), 2.22-2.13 (m, 1H).

Example 30

Trifluoroacetate Salt of WX030

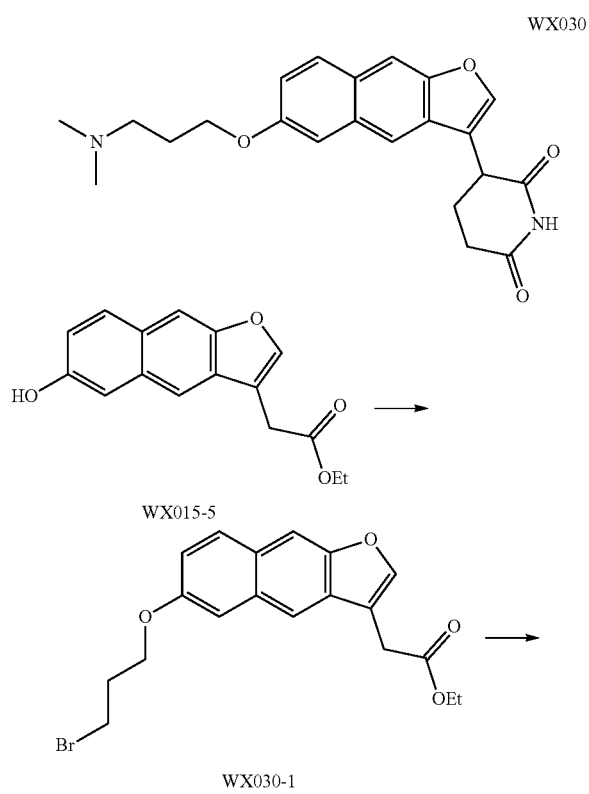

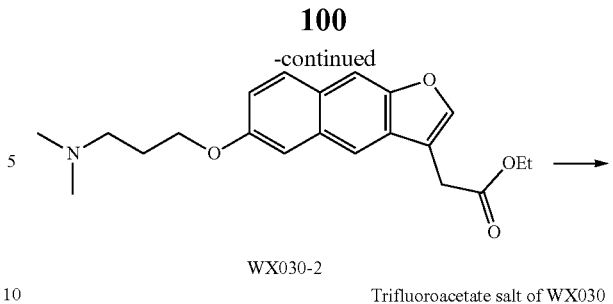

Step 1: Synthesis of Intermediate WX030-1

At room temperature and under nitrogen atmosphere, intermediate WX015-5 (0.5 g, 1.68 mmol, purity: 91%) was dissolved in toluene (50 mL), and then 1,3-dibromopropane (1.02 g, 5.05 mmol, 514.95 μL), potassium carbonate (697.99 mg, 5.05 mmol) and 18-Crown-6 (4.45 g, 16.83 mmol) were added; and the reaction mixture was heated to 110° C. and stirred and reacted for 12 hours. After completion of the reaction, the reaction mixture was cooled to room temperature, poured into water (50 mL) and extracted with ethyl acetate (30 mL×3). The organic phase was combined, successively washed with water (50 mL×2) and saturated brine (50 mL), dried over anhydrous sodium sulfate and filtered; and the solvent was removed from the filtrate under reduced pressure. The resulting residue was purified by column chromatography (eluent: petroleum ether/ethyl acetate=20/1-5/1, volume ratio) to obtain intermediate WX030-1. $^1$H NMR (400 MHz, CDCl$_3$) δ: 7.90 (s, 1H), 7.86-7.81 (m, 2H), 7.73 (s, 1H), 7.26-7.24 (m, 1H), 7.15 (dd, J=2.2, 9.0 Hz, 1H), 4.27-4.19 (m, 4H), 3.78 (s, 2H), 3.68 (t, J=6.4 Hz, 2H), 2.45-2.37 (m, 2H), 1.30 (t, J=7.0 Hz, 3H).

Step 2: Synthesis of Intermediate WX030-2

At room temperature and under nitrogen atmosphere, intermediate WX030-1 (0.21 g, 536.73 μmol) was dissolved in acetonitrile (20 mL), and then a dimethanamine aqueous solution (241.98 mg, 2.15 mmol, 9.94 μL) and potassium carbonate (148.36 mg, 1.07 mmol) were added; and the reaction mixture was heated to 80° C. and stirred and reacted for 12 hours. After completion of the reaction, the reaction mixture was cooled to room temperature, and the solvent was removed under reduced pressure. The residue was diluted by adding water (30 mL) and extracted with ethyl acetate (20 mL×3). The organic phase was combined, washed with water (30 mL×3), dried over anhydrous sodium sulfate and filtered; and the solvent was removed from the filtrate under reduced pressure. The resulting residue was purified by a silica gel plate (developing agent: dichloromethane/methanol=30/1, volume ratio) to obtain intermediate WX030-2. $^1$H NMR (400 MHz, CDCl$_3$) δ: 7.87 (s, 1H), 7.83-7.78 (m, 2H), 7.71 (s, 1H), 7.25 (d, J=2.4 Hz, 1H), 7.15 (dd, J=2.2, 9.0 Hz, 1H), 4.22 (q, J=7.2 Hz, 2H), 4.15 (t, J=6.4 Hz, 2H), 3.77 (s, 2H), 2.54 (t, J=7.4 Hz, 2H), 2.30 (s, 6H), 2.09-2.02 (m, 2H), 1.29 (t, J=7.0 Hz, 3H).

Step 3: Synthesis of WX030

At 0° C. and under nitrogen atmosphere, intermediate WX030-2 (0.12 g, 337.62 μmol) was dissolved in N,N-dimethylformamide (5 mL); potassium tert-butoxide (41.67 mg, 371.38 μmol) was added, and then acrylamide (24.00 mg, 337.62 μmol) was added; and the reaction mixture was stirred and reacted at 0° C. for 1 hour. After completion of the reaction, water (30 mL) was added for dilution, and extraction with ethyl acetate (20 mL×3) was performed. The organic phase was combined, washed with saturated brine (30 mL×3), dried over anhydrous sodium sulfate and filtered; and the solvent was removed from the filtrate under reduced pressure. The resulting residue was purified by preparative HPLC (mobile phase: acetonitrile/water; acid system: 0.05% TFA) to obtain a trifluoroacetate salt of target compound WX030. MS-ESI m/z: 381.0 [M+H]$^+$. $^1$H NMR (400 MHz, DMSO_d$_6$) δ: 10.97 (s, 1H), 9.53 (s, 1H), 8.02 (s, 2H), 7.98 (s, 1H), 7.93 (d, J=9.2 Hz, 1H), 7.40 (d, J=2.0 Hz, 1H), 7.15 (dd, J=2.0, 9.2 Hz, 1H), 4.22 (dd, J=4.6 Hz, 12.2 Hz, 1H), 4.17 (t, J=6.0 Hz, 2H), 3.29-3.25 (m, 2H), 2.84 (s, 6H), 2.68-2.62 (m, 2H), 2.45-2.38 (m, 2H), 2.20-2.14 (m, 2H).

Example 31

Hydrochloride Salt of WX031

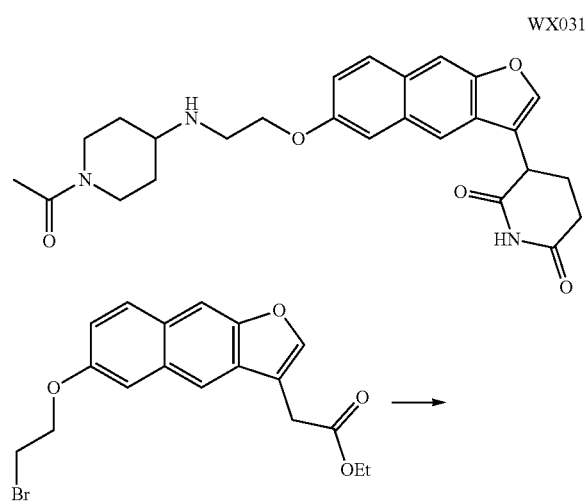

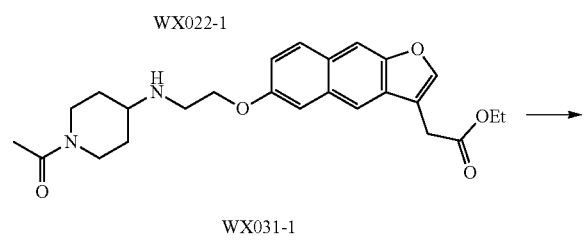

Hydrochloride salt of WX031

Step 1: Synthesis of Intermediate WX031-1

At room temperature and under nitrogen atmosphere, 1-acetyl piperidine-4-amine (86.84 mg, 610.71 μmol), potassium carbonate (42.20 mg, 305.35 μmol) and WX022-1 (0.06 g, 152.68 μmol) were dissolved in acetonitrile (3 mL); and the reaction mixture was stirred at 80° C. for 12 hours. After completion of the reaction, two parallel reaction batches were combined for treatment. Water (2 mL) was added to the reaction mixture, and extraction with ethyl acetate (5 mL×3) was performed. The organic phase was combined, washed with saturated brine (5 mL×2), dried over anhydrous sodium sulfate and filtered, and the filtrate was concentrated under reduced pressure to remove the solvent. The resulting residue was purified by a silica gel plate (developing agent: dichloromethane/methanol=10/1, volume ratio) to obtain intermediate WX031-1. MS-ESI m/z: 439.2 [M+H]$^+$. $^1$H NMR (400 MHz, CDCl$_3$) δ: 7.89 (s, 1H), 7.85-7.80 (m, 2H), 7.72 (s, 1H), 7.25 (d, J=2.4 Hz, 1H), 7.16 (dd, J=2.4, 9.2 Hz, 1H), 4.53-4.45 (m, 1H), 4.27-4.19 (m, 4H), 3.85-3.80 (m, 1H), 3.78 (s, 2H), 3.18-3.10 (m, 3H), 2.86-2.75 (m, 2H), 2.11 (s, 3H), 2.02-1.93 (m, 2H), 1.67-1.61 (m, 1H), 1.57-1.51 (m, 1H), 1.29 (t, J=7.2 Hz, 3H).

Step 2: Synthesis of WX031

At 0° C. and under nitrogen atmosphere, intermediate WX031-1 (112 mg, 255.29 μmol) was dissolved in N,N-dimethylformamide (5 mL); potassium tert-butoxide (31.51 mg, 280.82 μmol) was added, and acrylamide (18.15 mg, 255.29 μmol) was then added; and the reaction mixture was stirred and reacted at 0° C. for 1 hour. After completion of the reaction, water (30 mL) was added for dilution, and extraction with ethyl acetate (20 mL×3) was performed. The organic phase was combined, washed with saturated brine (30 mL×3), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain a hydrochloride salt of target compound WX031. MS-ESI m/z: 464.2 [M+H]$^+$. $^1$H NMR (400 MHz, DMSO_d$_6$) δ: 10.96 (s, 1H), 9.42 (s, 2H), 8.09-8.00 (m, 3H), 7.96 (d, J=8.8 Hz, 1H), 7.46 (d, J=1.2 Hz, 1H), 7.22 (dd, J=1.6, 9.2 Hz, 1H), 4.46-4.40 (m, 2H), 4.22 (dd, J=4.4, 12.0 Hz, 1H), 3.48-3.41 (m, 2H), 3.11-3.01 (m, 1H), 2.88-2.73 (m, 2H), 2.68-2.57 (m, 2H), 2.35-2.26 (m, 2H), 2.21-2.08 (m, 4H), 2.02 (s, 3H), 1.63-1.53 (m, 1H), 1.51-1.39 (m, 1H).

Example 32

WX032

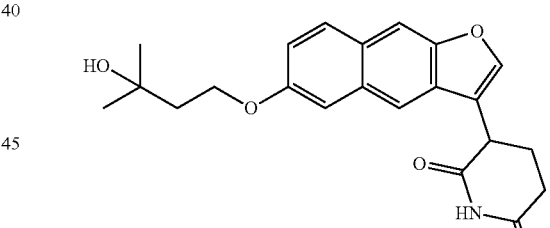

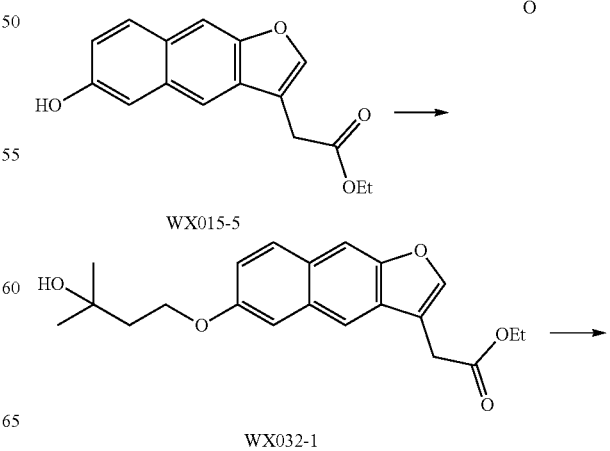

-continued

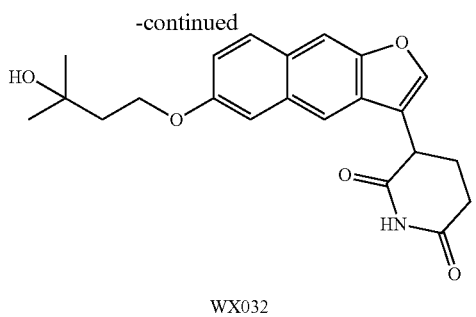

WX032

Step 1: Synthesis of Intermediate WX032-1

At room temperature and under nitrogen atmosphere, intermediate WX015-5 (200 mg, 740.72 µmol) was dissolved in N,N-dimethylformamide (30 mL), and then 2-methyl-4-bromo-2-butanol (494.93 mg, 2.96 mmol, 381.03 µL), potassium carbonate (307.12 mg, 2.22 mmol) and potassium iodide (61.48 mg, 370.36 µmol) were added; and the reaction mixture was stirred and reacted at 80° C. for 12 hours. After completion of the reaction, the reaction mixture was cooled to room temperature, poured into water (50 mL) and extracted with ethyl acetate (30 mL×3). The organic phase was combined, successively washed with water (50 mL×2) and saturated brine (50 mL), dried over anhydrous sodium sulfate and filtered; and the solvent was removed from the filtrate under reduced pressure. The resulting residue was purified by column chromatography (eluent: petroleum ether/ethyl acetate=20/1-5/1, volume ratio) to obtain intermediate WX032-1. MS-ESI m/z: 338.9 [M-OH]$^+$. $^1$H NMR (400 MHz, CDCl$_3$) δ: 7.90 (s, 1H), 7.85-7.81 (m, 2H), 7.72 (s, 1H), 7.29 (d, J=2.4 Hz, 1H), 7.15 (dd, J=2.6, 9.0 Hz, 1H), 4.33 (t, J=6.4 Hz, 2H), 4.23 (q, J=7.2 Hz, 2H), 3.78 (s, 2H), 2.09 (t, J=6.2 Hz, 2H), 1.37 (s, 6H), 1.30 (t, J=7.2 Hz, 3H).

Step 2: Synthesis of WX032

At 0° C. and under nitrogen atmosphere, intermediate WX032-1 (0.09 g, 243.02 µmol, purity: 96.24%) was dissolved in N,N-dimethylformamide (5 mL); potassium tert-butoxide (30.00 mg, 267.32 µmol) was added, and then acrylamide (17.27 mg, 243.02 µmol) was added; and the reaction mixture was stirred and reacted at 0° C. for 1 hour. After completion of the reaction, water (30 mL) was added for dilution, and extraction with ethyl acetate (20 mL×3) was performed. The organic phase was combined, washed with saturated brine (30 mL×3), dried over anhydrous sodium sulfate and filtered; and the solvent was removed from the filtrate under reduced pressure. The resulting residue was purified by preparative HPLC (mobile phase: acetonitrile/water; acid system: 0.05% HCl) to obtain target compound WX032. MS-ESI m/z: 364.1 [M-OH]$^+$. $^1$H NMR (400 MHz, DMSO-d$_6$) δ: 10.95 (s, 1H), 8.05-7.95 (m, 3H), 7.89 (d, J=9.2 Hz, 1H), 7.41 (s, 1H), 7.12 (d, J=8.8 Hz, 1H), 4.25-4.15 (m, 3H), 2.84-2.75 (m, 1H), 2.69-2.63 (m, 1H), 2.35-2.30 (m, 1H), 2.22-2.11 (m, 1H), 1.92 (t, J=6.6 Hz, 2H), 1.20 (s, 6H).

Experimental Example 1

In Vitro Test of IKZF3 Protein Level in Multiple Myeloma Cells

Experiment Object:

The WB method was used to study the regulation of IKZF3 protein level in multiple myeloma cells MM.1S with target compounds treatment at different concentrations.

Protocols:

1) The MM.1S cells were thawed and passaged twice;

2) The MM.1S cells were inoculated in a 6-well plate with 1×10$^6$ cells per well, and then treated with a certain concentration of the test intermediate;

3) After 16 hours of treatment, the cultured cell sample was dissolved in RIPA buffer (Sigma-Aldrich) or NETN buffer (150 mM NaCl, 1% NP-40, 50 mM Tris-HCl, pH=8.0) with a complete protease inhibitor (Roche) on ice and standing for 20 minutes;

4) After 15 minutes of centrifugation (rotating speed: 17950 rpm), the supernatant was collected and a protein quantitative test (Pierce BCA Protein Assay Kit, Thermo) was performed;

5) The same amount of 20 µg protein by SDS-PAGE was separated and transferred to PVDF or nylon membrane (Invitrogen);

6) 5% skimmed milk powder was added, and then incubated overnight at 4° C. in 5% BSA containing primary antibody anti-IKZF3 (NBP2-24495, Novps Biologicals) and anti-Actin (1844-1, Epitomics);

7) Finally, after reaction using HRP-linked secondary antibody (Goat-anti-rabbit IgG (sc-2004, Santa Cruz)) for 1 hour, a chemiluminescent substrate (Thermo Scientific) was used to detect bands on the membrane.

The experimental results are shown in FIG. 1.

Conclusion

After multiple myeloma cells MM.1S are treated with the compounds of the present disclosure at concentrations of 100 nM, or 500 nM and 50 nM, WB detection shows that the level of IKZF3 protein in the cells is significantly decreased.

Experimental Example 2

Evaluation of Anti-Proliferative Effects in Lymphoma Cell Lines OCI-LY10, DOHH2 and Mino Experiment object: In this experiment, the inhibitory effects of the test compounds on cell proliferation in the diffuse large B-cell lymphoma cell lines OCI-LY10 and DOHH2, and the mantle cell lymphoma cell line Mino were tested.

Experimental Materials:

1. Cell Lines and Culture Methods

| Cell lines | Tumor types | Growth characteristics | Culture methods |
|---|---|---|---|
| OCI-LY10 | Lymphoma | Suspension | RPMI 1640 + 10% FBS |
| DOHH2 | Lymphoma | Suspension | RPMI 1640 + 10% FBS |
| Mino | Lymphoma | Suspension | RPMI 1640 + 15% FBS |

2. Media and Reagents

| Media and reagents | Manufacturer | Catalog No. |
|---|---|---|
| RPMI 1640 | GIBCO | 22400-089 |
| Dulbecco's PBS | Hyclone | SH30256.01 |
| FBS | Hyclone | SY30087.03 |
| Antibiotic-antimycotic | GIBCO | 15240-062 |
| 0.25% Trypsin | GIBCO | 25200072 |
| DMSO | SIGMA | D2650 |
| 2-mercaptoethanol | SIGMA | 60-24-2 |

3. Multi-Well Plate

Greiner CELLSTAR® 96-well plate, flat-bottomed black plate (transparent bottom, with lid), #655090.

4. Reagents and Instruments Used in Cell Viability Experiments (1) Promega CellTiter-Glo Luminescence Cell Viability Detection Kit (Promega-G7573).

(2) 2104 EnVision® Plate Reader, PerkinElmer.

Protocols:

1. Cells Culture

The tumor cell lines were cultured in an incubator at 37° C. and 5% $CO_2$ under the above-mentioned culture conditions. The cells were passaged regularly, and cells in the logarithmic growth phase were taken for plating.

2. Cells Planking (1). The cells were stained with trypan blue and live cells were counted.

(2). The cell concentration was adjusted to an appropriate concentration.

| Cell line | Density (per 96-well) |
|---|---|
| OCI-LY10 | 5000 |
| DOHH2 | 5000 |
| Mino | 6000 |

(3). 90 μL of cell suspension was added to each well of the culture plate as shown in the table above, and cell-free culture solution was added to the blank control well.

(4). The culture plates were incubated overnight at 37° C., 5% $CO_2$, and 100% relative humidity in an incubator.

3. Preparation of compound storage solution

A 400× compound working solution was prepared. The compound was gradually diluted with DMSO from the highest concentration to the lowest concentration. The compound was freshly formulated when use every time.

4. Formulation of 10× compound working solution and treatment of cells with the compound (1). Formulation of 10× compound working solution: 76 μL of cell culture solution was added to a 96-well plate with a V-shaped bottom, and 4 μL of the compound from a 200× compound solution plate was pipetted and added to the cell culture solution in the 96-well plate. 4 μL of DMSO was added to the vehicle control and blank control. After adding the compound or DMSO, a multi-channel pipette was used for mixing well. 78 μL of cell culture solution was added to a 96-well plate with a V-shaped bottom, and 2 μL of the compound from the 400× compound storage solution was pipetted and added to the cell culture solution in the 96-well plate. 2 μL of DMSO was added to the vehicle control and blank control. After adding the compound or DMSO, a multi-channel pipette was used for mixing well.

(2). Dosing: 10 μL of the 10× compound working solution was taken and added to the cell culture plate. 10 μL mixture of DMSO and cell culture solution was added to the vehicle control and blank control.

(3). The 96-well cell plates were placed back into the incubator to culture OCI-LY10 (5 times dilution, incubate with the compound for 5 days), DOHH2 (3 times dilution, incubate with the compound for 4 days), Mino (3 times dilution, incubate with the compound for 4 days).

5. CellTiter-Glo Luminescence Cell Viability Detection

The following steps followed the instructions of Promega CellTiter-Glo Luminescence Cell Viability Detection Kit (Promega-G7573).

(1). The CellTiter-Glo buffer was thawed and standing to reach room temperature.

(2). CellTiter-Glo substrate was standing to reach room temperature.

(3). 10 mL CellTiter-Glo buffer was added to CellTiter-Glo substrate in a bottle to dissolve the substrate to formulate CellTiter-Glo working solution.

(4). The working solution was vortexed slowly for fully dissolution.

(5). The cell culture plates were taken out and standing for 30 minutes to equilibrate to room temperature.

(6). 50 μL (equal to half the volume of cell culture solution in each well) of CellTiter-Glo working solution was added into each well. The cell plates were wrapped with aluminum foil to protect the cell plate from light.

(7). The culture plates were shaken on an orbital shaker for 2 minutes to induce cell lysis.

(8). The culture plates were left at room temperature for 10 minutes to stabilize the luminescence signal.

(9). The luminous signal was detected on the 2104 EnVision plate reader.

6. Data Analysis

The following formula was used to calculate the inhibition rate (IR) of the test compound: IR (%)=(RLU of vehicle control−RLU of compound)/(RLU vehicle control−RLU blank control)*100%. The inhibition rate of different concentrations of the compound was calculated in Excel, and then GraphPad Prism software was used to draw the inhibition curve and calculate the relevant parameters, including the minimum inhibition rate, the maximum inhibition rate and $IC_{50}$.

Experimental results: The test results are shown in Table 1.

TABLE 1

The inhibitory effect of the compound of the present disclosure on cell proliferation in OCI-LY10, DOHH2 and Mino cell lines

| Compound | OCI-LY10 $IC_{50}$ (nM) | DOHH2 $IC_{50}$ (nM) | Mino $IC_{50}$ (nM) |
|---|---|---|---|
| WX001 | 28 | 63 | 72 |
| WX002 | 86 | / | / |
| WX003 | 83 | / | / |
| WX005 | 6 | / | / |

"/" means not detected.

Conclusion

The compound of the present disclosure exhibits an excellent inhibitory effect on cell proliferation in lymphoma cell lines OCI-LY10, DOHH2 and Mino.

Experimental Example 3

Evaluation the Pharmacokinetic Properties of Test Compound in Mice

Experiment Object:

In this study, C57BL male mice were selected as the test animals, and the LC/MS/MS method was used to quantitatively determine the drug concentration in the plasma of the test compound and the reference compound administered orally to evaluate the pharmacokinetic profile of the test compound in mice.

Experimental Materials:

C57Balb/c (C57) mice (male, 20-30 g, 7-10 weeks old, from Beijing Vital River or Shanghai SLAC).

Experiment Operation:

A clear solution or suspension of the test compound was administrated to C57 mice (fasted overnight) by oral gavage. Blood was collected from jugular vein at pre-dose and 0.5, 1, 2, 4, 6, 8, 24 hours post-dose, the collected blood samples were placed in an anticoagulant tube (Jiangsu Kangjian Medical Co., Ltd.) supplemented with EDTA-K2, and the mixture was vortexed and centrifuged at 13000 rpm for 10 minutes. The LC-MS/MS method was used to determine the plasma concentration, and the relevant pharmacokinetic parameters were calculated using the non-compartmental model linear logarithmic trapezoidal method by WinNonlin™ Version 6.3 (Pharsight, Mountain View, Calif.).

Experimental results: The test results are shown in Table 2.

TABLE 2

Pharmacokinetic parameters of the test compounds in mice

| Mouse pharmacokinetic parameters | Oral (10 mg/kg) | | |
|---|---|---|---|
| | Peak concentration (µM) | Time to peak (h) | Area under the concentration-time curve (0-inf, µM · h) |
| WX015 | 5.14 | 0.50 | 13.29 |
| Hydrochloride salt of WX022 | 2.58 | 0.50 | 7.42 |

Conclusion

The experimental results show higher oral plasma systemic exposures ($AUC_{0-inf}$) of hydrochloride salts of WX015 and WX022. In rodent mice, hydrochloride salts of WX015 and WX022 have better pharmacokinetic properties.

Experimental Example 4

In Vivo Pharmacodynamic Study of the Compound in Subcutaneous Xenograft Tumor CB-17 SCID Model of Human Lymphoma OCI-LY10 Cells Cells culture: Human lymphoma OCI-LY10 cells (National Cancer Institute) were cultured in a monolayer method in vitro (culture conditions: RPMI-1640 medium with 10% fetal bovine serum, 100 U/mL penicillin and 100 µg/mL streptomycin; 37° C., 5% $CO_2$ incubator). Pancreatin-EDTA was used twice a week for conventional digestion and passage. When a cell saturation of 80%-90% and the required cell number were achieved, the cells were collected, counted and seeded.

Animal: CB-17 SCID mouse, female, 6-8 weeks old, weighing 18-22 grams.

Protocols:

0.2 mL ($10 \times 10^6$ cells) of OCI-LY10 cells (with matrigel in a volume ratio of 1:1) were subcutaneously inoculated on the right back of each mouse. The grouping and administration were started when the average tumor volume reached about 139 $mm^3$. One dosing cycle was seven days, and the compound was administered once a day with an interval of 24 hours. The test compound was administered orally for a total of four cycles. The dose of the test compound WX001 was 60 mg/kg. The tumor volume was measured twice a week with a two-dimensional caliper, expressed in cubic millimeters, and calculated by the following formula: $V = 0.5 \times a \times b^2$, in which a and b were the long diameter and short diameter of the tumor, respectively. The anti-tumor efficacy was determined by dividing the average increase of tumor volume of animals treated with the compound by that of untreated animals.

Experimental Results:

The test results are shown in Table 3.

TABLE 3

Test results of the compound of the present disclosure in subcutaneous xenograft tumor CB-17 SCID model for human lymphoma OCI-LY10 cells

| Groups | Dosage | Tumor volume ($mm^3$) (Day 0) | Tumor volume ($mm^3$) (Day 27) | TGI (%) (Day 27) |
|---|---|---|---|---|
| Vehicle control | 0 mg/kg | 139 | 1088 | / |
| WX001 | 60 mg/kg | 139 | 87 | 105.5 |

TGI: Tumor Growth Inhibition. TGI (%)=[1−(average tumor volume at the end of administration in a treatment group−average tumor volume at the beginning of administration in this treatment group)/(average tumor volume at the end of administration in the solvent control group−average tumor volume at the beginning of administration in the solvent control group)]×100%.

CONCLUSION

The compound WX001 of the present disclosure has shown a significant tumor-shrinking effect in a human lymphoma OCI-LY10 model.

What is claimed is:

1. A compound represented by formula (I), or a pharmaceutically acceptable salt thereof,

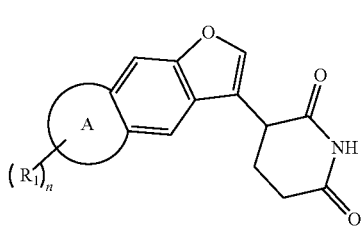

wherein n is selected from 0, 1, 2 and 3;

$R_1$ is selected from independently selected from H, F, Cl, Br, I, OH, $NH_2$, $C_{1-6}$alkyl, $C_{1-6}$alkoxy and

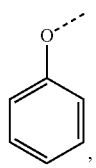

wherein the $C_{1-6}$alkyl, $C_{1-6}$alkoxy and

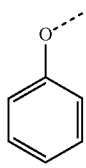

are optionally substituted with 1, 2 or 3 $R_a$;

$R_a$ is independently selected from H, F, Cl, Br, I, OH, $NH_2$, $C_{1-10}$alkyl, $C_{1-10}$alkylamino, —NHC(=O)—$C_{1-10}$alkyl, 5- to 10-membered heterocycloalkyl, 5- to 10-membered heterocycloalkylamino and $C_{5-10}$cycloalkylamino, wherein the $C_{1-10}$alkyl, $C_{1-10}$alkoxy, $C_{1-10}$-alkylamino, —NHC(=O)—$C_{1-10}$alkyl, 5- to 10-membered heterocycloalkyl, 5- to 10-membered heterocycloalkylamino and $C_{5-10}$cycloalkylamino are optionally substituted with 1, 2 or 3 R;

R is independently selected from F, Cl, Br, I, OH, $NH_2$, CN, Me and

ring A is selected from 5- to 6-membered heteroaryl, phenyl, $C_{4-6}$ cycloalkyl, 4- to 7-membered heterocycloalkyl and 4- to 7-membered heterocycloalkenyl;

the hetero in the 5- to 6-membered heteroaryl, 4- to 7-membered heterocycloalkyl, 5- to 10-membered heterocycloalkyl and 5- to 10-membered heterocycloalkylamino is 1, 2, 3 or 4 heteroatoms or heteroatom groups independently selected from —NH—, —O—, —S— and N respectively.

2. The compound as defined in claim 1 or a pharmaceutically acceptable salt thereof, wherein, $R_a$ is independently selected from H, F, Cl, Br, I, OH, $NH_2$, $C_{1-6}$alkyl, $C_{1-6}$alkoxy, $C_{1-6}$alkylamino, —NHC(=O)—$C_{1-6}$alkyl, 5- to 8-membered heterocycloalkyl, 5- to 8-membered heterocycloalkylamino and $C_{5-8}$cycloalkylamino, wherein the $C_{1-6}$alkyl, $C_{1-6}$alkoxy, $C_{1-6}$alkylamino, —NHC(=O)—$C_{1-6}$alkyl, 5- to 8-membered heterocycloalkyl, 5- to 8-membered heterocycloalkylamino and $C_{5-8}$cycloalkylamino are optionally substituted with 1, 2 or 3 R.

3. The compound as defined in claim 2 or a pharmaceutically acceptable salt thereof, wherein, Ra is independently selected from H, F, Cl, Br, I, OH, $NH_2$, $C_{1-3}$alkyl, $C_{1-3}$alkoxy, $C_{1-3}$alkylamino, —NHC(=O)—$C_{1-3}$alkyl, piperidinyl, piperazinyl, morpholinyl, pyranyl, pyrrolidinyl, cyclohexylamino, tetrahydropyranylamino, piperidinylamino, piperazinylamino and 3-azabicyclo[3,1,0]hexyl, wherein the $C_{1-3}$alkyl, $C_{1-6}$alkoxy, $C_{1-6}$alkylamino, —NHC(=O)—$C_{1-3}$alkyl, piperidinyl, piperazinyl, morpholinyl, pyranyl, pyrrolidinyl, cyclohexylamino, tetrahydropyranylamino, piperidinylamino, piperazinylamino and 3-azabicyclo[3,1,0]hexyl are optionally substituted with 1, 2 or 3 R.

4. The compound as defined in claim 3 or a pharmaceutically acceptable salt thereof, wherein, $R_a$ is independently selected from H, F, Cl, Br, I, OH, $NH_2$, Me, Et,

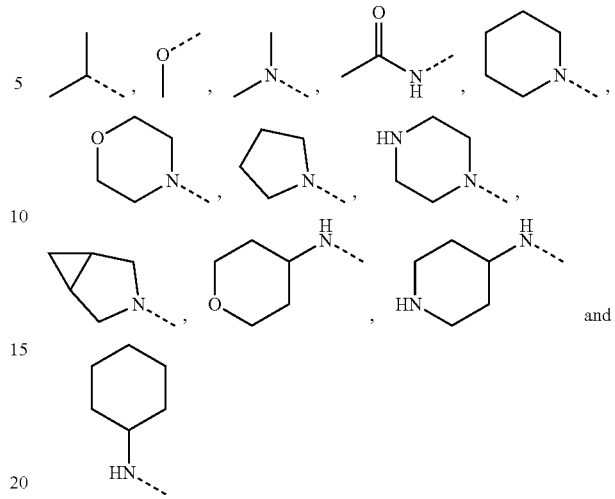

wherein, the Me, Et,

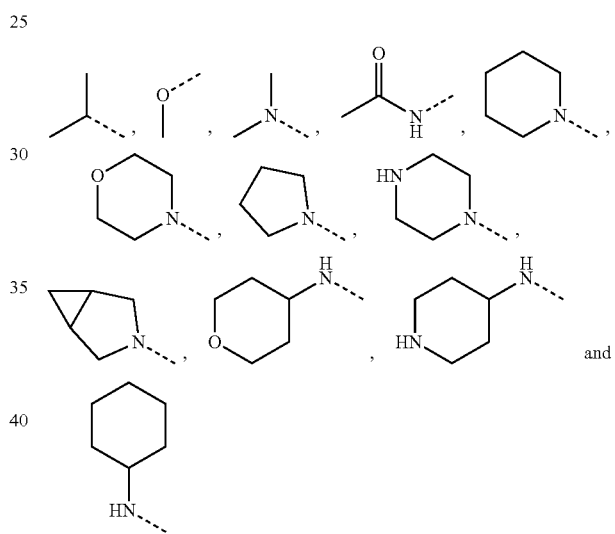

are optionally substituted with 1, 2 or 3 R.

5. The compound as defined in claim 4 or a pharmaceutically acceptable salt thereof, wherein, $R_a$ is independently selected from H, F, Cl, Br, I, OH, $NH_2$,

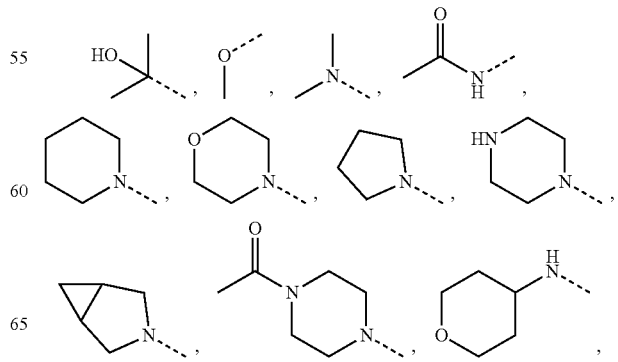

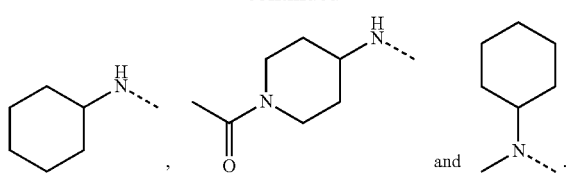

6. The compound as defined in claim 1 or a pharmaceutically acceptable salt thereof, wherein, $R_1$ is independently selected from H, F, Cl, Br, I, OH, $NH_2$, Me, $C_{1-6}$alkoxy and

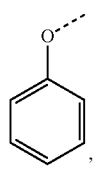

wherein the Me, $C_{1-6}$alkoxy and

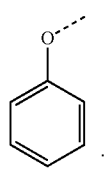

are optionally substituted with 1, 2 or 3 $R_a$.

7. The compound as defined in claim 6 or a pharmaceutically acceptable salt thereof, wherein, $R_1$ is selected from H, Me,

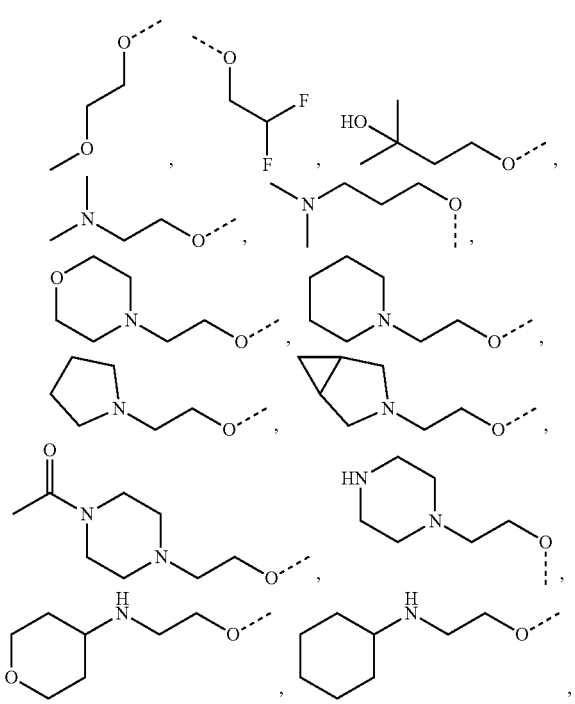

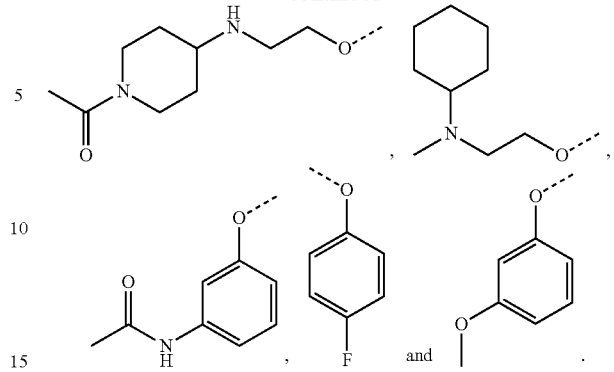

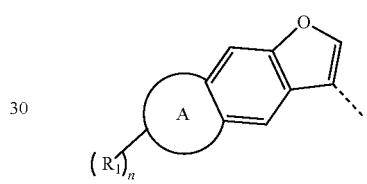

8. The compound as defined in claim 1 or a pharmaceutically acceptable salt thereof, wherein, ring A is selected from phenyl, 1,3-dioxolane, morpholinyl, tetrahydrofuryl, 2,3-dihydrofuryl, furyl, pyrazolyl, thiazolyl, 4,5-dihydrothiazolyl, oxazolyl, 2,3-dihydrooxazolyl, pyridinyl and 2,3-dihydropyridinyl.

9. The compound as defined in claim 1 or a pharmaceutically acceptable salt thereof, wherein, the structural unit is selected from

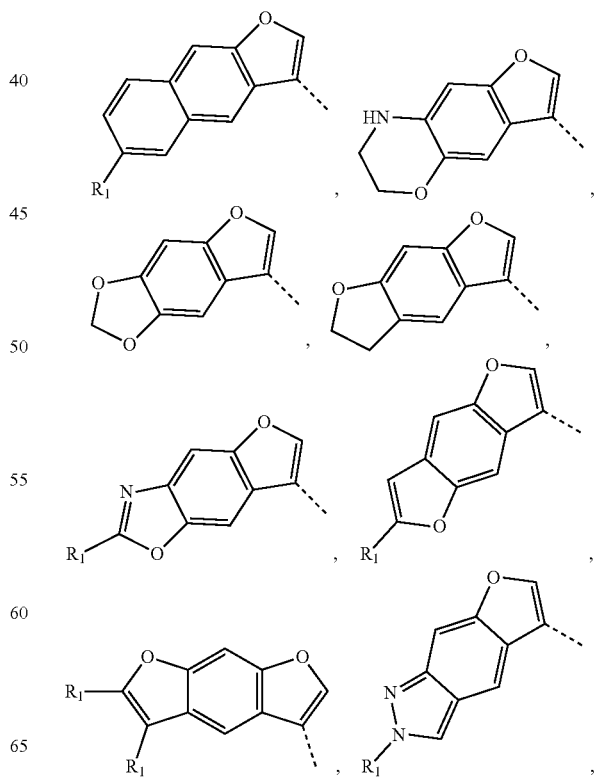

-continued
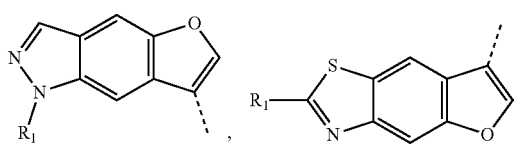
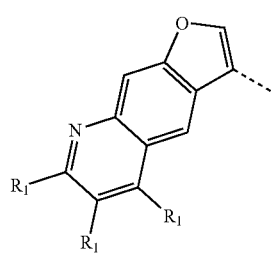
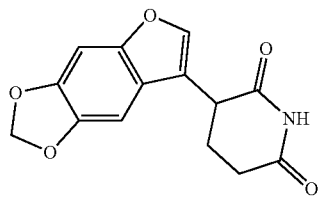
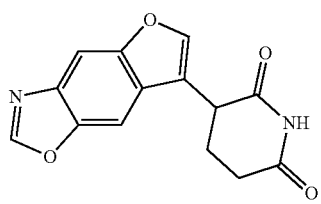
10. The compound as defined in claim 1 or a pharmaceutically acceptable salt thereof, selected from
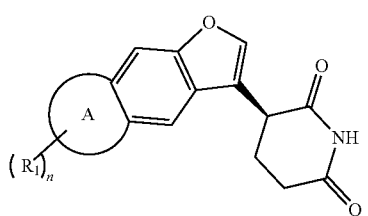 (I-1)
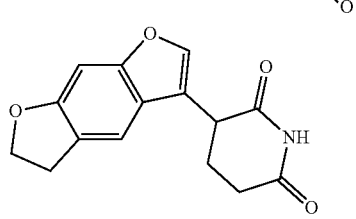
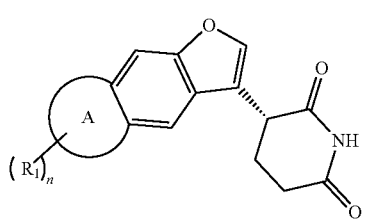 (I-2)
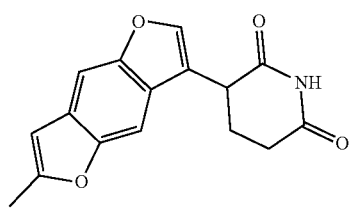
wherein, n, $R_1$ and ring A are as defined in claim 1.
11. A compound represented by the following formula or a pharmaceutically acceptable salt thereof, selected from:
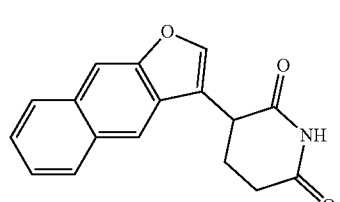
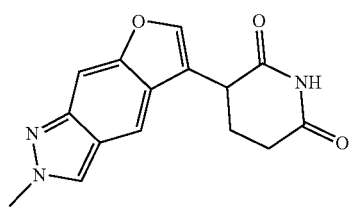
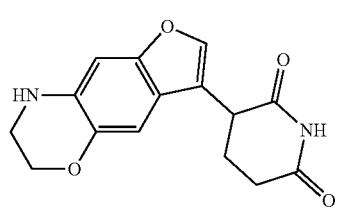
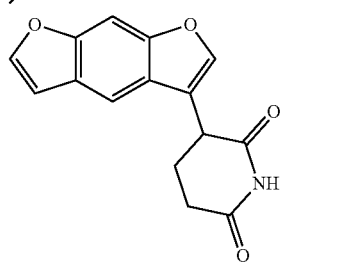

115
-continued
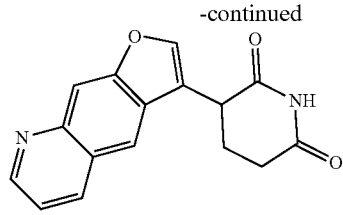
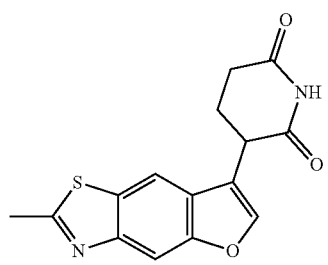
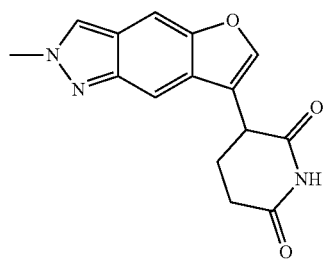
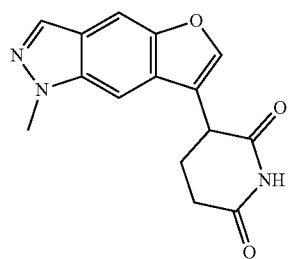
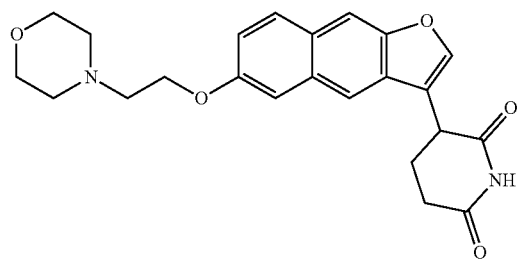
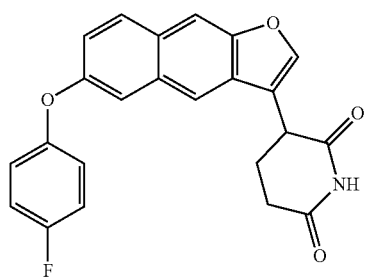
116
-continued
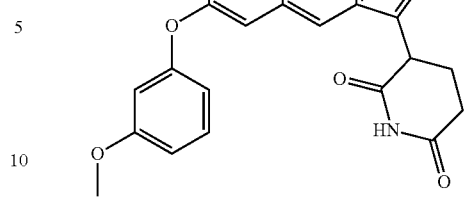
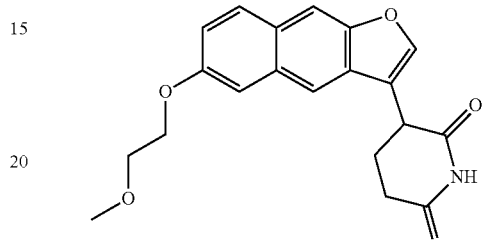
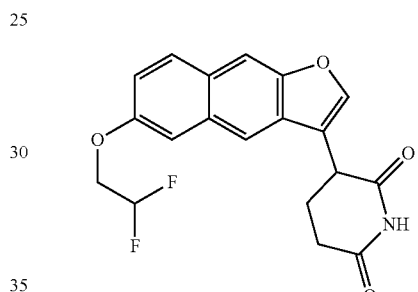
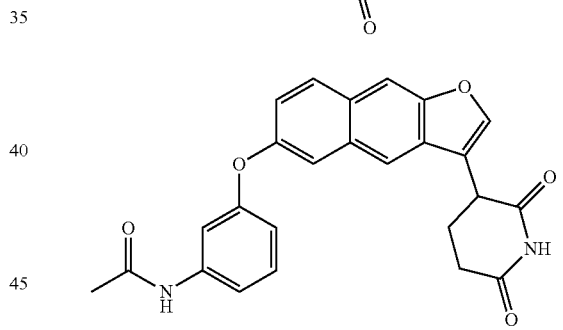
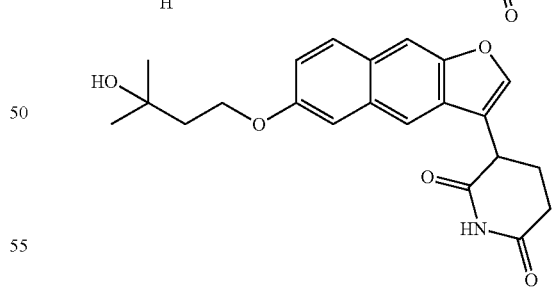
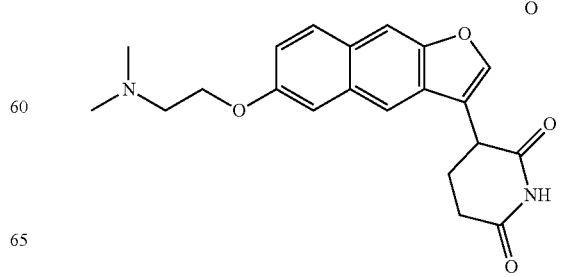

117
-continued
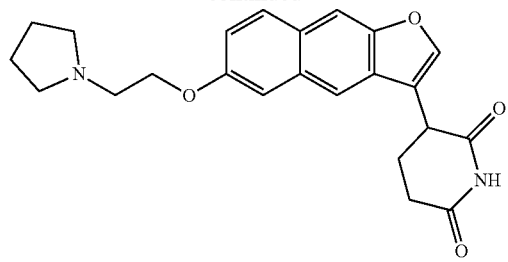
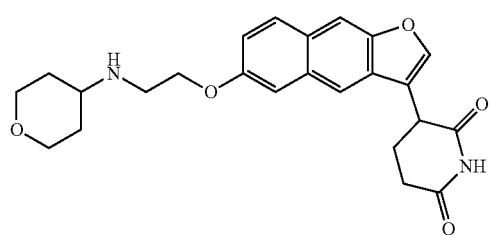
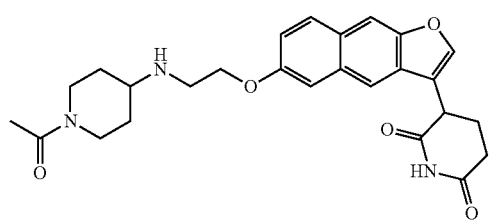
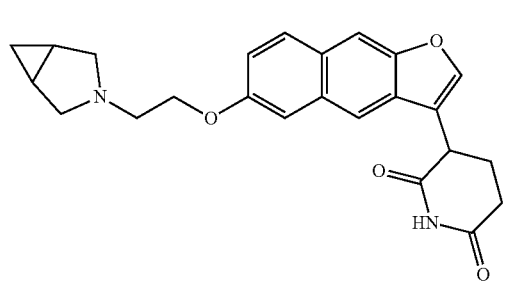
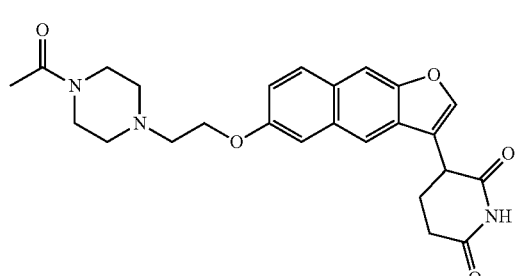
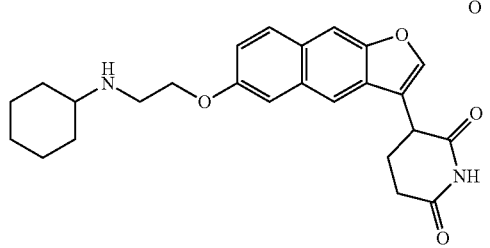
118
-continued
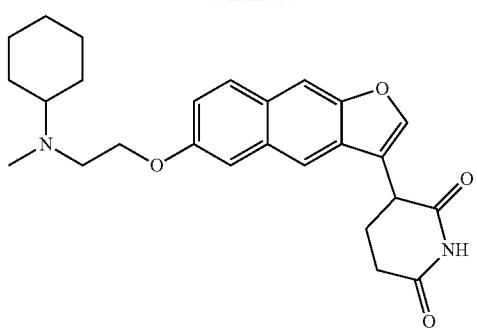
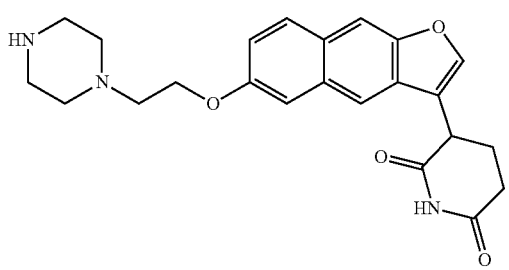
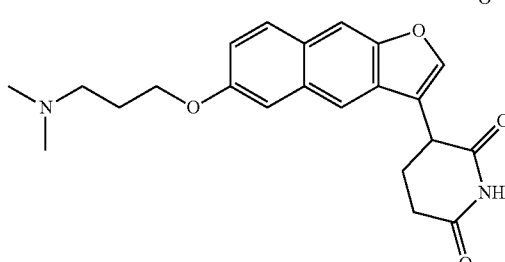
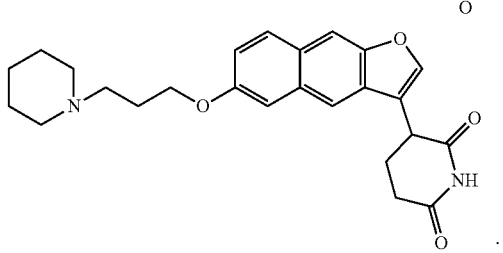
12. The compound as defined in claim 11 or a pharmaceutically acceptable salt thereof, selected from
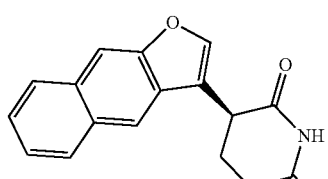
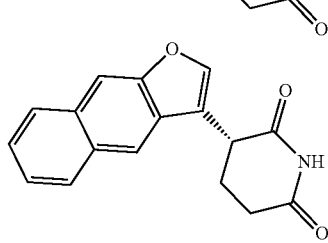

119
-continued
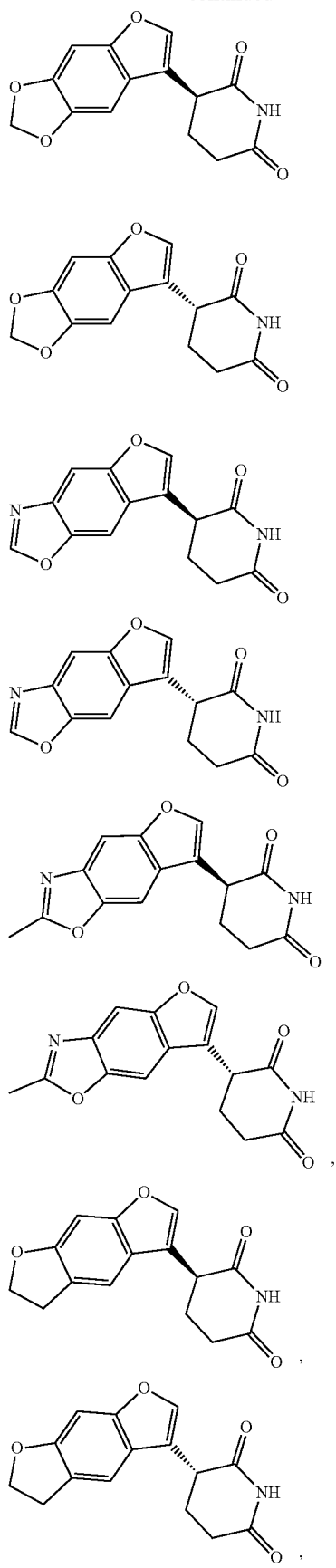
120
-continued
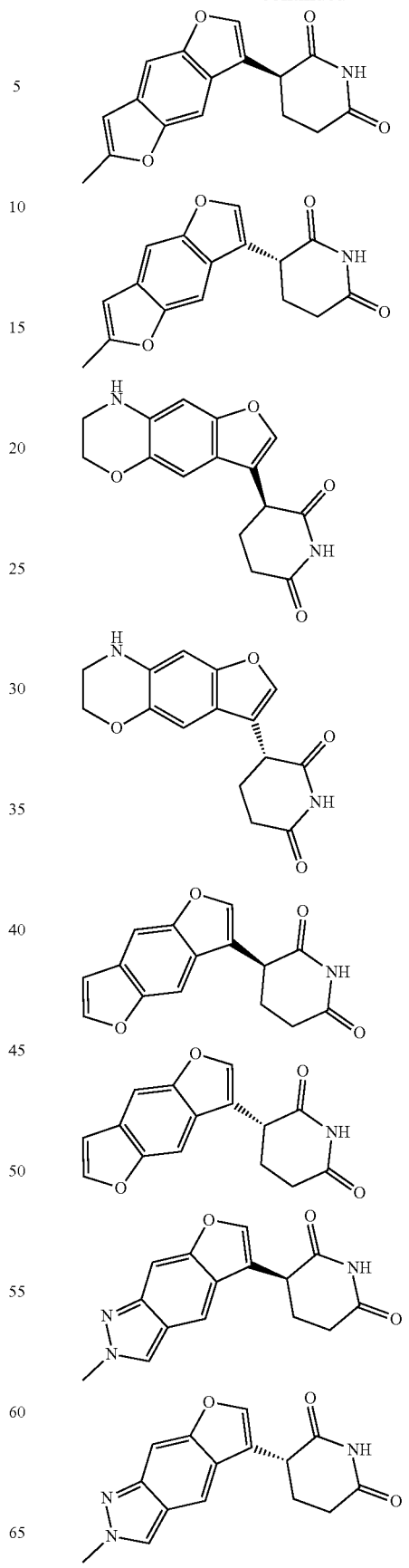

121
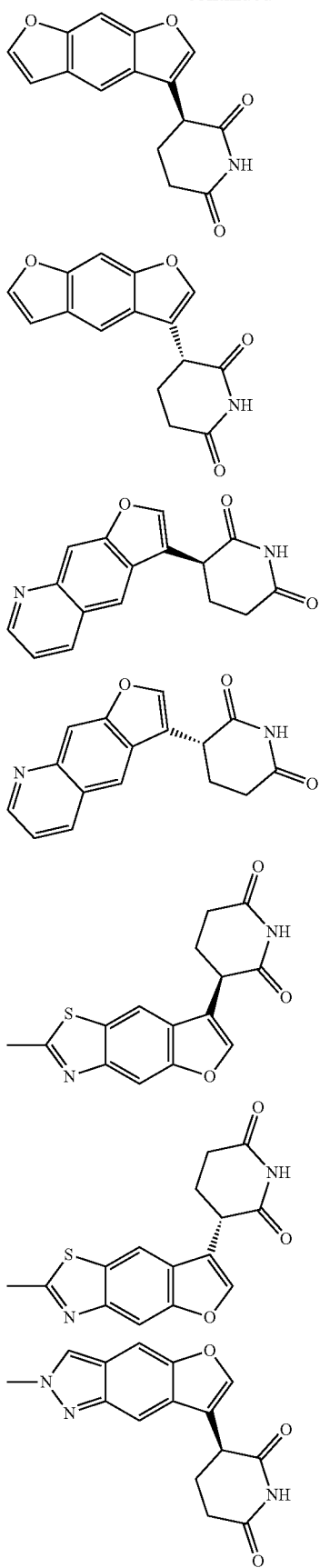
122
-continued
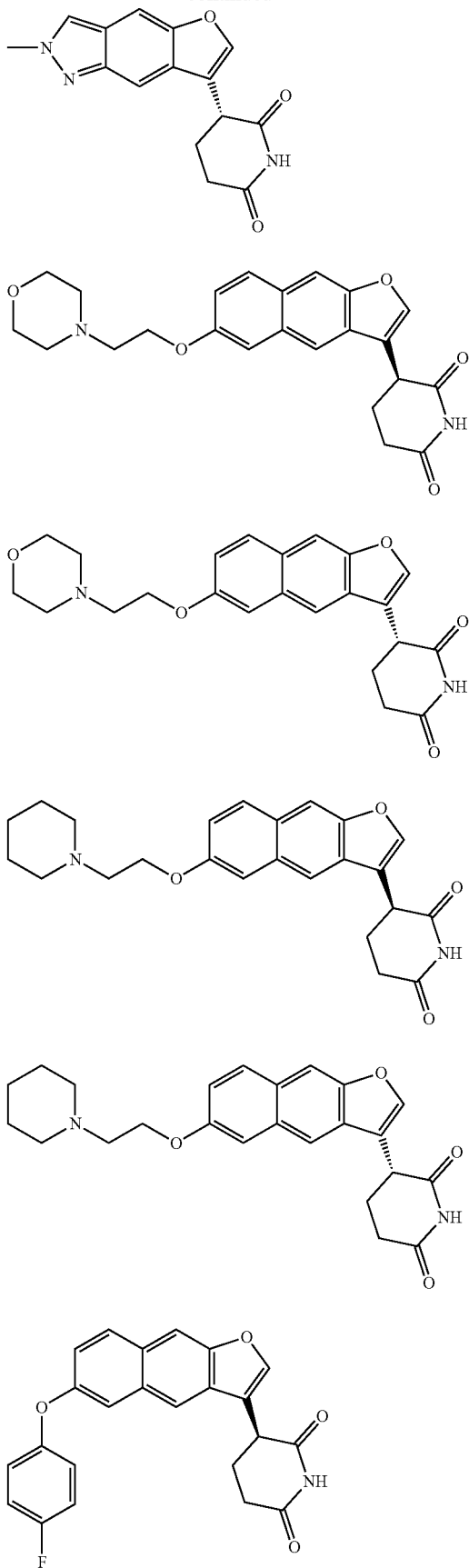

123
-continued
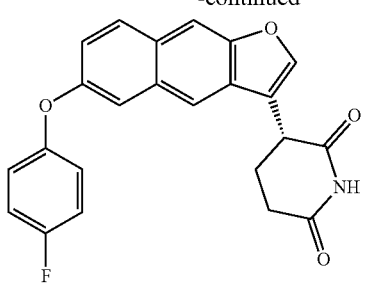
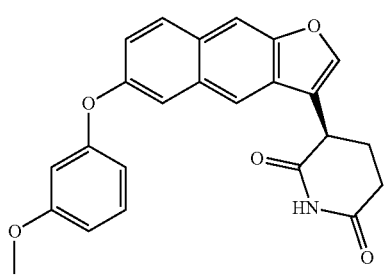
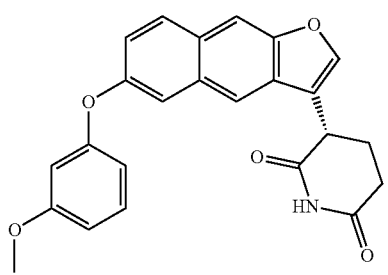
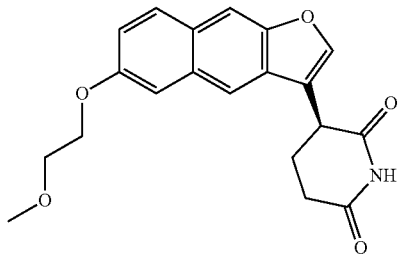
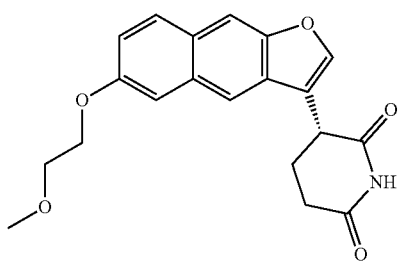
124
-continued
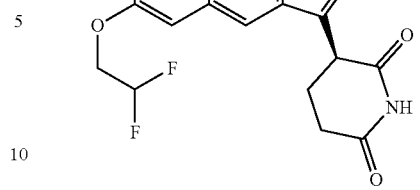
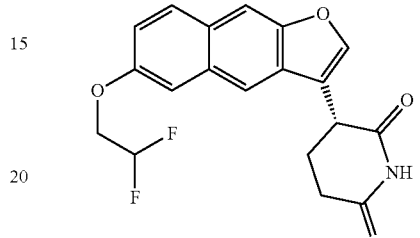
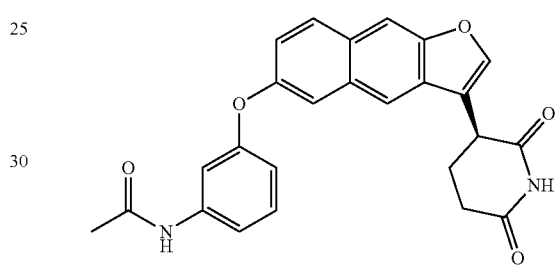
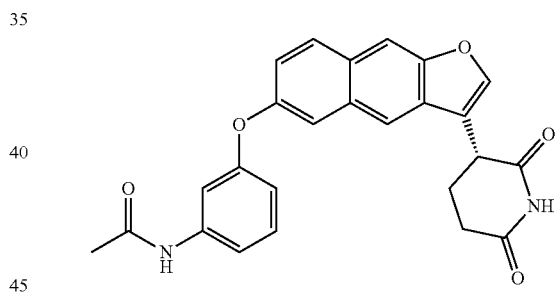
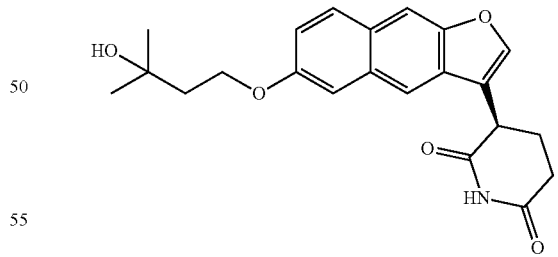
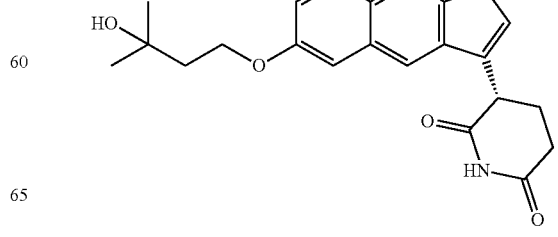

125
-continued
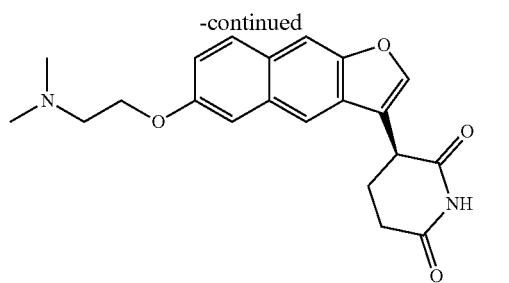
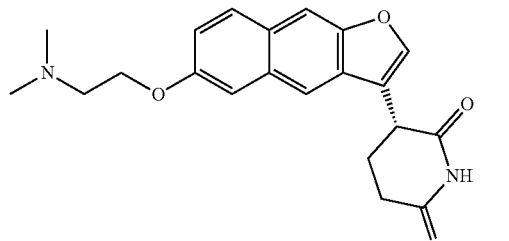
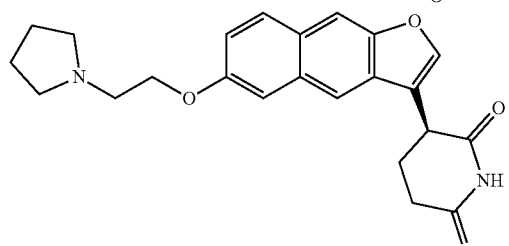
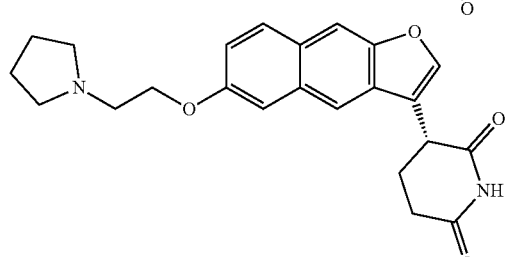
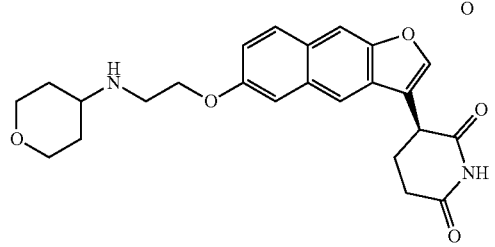
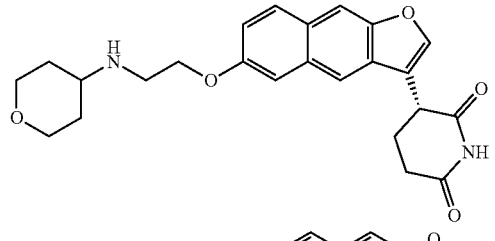
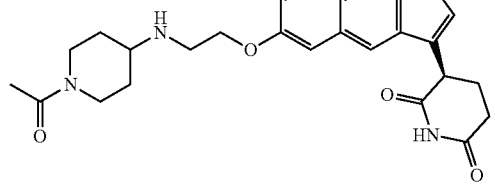
126
-continued
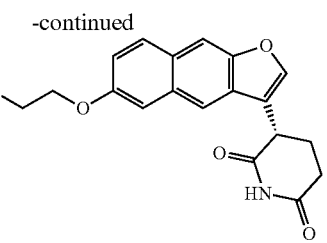
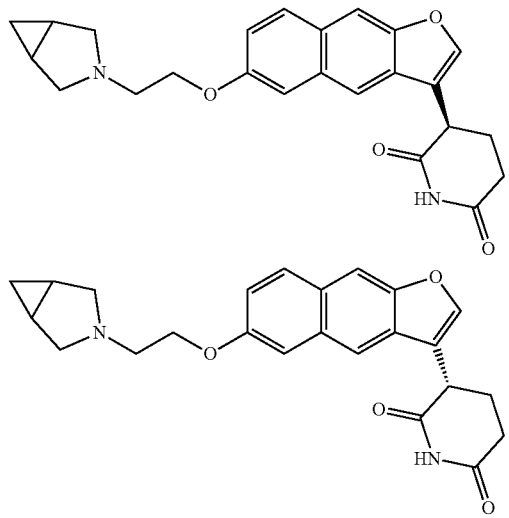
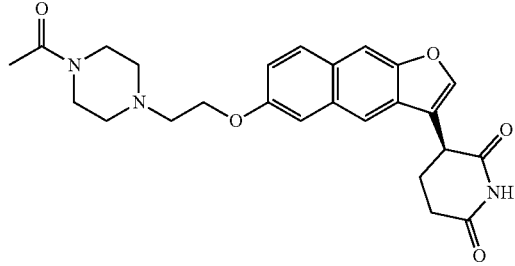
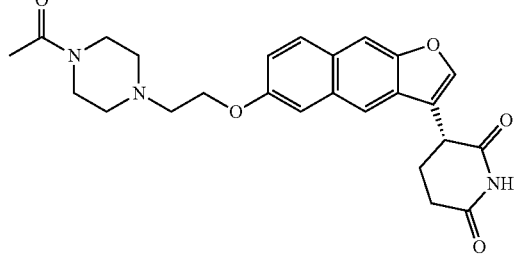
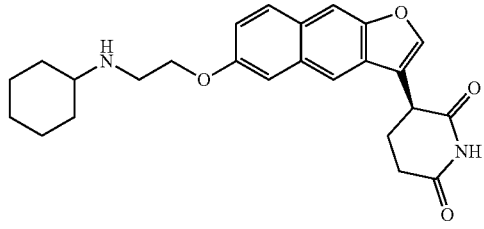
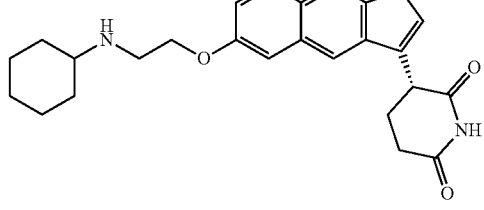

127
-continued

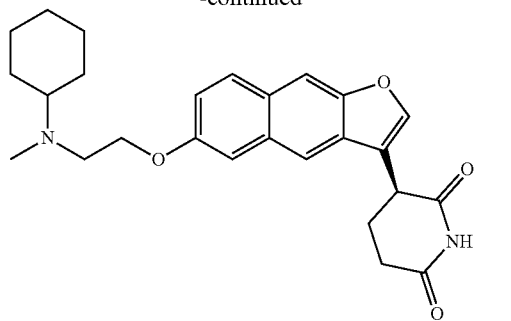

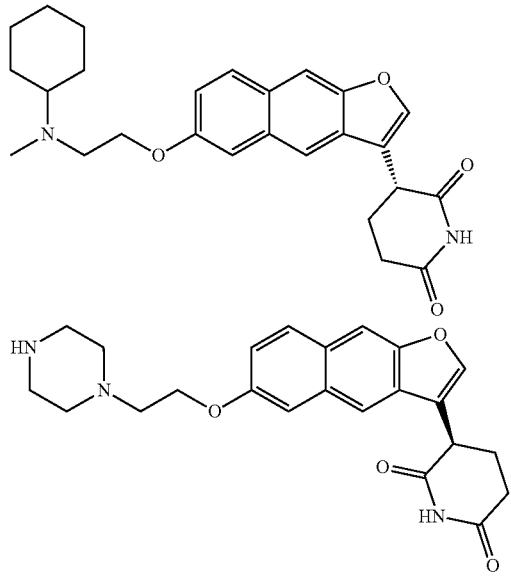

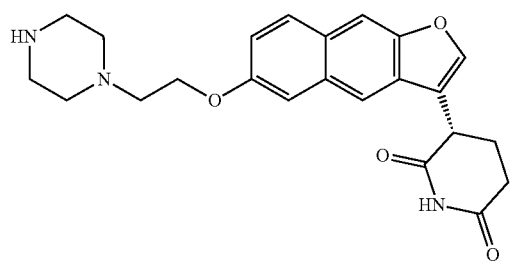

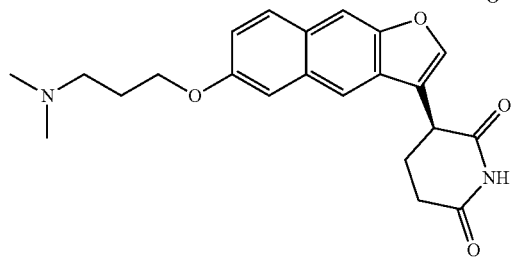

128
-continued

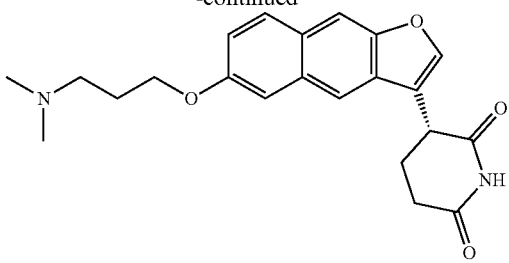

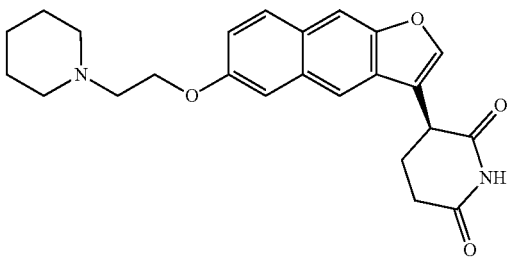

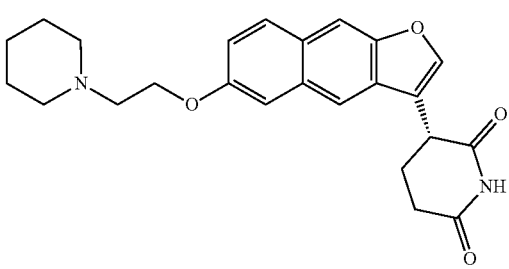

13. A pharmaceutical composition, comprising a therapeutically effective amount of the compound as defined in claim 1 or a pharmaceutically acceptable salt thereof as an active ingredient and a pharmaceutically acceptable carrier.

14. A method for treating a disease related to CRBN protein in a subject in need thereof, comprising administering an effective amount of the compound as defined in claim 1 or a pharmaceutically acceptable salt thereof to the subject.

15. A method for treating a disease related to CRBN protein in a subject in need thereof, comprising administering an effective amount of the composition as defined in claim 13 to the subject.

* * * * *